United States Patent
Slassi et al.

(10) Patent No.: US 10,696,670 B2
(45) Date of Patent: Jun. 30, 2020

(54) FLUORINATED IMIDAZO[4,5-C]QUINOLINE DERIVATIVES AS INHIBITORS OF BROMODOMAIN CONTAINING PROTEINS

(71) Applicant: Trillium Therapeutics Inc., Mississauga (CA)

(72) Inventors: Abdelmalik Slassi, Mississauga (CA); Peter Dove, Burlington (CA)

(73) Assignee: Trillium Therapeutics Inc., Mississauga (CA)

( * ) Notice: Subject to any disclaimer, the term of this patent is extended or adjusted under 35 U.S.C. 154(b) by 0 days.

(21) Appl. No.: 16/298,762

(22) Filed: Mar. 11, 2019

(65) Prior Publication Data

US 2019/0202825 A1      Jul. 4, 2019

Related U.S. Application Data

(62) Division of application No. 15/546,324, filed as application No. PCT/CA2016/050097 on Feb. 3, 2016, now Pat. No. 10,259,809.

(60) Provisional application No. 62/111,251, filed on Feb. 3, 2015.

(51) Int. Cl.
| | |
|---|---|
| *C07D 471/04* | (2006.01) |
| *A61K 31/437* | (2006.01) |
| *A61K 31/4745* | (2006.01) |
| *A61K 45/06* | (2006.01) |
| *A61K 31/496* | (2006.01) |
| *A61K 31/5377* | (2006.01) |
| *A61K 51/04* | (2006.01) |

(52) U.S. Cl.
CPC .......... *C07D 471/04* (2013.01); *A61K 31/437* (2013.01); *A61K 31/4745* (2013.01); *A61K 31/496* (2013.01); *A61K 31/5377* (2013.01); *A61K 45/06* (2013.01); *A61K 51/0455* (2013.01)

(58) Field of Classification Search
CPC .................................................... C07D 471/04
See application file for complete search history.

(56) References Cited

U.S. PATENT DOCUMENTS 10,259,809 B2    4/2019   Slassi et al.

FOREIGN PATENT DOCUMENTS

| CA | 2843537 A1 | 2/2013 |
|---|---|---|
| CA | 2601542 C | 9/2018 |
| WO | 2011054846 A1 | 5/2011 |
| WO | 2012143416 A2 | 10/2012 |

OTHER PUBLICATIONS

International Search Report and Written Opinion of corresponding International Application No. PCT/CA2016/050097 dated Jun. 6, 2016.
Seal J., et al., "Identification of Novel Series of BET Family Bromodomain inhibitors: Binding Mode and Profile I-BET151 (GSK1210151A)", Bioorganic & Medicinal Chemistry Letters, Feb. 24, 2002, vol. 22(8), pp. 2968-2972.
Supplementary European Search Report of corresponding European Patent Application No. 16746053.1 dated Jun. 6, 2018.
International Preliminary Report on Patentability of corresponding international Application No. PCT/CA2018/050097 dated Aug. 8, 2017.

*Primary Examiner* — Brian E McDowell
(74) *Attorney, Agent, or Firm* — Bereskin & Parr LLP/S.E.N.C.R.L., S.R.L.; Patricia Folkins

(57) ABSTRACT

A novel class of fluorinated derivatives of Formula I have been prepared and found to be useful in the treatment of cancers and other disorders related mediated by Bromodomain-Containing Proteins.

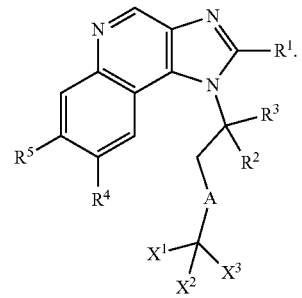

FORMULA I

18 Claims, 1 Drawing Sheet

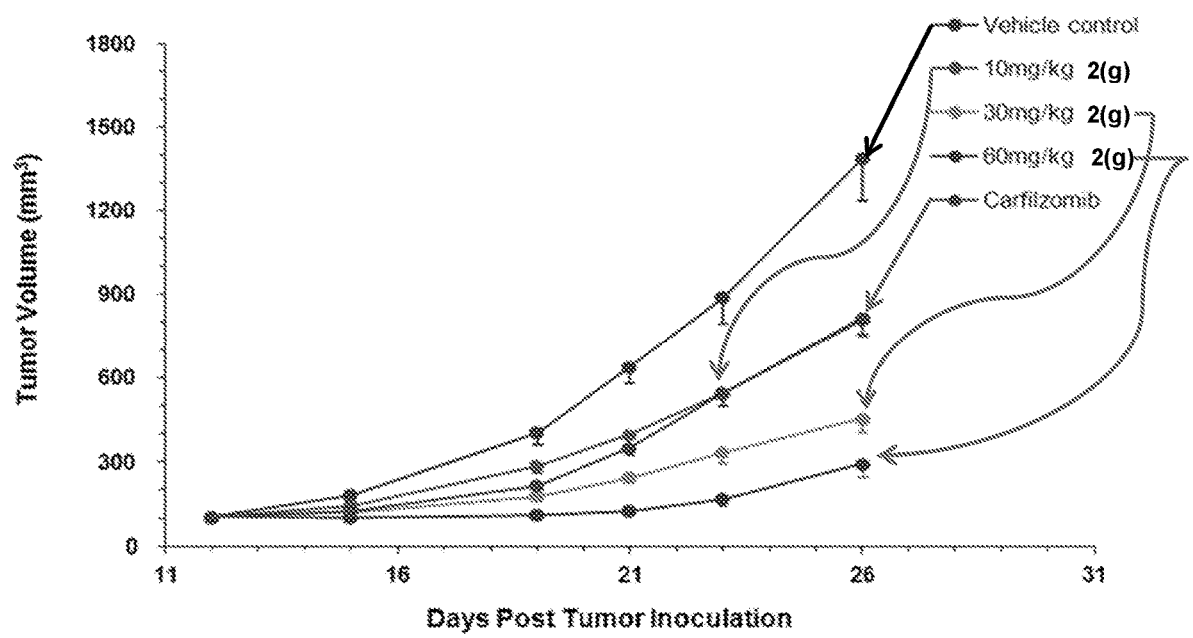

FLUORINATED IMIDAZO[4,5-C]QUINOLINE DERIVATIVES AS INHIBITORS OF BROMODOMAIN CONTAINING PROTEINS

CROSS-REFERENCE TO RELATED APPLICATIONS

The present application is a divisional of copending U.S. patent application Ser. No. 15/546,324, filed Jul. 26, 2017, which is a National Stage of International Application No. PCT/CA2016/050097, filed Feb. 3, 2016, which claims the benefit of priority from U.S. provisional patent application Ser. No. 62/111,251 filed on Feb. 3, 2015, the contents of each of which are incorporated herein by reference.

FIELD

The present application relates to novel fluorinated derivatives, to processes for their preparation, to compositions comprising them, and to their use in therapy. More particularly, it relates to compounds useful in the treatment of diseases, disorders or conditions mediated by Bromodomain-Containing Proteins.

BACKGROUND

Acetylation of lysine residues is a widespread protein post-translational modification (PTM), and extensively relevant to modulation of cellular processes, including protein conformation and interaction (*Science.* 2009 325: 834-840). Histone lysine acetylation was historically proposed to be a hallmark of transcriptionally active genes (*Bioessays.* 1998; 20:615-626), and hitherto, deregulation of histone acetylation patterns often drives the aberrant expression of oncogenes resulting in proliferation and tumorigenesis (*Curr Opin Struct Biol.* 2011 21: 735-743). Three types of proteins have been identified to regulate lysine acetylation: bromodomain (BRD) proteins (*Nat Rev Drug Discov.* 2014 13: 337-356), histone acetyltransferases (HATs), histone deacetylases (HDACs) and sirtuins (SIRTs) (*Cell Death Dis.* 2014 5: e1047). BRD proteins bind to acetylated lysine (Kac) and thus acting as readers of lysine acetylation state; HATs effect lysine acetylation acting as writers; HDACs and SIRTs remove acetyl groups as erasers (*Cell.* 2013 154: 569-582). Bromodomains, functioning as acetyl-lysine binding domains, belong to a family of evolutionarily conserved protein modules originally found in proteins associated with chromatin and in nearly all nuclear HATs (*Biochim Biophys Acta.* 2014 8:676-685). BRDs may contribute to highly specific histone acetylation by tethering transcriptional HATs to specific chromosomal sites, or to the activity of multi-protein complexes in chromatin remodeling. Thus, BRDs modulate enzyme activities, protein assembly and protein-protein interactions (PPIs) via lysine acetylation, revealing broad implications for the mechanisms underlying a wide variety of cellular events, such as transcriptional activation and chromatin remodeling.

Human genome encodes 61 BRDs in 46 different proteins, in which legend specificity is imparted in the amino acid residue differences around the acetyllysine binding site (*FEBS Lett.* 2012 586: 2692-2704). BRD proteins mostly contain one or two bromodomains, while some proteins, suchm as nuclear scaffolding proteins (PB1), contain more than two BRDs (*Cell.* 2013 153: 320-334). Bromodomain and extra-terminal (BET), which taxonomically belongs to human BRD proteins family, shares a common domain architecture comprising two N-terminal bromodomains and an extra-C terminal domain.

Bromodomains are small (about 110 amino acid) distinct domains within proteins that bind to acetylated lysine resides commonly but not exclusively in the context of histones. There is a family of around 50 proteins known to contain bromodomains, and they have a range of functions within the cell. The BET (bromodomain and extra-terminal) family of bromodomain containing proteins comprises 4 proteins (BRD2, BRD3, BRD4 and BRD-T) which contain tandem bromo domains capable of binding to two acetylated lysine residues in close proximity, increasing the specificity of the interaction. Recent research has established a compelling rationale for targeting BRD4 in cancer. BRD4 remains bound to transcriptional start sites of genes expressed during the entry into the G 1 phase of the cell cycle, and is functioning to recruit the positive transcription elongation factor complex (P-TEFb), resulting in increased expression of growth promoting genes (*Mol. Cell. Biol.* 2008 28, 967).

Except BRDT specially locating in testis, BET proteins are widely distributed, and exert function to regulate an array of cellular processes. Firstly detected as protein scaffolds, BET family proteins recruit variety proteins to chromatin and transcription sites. During interphase, BRD4 recruits positive transcriptional elongation factor complex (PTEFb) to sites of active transcription, while another pool of BRD4 may be recruited by transcription mediator complexes independent of PTEFb (*J Biol Chem.* 2007 13141-13145). In addition, the ET domain of BRD4 independently recruits transcription-modifying factors, including glioma tumor suppressor candidate region gene 1 (GLTSCR1); NSD3, a SET domain-containing histone methyltransferase; JMJD6, a histone arginine demethylase; and CHD4, a catalytic component of the NuRD nucleosome remodeling complex.

BET family may also function as mitotic bookmark, identifying actively transcribed genes during mitosis by remaining associated chromatin when all the other factors dissociate. BRD4 remains associated with H4K5ac histones on chromatin during mitosis, leading to rapid de-compaction of the surrounding chromatin and to transcription post-mitotically [*Transcription.* 2013 4 1: 13-17). BRD4 marks the start sites of many M/G1 genes, and accelerates expression of G1 genes and promotes cell cycle progression to S phase (*Nat Cell Biol.* 2011; 13:1295-1304). BRD4 seems to be required for the G2 to M phase transition of the cell cycle because microinjection of BRD4-specific antibodies leads to cell cycle arrest. Then, BET family proteins function as cell cycle regulators, as mentioned before, that key transcriptional regulators genes of S phase, E2F1 and E2F2, are associated with BRD2 multi-protein complexes. BRD3-dependent functional relationships with the cell cycle control machinery in normal cells are poorly understood, although forced expression of BRD3 down-regulates the RB-E2F pathway in nasopharyngeal carcinoma cells (*Nature Reviews Cancer* 2012, 12, 7: 465-477).

Importantly, BRD4 has been identified as a component of a recurrent t(15;19) chromosomal translocation in an aggressive form of human squamous carcinoma (*Cancer Res.* 2003 63, 304). Such translocations express the tandem N-terminal bromo domains of BRD4 as an in-frame chimera with the NUT (nuclear protein in testis) protein, genetically defining the so-called NUT midline carcinoma (NMC). Functional studies in patient-derived NMC cell lines have validated the essential role of the BRD4-NUT oncoprotein in maintaining the proliferation and the differentiation block of these malignant cells. In addition, BRD4 has been identified as a critical sensitivity determinant in a genetically defined AML mouse model (*Nature* 2011 478(7370):524-8). Suppression of BRD4 led to robust anti-leukemic effects in vitro and in vivo, accompanied by terminal myeloid differentiation. Interestingly, BRD4 inhibition triggered MYC down-regulation in a broad array of mouse and human leukemia cell lines examined, indicating that small molecule BRD4 inhibitors may provide a means to suppress the MYC pathway in a range of AML subtypes. Finally, the other family members of the BET family have also been reported to have some function in controlling or executing aspects of the cell cycle, and have been shown to remain in complex with chromosomes during cell division-suggesting a role in the maintenance of epigenetic memory (*Mol. Cell.* 2008 30 (1):51-60).

Recent studies indicated that BRD4 expression was upregulated in clinical urothelial carcinoma of the bladder (UCB) tissues, and high expression of BRD4 was associated closely with a more malignant clinical feature and poor prognosis of UCB patients. These results suggested that BRD4 over-expression might be useful as a prognostic factor for UCB patients and that BRD4 inhibition could be a new approach for effective therapy of human UCB (*Int J Clin Exp Pathol.* 2014; 7(7): 4231-4238).

In the activated B-cell-like (ABC) subtype of diffuse large B-cell lymphoma (DLBCL), NF-κB activity is essential for viability of the malignant cells and is sustained by constitutive activity of IκB kinase (IKK) in the cytoplasm. An unexpected role for the bromodomain and extraterminal domain (BET) proteins BRD2 and BRD4 in maintaining oncogenic IKK activity in ABC DLBCL has been reported (*Proc Natl Acad Sci USA.* 2014; 111(31):11365-70). IKK activity was reduced by small molecules targeting BET proteins as well as by genetic knockdown of BRD2 and BRD4 expression, thereby inhibiting downstream NF-κB-driven transcriptional programs and killing ABC DLBCL cells. Using a high-throughput platform to screen for drug-drug synergy, it was observed that the BET inhibitor JQ1 combined favorably with multiple drugs targeting B-cell receptor signaling, one pathway that activates IKK in ABC DLBCL.

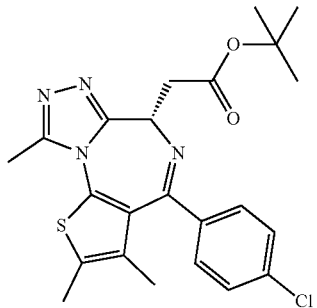

JQ1

The BTK kinase inhibitor ibrutinib, which is in clinical development for the treatment of ABC DLBCL, synergized strongly with BET inhibitors in killing ABC DLBCL cells in vitro and in a xenograft mouse model. These findings provide a mechanistic basis for the clinical development of BET protein inhibitors in ABC DLBCL, particularly in combination with other modulators of oncogenic IKK signaling.

Histone acetylation levels have been associated with an open chromatin architecture and transcriptional activation, but specific marks have been linked to chromatin condensation, regulation of metabolism and DNA repair. Therefore, inappropriate acetylation levels have been associated with an aberrant transcription of disease-promoting genes, including cancer-related genes (*Oncotarget.* 2015; 6(8): 5501-5506).

BET family proteins have been also reported to be involved in a variety of malignant tumors, between which NUT-NMC have been reported to closely related to BRD proteins, in which the BRD-NUT blocks cellular differentiation, and depletion of this oncogene in squamous differentiation and cell cycle arrest. NUT midline carcinoma (NMC), an aggressive squamous cell carcinoma, is accordance with acquired chromosomal rearrangements involving NUT, creating chimeric genes that encode fusion proteins. Usually BRD4-NUT fusion genes are been detected, and less commonly NUT-variant fusion genes involving BRD3 also exists, leading to the expression of BRD-NUT fusion proteins (*Expert Rev Mol Med.* 2011; 13: e29).

In addition, BET family proteins have reported to able to promote aberrant gene expression in leukemia. MYC family transcription factors are key regulators of cell growth and survival, whose gene amplification is a common copy-number alteration in cancer, while overexpression or translocation of the MYC locus contributes to Myc activity deregulation. In hematologic cancer models, such as MLL-fusion leukemia [46], acute myeloid leukemia (AML) (*Nature* 2011; 478: 524-528), Burkitt's lymphoma (*Proc. Natl. Acad. Sci. USA* 2011; 108: 16669-16674), multiple myeloma (*Cell.* 2011; 146: 904-917), and B-cell acute lymphoblastic (BLL) leukemia (*Blood.* 2012; 120:2843-2852), amplification of onco-protein Myc drivesm distinct transcription programs, and leads to a consequence of cell proliferation. BET family directly regulate the expression of MYC genes, and directly silencing MYC gene expression via disruption of BET protein binding at the MYC locus may largely reduce cell proliferation (*Nature* 2010; 463: 899-905).

Androgen receptor (AR) signalling is typically reactivated in patients with castration-resistant prostate cancer (CRPC). However, acquired resistance to therapies that target AR signalling often occurs, so there is a need to identify additional therapeutic targets within this signalling network. Studies have found that the bromodomain and extraterminal (BET) family of chromatin readers might be one such target. Treatment of a panel of prostate cancer cell lines with the small molecule BET inhibitor JQ1 revealed that those with activated AR signaling were sensitive to JQ1-induced apoptosis and cell cycle arrest, and this was phenocopied by knockdown of bromodomain-containing protein 2 (BRD2), BRD3 or BRD4, which are all BET family proteins. JQ1 also globally reduced the levels of transcription of AR target genes in AR-positive cells, which suggests that BET family proteins are involved in AR-mediated transcriptional programmes.

Interestingly, in prostate cell lines, which have both AR amplification and the transmembrane protease, serine 2 (TMPRSS2)-ETS-related gene (ERG) fusion gene, the expression of ERG and the ERG transcriptional programme were blocked by bromodomain inhibition through the reduction of AR and BRD4 binding to the TMPRSS2 promoter/enhancer.

Evidence suggests that JQ1 functions downstream of AR, therefore it may be effective in the context of acquired resistance mediated by AR activation (for example, by AR amplification or mutation), which is common in patients with CRPC (*Nature* 2014; 510(7504):278-82).

In another study, BRD2 and BRD4 RNA were found to be significantly overexpressed in Glioblastoma Multiforme (GBM), suggesting that BET protein inhibition may be an effective means of reducing GBM cell proliferation. Disruption of BRD4 expression in glioblastoma cells reduced cell cycle progression. Similarly, treatment with the BET protein inhibitor I-BET151 reduced GBM cell proliferation in vitro and in vivo. BET inhibition treatment enriched cells at the G1/S cell cycle transition. Importantly, BET inhibitors were as potent at inhibiting GBM cell proliferation as temozolomide (TMZ), the current chemotherapy treatment administered to GBM patients. Since BET inhibitors inhibit GBM cell proliferation by arresting cell cycle progression, suggests that BET protein inhibition as a viable therapeutic option for GBM patients suffering from TMZ resistant tumors (*Epigenetics.* 2014; 9(4):611-20).

Recent studies have unraveled a possible mechanism about how BRD4 proteins are involved in the transcription of active genes in cancers, especially associated with a subset of these genes. As previous mentioned, BRD4 and Mediator form a complex in transcription process, this complex may related to super-enhancers, which are span large genomic regions and contain exceptional amounts of Mediator and BRD4 (*Oncotarget.* 2015; 6(8): 5501-5506).

In addition, important tumor genes are also associated with super-enhancers, so far has been identified in myeloma, small-cell lung cancer and glioblastoma. Therefore, BRD4 may regulate ongenetic drivers, such as MYC, through occupying super-enhancers, while inhibition of BRD4 also leads to preferential disruption of super-enhancers and selective loss of oncogene expression (*Cell.* 2013; 153(2): 320-334).

Furthermore, Cancers of neural origin may be related to the distinct expression of BET proteins including glioblastoma, medulloblastoma, and neuroblastoma. For instance, neuroblastoma is a pediatric solid tumor associated with a high frequency of MYCN amplifications, and inhibition of BET proteins in neuroblastoma leads to cell arrest (*Cancer Discov.* 2013; 3:308-323). BET proteins are also required for glioblastoma cell proliferation, mRNA of BRD2 and BRD4 are significantly overexpressed in glioblastoma, while disruption of BRD4 expression reduced glioblastoma cell cycle progression (*Epigenetics.* 2014; 9: 611-620).

Also, in melanoma, tumor progression may contribute to epigenetic changes, thus epigenetic and/or transcriptional regulation of certain target genes may support melanoma tumor-genesis. NF-κB regulates cytokine and chemokine production in melanoma, and is believed to contribute to progression of the disease by up-regulation of cell cycle and anti-apoptotic genes. BRD2 and BRD4 are overexpressed in human primary and metastatic melanomas, whose inhibition resulted in down-regulating production of cytokines such as IL-6 and IL-8 (*Ann Rheum Dis.* 2014; pii: annrheumdis-2014-205809).

Furthermore, the largely hydrophobic nature of the central acetylated lysine binding pocket and special extra-terminal domain of BET are necessary to accommodate the charge neutralized acetylated lysine and recruits related proteins, making these modules particularly attractive for the development of inhibitors. Many proteins that use BRDs for their recruitment to specific regulatory complexes have been implicated in the development of cancer (*Nature Reviews Drug Discovery,* 2014, 13(5): 337-356).

Studies on the transcriptional effects of BET inhibitors demonstrated that the inhibition of BET bromodomains selectively interfered with gene expression programmes that mediated cellular growth and evasion of apoptosis in cancers. Given the general role of BET proteins in transcriptional elongation, the discovery that inhibition of these proteins only affects the transcription of a small subset of genes was unexpected and suggested that inhibitors of bromodomains may specifically modulate the expression of some disease-promoting genes. Examples of bromo domain inhibitors include benzodiazepine derivatives, disclosed in WO2011/054553, and imidazo quinolone derivatives, disclosed in WO20111054846. Thus, there is the need to provide BRD inhibitors and especially BRD4 inhibitors for use in the prevention and/or treatment of diseases characterized by excessive or abnormal cell proliferation, such as cancer.

Although much attention has been focused on the oncologic applications of the bromodomain inhibitors, bromodomain inhibitors have shown inhibition against T-cell mediated inflammation in a rat model at a level comparable to that of the positive control compound, rapamycin.

In addition some viruses make use of BET proteins to tether their genomes to the host cell chromatin, as part of the process of viral replication (*Cell* 2004 117(3):349-60). Therefore, BET inhibition may have a broad range of therapeutic applications beyond oncology, such as inflammation, heart failure, and male contraception [*Cell* 2013, 154 (3), 569-582; *Cell* 2012, 150 (4), 673-684].

Fluorine has found interest in bioorganic and structural chemistry over the past decade and has become a useful feature in small molecule drug design. The small and highly electronegative fluorine atom can play a useful role in medicinal chemistry. Selective installation of fluorine into a therapeutic or diagnostic small molecule candidate can provide a number of favorable pharmacokinetic and/or physicochemical properties including improved metabolic stability and enhanced membrane permeation. Increased binding affinity of fluorinated drug candidates to a target protein has also been documented in some cases. A further emerging application of the fluorine atom is the use of $^{18}$F isotope as a radiolabel tracer atom in the sensitive technique of Positron Emission Tomography (PET) imaging.

Fluorine substitution has been investigated in drug research as a means of enhancing biological activity and/or increasing chemical and/or metabolic stability. Factors to be considered when synthesising fluorine-containing compounds include (a) the relatively small size of the fluorine atom (van der Waals radius of 1.47 Å), comparable to hydrogen (van der Waals radius of 1.20 Å), (b) the highly electron-withdrawing nature of fluorine, (c) the greater stability of the C—F bond compared to the C—H bond, and (d) the greater lipophilicity of fluorine compared to hydrogen.

Despite the fact that fluorine is slightly larger than hydrogen, several studies have shown that the fluorine atom is a reasonable hydrogen mimic with minimal steric perturbations with respect to the compound's mode of binding to a receptor or enzyme (*Annu. Rev. Pharmacol. Toxicol.* 2001, 41, 443-470). However, the introduction of a fluorine atom can significantly alter the physicochemical properties of a compound due to its high electronegativity. Therefore, this type of modification can potentially induce altered biological responses of the molecule.

SUMMARY

A novel class of fluorinated derivatives of Formula I have been prepared and found to be useful in the treatment of cancers and other Bromodomain-Containing Protein-related disorders.

Accordingly, one aspect of the present application includes a compound of Formula I or a pharmaceutically acceptable salt, solvate and/or prodrug thereof:

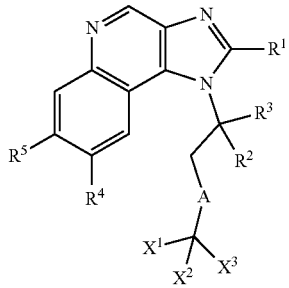

Formula I wherein:
R$^1$ is selected from H, optionally substituted C$_{1-20}$alkyl, optionally substituted C$_{2-20}$alkenyl, optionally substituted C$_{3-20}$cycloalkyl, optionally substituted C$_{6-20}$aryl, optionally substituted heterocycloalkyl, optionally substituted heteroaryl, optionally substituted C$_{1-6}$alkyleneC$_{3-10}$ ocycloalkyl, optionally substituted C$_{1-6}$alkylenearyl, optionally substituted C$_{1-6}$alkyleneheterocycloalkyl, optionally substituted C$_{1-6}$alkyleneheteroaryl, OR$^6$, CN, COOR$^6$, CONR$^6$R$^7$, C$_{1-6}$alkyleneOR$^6$, C$_{1-6}$alkyleneCOOR$^6$, NR$^6$R$^7$, C$_{1-6}$alkyleneNR$^6$R$^7$, C$_{1-6}$alkyleneCONR$^6$R$^7$, C$_{1-6}$alkyleneNCOR$^6$, C$_{1-6}$alkyleneCSNR$^6$R$^7$ SR$^6$, C$_{1-6}$alkyleneSR$^6$, SOR$^6$, C$_{1-6}$alkyleneSOR$^6$, SO$_2$R$^6$ and C$_{1-6}$alkyleneSO$_2$R$^6$;
R$^2$ and R$^3$ are independently selected from H, fluoro, and C$_{1-6}$alkyl, C$_{1-6}$alkylOR$^6$, C$_{1-6}$alkylCOOR$^6$, C$_{1-6}$alkylCONR$^6$R$^7$, C$_{1-6}$alkylSR$^6$, C$_{1-6}$alkylSOR$^6$, C$_{1-6}$alkylSO$_2$R$^6$, C$_{1-6}$alkylNR$^6$R$^7$, C$_{1-6}$alkylNCOR$^6$ or
R$^2$ and R$^3$ together form an oxo (=O) group, or
R$^2$ and R$^3$, together with the carbon atom to which they are attached, form C$_{3-7}$cycloalkyl or C$_{3-7}$heterocycloalkyl;
R$^4$ is selected from H, optionally substituted C$_{1-20}$alkyl, optionally substituted C$_{2-20}$alkenyl, optionally substituted C$_{3-20}$cycloalkyl, optionally substituted C$_{6-20}$aryl, optionally substituted heterocycloalkyl, optionally substituted heteroaryl, optionally substituted C$_{1-6}$alkyleneC$_{3-10}$ ocycloalkyl, optionally substituted C$_{1-6}$alkylenearyl, optionally substituted C$_{1-6}$alkyleneheterocycloalkyl, optionally substituted C$_{1-6}$alkyleneheteroaryl, OR$^6$, CN, COOH, COOR$^6$, COONH$_2$, COONR$^6$R$^7$, C$_{1-6}$alkyleneOR$^6$, NR$^6$R$^7$, C$_{1-6}$alkyleneNR$^6$R$^7$ C$_{1-6}$alkyleneCONR$^6$R$^7$, SR$^6$, CN, C$_{1-6}$alkyleneOR$^6$, NR$^6$R$^7$, C$_{1-6}$alkyleneNCOR$^6$ and halogen;
R$^5$ is selected from H, optionally substituted monocyclic rings having 0-3 heteroatoms independently selected from N, O and S and the optional substituents are selected from 1 to 3 C$_{1-6}$alkyl and C$_{1-6}$alkoxy, optionally substituted C$_{1-20}$alkyl, optionally substituted C$_{2-20}$alkenyl, optionally substituted C$_{3-20}$cycloalkyl, optionally substituted C$_{6-20}$aryl, optionally substituted heterocycloalkyl, optionally substituted heteroaryl, optionally substituted C$_{1-6}$alkyleneC$_{3-10}$cycloalkyl, optionally substituted C$_{1-6}$alkylenearyl, optionally substituted C$_{1-6}$alkyleneheterocycloalkyl, optionally substituted C$_{1-6}$alkyleneheteroaryl, OR$^6$, —CN, COOR$^6$, CONR$^6$R$^7$, C$_{1-6}$alkyleneOR$^6$, C$_{1-6}$alkyleneCOOR$^6$, NR$^6$R$^7$ and C$_{1-6}$alkyleneNR$^6$R$^7$, C$_{1-6}$alkyleneCONR$^6$R$^7$, C$_{1-6}$alkyleneNCOR$^6$ C$_{1-6}$alkyleneCSNR$^6$R$^7$ SR$^6$, C$_{1-6}$alkyleneSR$^6$, SOR$^6$, C$_{1-6}$alkyleneSOR$^6$, SO$_2$R$^6$, C$_{1-6}$alkyleneSO$_2$R$^6$;

R$^6$ and R$^7$ are each independently selected from H, C$_{1-6}$alkyl, C$_{3-10}$cycloalkyl, heterocycloalkyl and haloC$_{1-6}$alkyl;
A is selected from C$_{0-6}$alkylene, O, S, SO, SO$_2$ and NR$^6$;
X$^1$, X$^2$ and X$^3$ are the same or different and are selected from H, halogen, and C$_{1-6}$alkyl, provided that at least one of X$^1$, X$^2$ and X$^3$ is F; and
one or more of the atoms in the compounds of Formula I are optionally replaced with a radioactive isotope thereof.

In an embodiment, the application includes a compound of Formula Ia or a pharmaceutically acceptable salt, solvate or prodrug thereof:

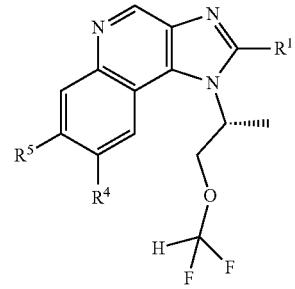

Formula Ia wherein
R$^1$ is H, optionally substituted alkyl, optionally substituted alkenyl, optionally substituted cycloalkyl, optionally substituted aryl, optionally substituted heterocycloalkyl, optionally substituted heteroaryl, optionally substituted —CH$_2$-cycloalkyl, optionally substituted —CH$_2$-aryl, optionally substituted —CH$_2$-heterocycloalkyl, optionally substituted —CH$_2$-heteroaryl, optionally substituted —CH(C$_1$-C$_6$-alkyl)-alkyl, optionally substituted —CH(C$_1$-C$_6$-alkyl)cycloalkyl, optionally substituted —CH(C$_1$-C$_6$-alkyl)-aryl, optionally substituted —CH(C$_1$-C$_6$-alkyl)-heterocycloalkyl, or optionally substituted —CH(C$_1$-C$_6$-alkyl)-heteroaryl; OR$_6$, —CN, —CH$_2$OR$_6$, —NH-alkyl, —N(alkyl)$_2$', —CH$_2$N(alkyl)$_2$, —CH$_2$NH(alkyl);
R$^4$ is OR$^6$, —CN, —CH$_2$OR$^6$, —NH-alkyl, —N(alkyl)$_2$', —CH$_2$N(alkyl)$_2$, —CH$_2$NH(alkyl), or halogen;
R$^5$ is an optionally substituted monocyclic ring having 1-3 heteroatoms independently selected from N and O; wherein the optional substituent is alkyl; and
R$^6$ are each independently H, C$_1$-C$_6$ alkyl, cycloalkyl, or haloalkyl.

In an embodiment, the application includes a compound of Formula Ib or a pharmaceutically acceptable salt, solvate or prodrug thereof:

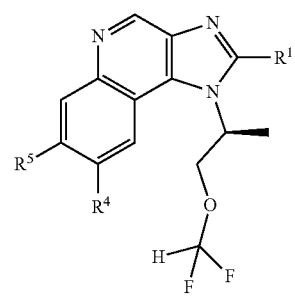

Formula Ib wherein

R[1] is H, optionally substituted alkyl, optionally substituted alkenyl, optionally substituted cycloalkyl, optionally substituted aryl, optionally substituted heterocycloalkyl, optionally substituted heteroaryl, optionally substituted —$CH_2$-cycloalkyl, optionally substituted —$CH_2$-aryl, optionally substituted —$CH_2$-heterocycloalkyl, optionally substituted —$CH_2$-heteroaryl, optionally substituted —$CH(C_1$-$C_6$-alkyl)-alkyl, optionally substituted —$CH(C_1$-$C_6$-alkyl)cycloalkyl, optionally substituted —$CH(C_1$-$C_6$-alkyl)-aryl, optionally substituted —$CH(C_1$-$C_6$-alkyl)-heterocycloalkyl, or optionally substituted —$CH(C_1$-$C_6$-alkyl)-heteroaryl; $OR_6$, —CN, —$CH_2OR_6$, —NH-alkyl, —N(alkyl)$_2$', —$CH_2N$(alkyl)$_2$, —$CH_2NH$(alkyl);

R[4] is $OR^6$, —CN, —$CH_2OR^6$, —NH-alkyl, —N(alkyl)$_2$', —$CH_2N$(alkyl)$_2$, —$CH_2NH$(alkyl), or halogen;

R[5] is an optionally substituted monocyclic ring having 1-3 heteroatoms independently selected from N and O; wherein the optional substituent is alkyl; and R[6] are each independently H, $C_1$-$C_6$ alkyl, cycloalkyl, or haloalkyl.

The present application also includes a composition comprising one or more compounds of the application and a carrier. In an embodiment, the composition is a pharmaceutical composition comprising one or more compounds of the application and a pharmaceutically acceptable carrier.

The compounds of the application have been shown to be capable of inhibiting BET family protein function. Therefore the compounds of the application are useful for treating diseases, disorders or conditions mediated by one or more BET family proteins, as a result of its over-expression, or its variation in terms of protein sequence or post-translational modification. Accordingly, the present application also includes a method of treating a disease, disorder or condition mediated by or through a BET family protein comprising administering a therapeutically effective amount of one or more compounds of the application to a subject in need thereof.

In a further embodiment, the compounds of the application are used as medicaments. Accordingly, the application also includes a compound of the application for use as a medicament.

The present application also includes a method of treating a disease, disorder or condition treatable by BET family protein inhibition comprising administering a therapeutically effective amount of one or more compounds of the application to a subject in need thereof. The present application also includes a use of one or more compounds of the application for treatment of a disease, disorder or condition treatable by BET family protein inhibition as well as a use of one or more compounds of the application for the preparation of a medicament for treatment of a disease, disorder or condition treatable by BET family protein inhibition. The application further includes one or more compounds of the application for use in treating a disease, disorder or condition treatable by BET family protein inhibition.

In an embodiment, the disease, disorder or condition mediated by BET family protein or treatable by BET family protein inhibition is a neoplastic disorder. In an embodiment, the treatment is in an amount effective to ameliorate at least one symptom of the neoplastic disorder, for example, reduced cell proliferation or reduced tumor mass, volume or distribution in a subject in need of such treatment.

In an embodiment, the disease, disorder or condition mediated by a BET family protein, or treatable by BET family protein inhibition, is cancer.

In an embodiment, the disease, disorder or condition mediated by BET family protein, or treatable by BET family protein inhibition, is a disease, disorder or condition associated with an uncontrolled and/or abnormal cellular activity affected or effected directly or indirectly by a inhibition of a BET family protein. In another embodiment, the uncontrolled and/or abnormal cellular activity that is affected directly or indirectly by inhibition of a BET family protein is proliferative activity in a cell.

The application also includes a method of inhibiting proliferative activity in a cell, comprising administering or delivering an effective amount of one or more compounds of the application to the cell.

In a further embodiment the disease, disorder or condition mediated by a BET family protein, or treatable by BET family protein inhibition, is cancer and the one or more compounds of the application are administered in combination with one or more additional cancer treatments. In another embodiment, the additional cancer treatment is selected from radiotherapy, chemotherapy, targeted therapies, such as antibody therapies, and small molecule therapies, such as tyrosine-kinase inhibitors, immunotherapy, hormonal therapy and anti-angiogenic therapies. In other embodiments, the present compounds are useful medically across the broad range of medical conditions that are connected with the numerous pathways regulated in full or in part by the BET bromodomains including BRD2, BRD3 and particularly BRD4. These medical conditions include inflammation in its various forms, as well as viral infection such as HIV infection, and metabolic disorders that include obesity and the like.

The application additionally provides a process for the preparation of compounds of the application. General and specific processes are discussed in more detail below and set forth in the Examples below.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The application will be described in greater detail with reference to the drawing in which:

FIG. 1 is a graph showing the therapeutic efficacy and tolerance of exemplary compound 2(g) in a MM.1S subcutaneous human multiple myeloma xenograft model.

DETAILED DESCRIPTION

I. Definitions

Unless otherwise indicated, the definitions and embodiments described in this and other sections are intended to be applicable to all embodiments and aspects of the application herein described for which they are suitable as would be understood by a person skilled in the art. Unless otherwise specified within this application or unless a person skilled in the art would understand otherwise, the nomenclature used in this application generally follows the examples and rules stated in "Nomenclature of Organic Chemistry" (Pergamon Press, 1979), Sections A, B, C, D, E, F, and H. Optionally, a name of a compound may be generated using a chemical naming program such as ACD/ChemSketch, Version 5.09/ September 2001, Advanced Chemistry Development, Inc., Toronto, Canada.

The term "compound of the application" or "compound of the present application" and the like as used herein refers to a compound of Formula I, Ia, Ib or Ic, or pharmaceutically acceptable salts, solvates, prodrugs and/or radiolabeled versions thereof.

The term "composition of the application" or "composition of the present application" and the like as used herein refers to a composition, such as a pharmaceutical composition, comprising one or more compounds of Formula I and/or Ia, or pharmaceutically acceptable salts, solvates, prodrugs and/or radiolabeled versions thereof.

The term "and/or" as used herein means that the listed items are present, or used, individually or in combination. In effect, this term means that "at least one of" or "one or more" of the listed items is used or present. The term "and/or" with respect to pharmaceutically acceptable salts, solvates and/or prodrugs thereof means that the compounds of the application exist as individual salts, hydrates or prodrugs, as well as a combination of, for example, a salt of a solvate of a compound of the application or a salt of a prodrug of a compound of a compound of the invention.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present application, the term "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements, or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of" as used herein is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-20}$alkyl means an alkyl group having 1, 2, 3, 4, 5, 6, 7, 8, 9, 10, 11, 12, 13, 14, 15, 16, 17, 18, 19 or 20 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{0-6}$alkylene means an alkylene group is not present ("$C_0$alkylene") or an alkylene group having 1, 2, 3, 4, 5 or 6 carbon atoms.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond.

The term "haloalkyl" as used herein refers to an alkyl group wherein one or more, including all of the hydrogen atoms are replaced by a halogen atom. In an embodiment, the halogen is fluorine, in which case the haloalkyl is referred to herein as a "fluoroalkyl" group. In another embodiment, the haloalkyl comprises at least one —$CHF_2$ group.

The term "alkoxy" as used herein, whether it is used alone or as part of another group, refers to the group "alkyl-O—" or "—O-alkyl". The term $C_{1-10}$alkoxy means an alkyl group having 1, 2, 3, 4, 5, 6, 7, 8, 9 or 10 carbon atoms bonded to an oxygen atom. Exemplary alkoxy groups include without limitation methoxy, ethoxy, propoxy, isopropoxy, butoxy, t-butoxy and isobutoxy.

The term "cycloalkyl," as used herein, whether it is used alone or as part of another group, means a saturated carbocyclic group containing a number of carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to cyclic groups containing from 6 to 20 carbon atoms and at least one aromatic ring. In an embodiment of the application, the aryl group contains from 6, 9 or 10 carbon atoms, such as phenyl, indanyl or naphthyl.

The term "heterocycloalkyl" as used herein, whether it is used alone or as part of another group, refers to cyclic groups containing 3 to 20 atoms, suitably 3 to 10 atoms, and at least one non-aromatic, ring in which one or more of the atoms are a heteromoiety selected from O, S, N, NH and $NC_{1-6}$alkyl. Heterocycloalkyl groups are either saturated or unsaturated (i.e. contain one or more double bonds) and contain one or more than one ring (i.e. are polycyclic). When a heterocycloalkyl group contains more than one ring, the rings may be fused, bridged, spirofused or linked by a bond. When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteromoiety as defined above.

A first ring group being "fused" with a second ring group means the first ring and the second ring share at least two atoms there between.

The term "heteroaryl" as used herein refers to cyclic groups containing from 5 to 20 atoms, suitably 5 to 10 atoms, at least one aromatic ring and at least one a heteromoiety selected from O, S, N, NH and $NC_{1-6}$alkyl. Heteroaryl groups contain one or more than one ring (i.e. are polycyclic). When a heteroaryl group contains more than one ring, the rings may be fused, bridged, spirofused or linked by a bond. When a heteroaryl group contains the prefix $C_{n1-n2}$ this prefix indicates the number of carbon atoms in the corresponding carbocyclic group, in which one or more, suitably 1 to 5, of the ring atoms is replaced with a heteromoiety as defined above.

A five-membered heteroaryl is a heteroaryl with a ring having five ring atoms, wherein 1, 2 or 3 ring atoms are a heteromoiety selected from O, S, NH and $NC_{1-6}$alkyl. Exemplary five-membered heteroaryls include but are not limited to thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl is a heteroaryl with a ring having six ring atoms wherein 1, 2 or 3 ring atoms are a heteromoiety selected from O, S, NH and $NC_{1-6}$alkyl. Exemplary six-membered heteroaryls include but are not limited to pyridinyl, pyrazinyl, pyrimidinyl, triazinyl and pyridazinyl.

As a prefix, the term "substituted" as used herein refers to a structure, molecule or group in which one or more available hydrogen atoms are replaced with one or more other chemical groups. For example, substituted phenyl may refer to nitrophenyl, pyridylphenyl, methoxyphenyl, chlorophenyl, aminophenyl, etc., wherein the nitro, pyridyl, methoxy, chloro, and amino groups replace any available hydrogen on the phenyl ring.

As a suffix, the term "substituted" as used herein in relation to a first structure, molecule or group, followed by one or more variables or names of chemical groups, refers to a second structure, molecule or group that results from replacing one or more available hydrogens of the first structure, molecule or group with the one or more variables or named chemical groups. For example, a "phenyl substituted by nitro" refers to nitrophenyl.

The term "available", as in "available hydrogen atoms" or "available atoms" refers to atoms that would be known to a person skilled in the art to be capable of replacement by a substituent.

The term "optionally substituted" refers to groups, structures, or molecules that are either unsubstituted or are substituted with one or more substituents.

The term "amine" or "amino," as used herein, whether it is used alone or as part of another group, refers to groups of the general formula NRR', wherein R and R' are each independently selected from hydrogen or a an alkyl group, such as $C_{1-6}$alkyl.

The terms "halo" or "halogen" as used herein, whether it is used alone or as part of another group, refers to a halogen atom and includes fluoro, chloro, bromo and iodo.

The term acac as used herein refers to acetylacetonate.

The term "atm" as used herein refers to atmosphere.

The term "aq." as used herein refers to aqueous.

The terms "Boc" and "t-Boc" as used herein refer to the group tert-butoxycarbonyl.

DCM as used herein refers to dichloromethane.

DIPEA as used herein refers to N,N-diisopropyl ethylamine

DMF as used herein refers to dimethylformamide.

DMSO as used herein refers to dimethylsulfoxide.

EDCl.HCl as used herein refers to N-[3-(dimethylamino)propyl]-N'-ethylcarbodiimide hydrochloride.

EDC as used herein refers to 1-ethyl-3-(3-dimethylaminopropyl)carbodiimide.

$Et_2O$ as used herein refers to diethylether.

EtOAc as used herein refers to ethyl acetate.

Et as used herein refers to the group ethyl.

Fmoc as used herein refers to the group 9-fluorenylmethyloxycarbonyl.

The term "hr(s)" as used herein refers to hour(s).

The term "min(s)" as used herein refers to minute(s).

HOBt as used herein refers to N-hydroxybenzotriazole.

HBTU as used herein refers to O-(benzotriazol-1-yl)-N,N,N',N'-tetramethyluronium hexafluorophosphate.

MeOH as used herein refers to methanol.

Me as used herein refers to the group methyl.

t-BuLi as used herein refers to tert-butyllithium.

ON as used herein refers to overnight.

RT as used herein refers to room temperature.

TEA as used herein refers to triethylamine.

TFA as used herein refers to trifluoroacetic acid.

THF as used herein refers to tetrahydrofuran.

t-Bu as used herein refers to the group tertiary butyl.

SPE as used herein refers to solid phase extraction, for example using columns containing silica gel for mini-chromatography.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas).

The term "cell" as used herein refers to a single cell or a plurality of cells and includes a cell either in a cell culture or in a subject.

The term "subject" as used herein includes all members of the animal kingdom including mammals, and suitably refers to humans. Thus the methods of the present application are applicable to both human therapy and veterinary applications. In an embodiment, the subject is a mammal. In another embodiment, the subject is human.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," J. Pharm. Sci. 1977, 66, 1-19]. The selection of the appropriate salt may be useful, for example, so that an ester functionality, if any, elsewhere in a compound is not hydrolyzed. The selection criteria for the appropriate salt will be known to one skilled in the art.

In general, prodrugs will be functional derivatives of the compounds of the application which are readily convertible in vivo into the compound from which it is notionally derived. In an embodiment, prodrugs of the compounds of the application are conventional esters formed with the available hydroxy and/or amino group. For example, an available OH and/or $NH_2$ in the compounds of the application is acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the application are those in which the hydroxy and/or amino groups in the compounds are masked as groups which can be converted to hydroxy and/or amino groups in vivo. Conventional procedures for the selection and preparation of suitable prodrugs are described, for example, in "Design of Prodrugs" ed. H. Bundgaard, Elsevier, 1985.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations. For example, the compounds of the application are administered at least once a week. However, in another embodiment, the compounds are administered to the subject from about one time per two weeks, three weeks or one month. In another embodiment, the compounds are administered about one time per week to about once daily. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

"Palliating" a disease, disorder or condition means that the extent and/or undesirable clinical manifestations of a disease, disorder or condition are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The "disease, disorder or condition" as used herein refers to a disease, disorder or condition treatable by BET protein inhibition and particularly using a BET protein inhibitor, such as a compound of the application herein described.

The term "mediated by a BET protein" as used herein means that the disease, disorder or condition to be treated is affected by, modulated by and/or has some biological basis, either direct or indirect, that includes BET protein activity, in particular, increased BET protein activity such as results from BET/BRD gene overexpression or BET/BRD protein over-accumulation or over-expression of proteins that are products of or precursors to BET-mediated gene expression. In a refined context, "mediated by a BET protein" refers to an effect mediated through a BET protein domain, including BRD2, BRD3 and, particularly, BRD4. In a broader context, "mediated by a BET/BRD protein" can include the large number of diseases that are caused by aberrant acetylation of lysine residues, as results from aberrant BET and/or BRD protein activity. As used herein, BRD4 refers to the protein identified as 060885-1 in the UniProtKB database and isoforms that include the sequence of 06885-2, a shorter version. Similarly, the other BRD proteins are characterized and described in any of the protein databases.

As used herein, the term "effective amount" or "therapeutically effective amount" means an amount of one or more compounds of the application that is effective, at dosages and for periods of time necessary to achieve the desired result. For example in the context of treating a disease, disorder or condition mediated by a BET protein, an effective amount is an amount that, for example, increases BET protein inhibition compared to the inhibition without administration of the one or more compounds. In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective amount of one or more compounds or compositions of the application to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer). Exemplary neoplastic disorders include the so-called solid tumours and liquid tumours, including but not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers.

The term "cancer" as used herein refers to cellular-proliferative disease states.

II. Compounds and Compositions of the Application

Compounds of the present application were prepared and were found to inhibit uncontrolled and/or abnormal cellular activities affected directly or indirectly by BET family protein. In particular, compounds of the present application exhibited activity as BET inhibitors, and are therefore useful in therapy, for example for the treatment of neoplastic disorders such as cancer.

Accordingly, the present application includes a compound of Formula I or a pharmaceutically acceptable salt, solvate or prodrug thereof:

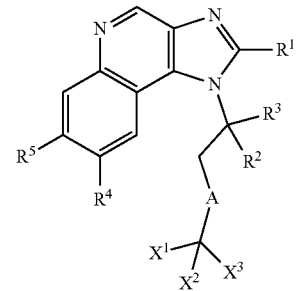

Formula I wherein:

$R^1$ is selected from H, optionally substituted $C_{1-20}$alkyl, optionally substituted $C_{2-20}$alkenyl, optionally substituted $C_{3-20}$cycloalkyl, optionally substituted $C_{6-20}$aryl, optionally substituted heterocycloalkyl, optionally substituted heteroaryl, optionally substituted $C_{1-6}$alkylene$C_{3-10}$cycloalkyl, optionally substituted $C_{1-6}$alkylenearyl, optionally substituted $C_{1-6}$alkyleneheterocycloalkyl, optionally substituted $C_{1-6}$alkyleneheteroaryl, $OR^6$, CN, $COOR^6$, $CONR^6R^7$, $C_{1-6}$alkyleneOR$^6$, $C_{1-6}$alkyleneCOOR$^6$, $NR^6R^7$, $C_{1-6}$alkyleneNR$^6R^7$, $C_{1-6}$alkyleneCONR$^6R^7$, $C_{1-6}$alkyleneNCOR$^6$, $C_{1-6}$alkyleneCSNR$^6R^7$ $SR^6$, $C_{1-6}$alkyleneSR$^6$, $SOR^6$, $C_{1-6}$alkyleneSOR$^6$, $SO_2R^6$ and $C_{1-6}$alkyleneSO$_2R^6$;

$R^2$ and $R^3$ are independently selected from H, fluoro, and $C_{1-6}$alkyl, $C_{1-6}$alkylOR$^6$, $C_{1-6}$alkylCOOR$^6$, $C_{1-6}$alkylCONR$^6R^7$, $C_{1-6}$alkylSR$^6$, $C_{1-6}$alkylSOR$^6$, $C_{1-6}$alkylSO$_2R^6$, $C_{1-6}$alkylNR$^6R^7$, $C_{1-6}$alkylNCOR$^6$ or $R^2$ and $R^3$ together form an oxo ($=$O) group, or $R^2$ and $R^3$, together with the carbon atom to which they are attached, form $C_{3-7}$cycloalkyl or $C_{3-7}$heterocycloalkyl;

$R^4$ is selected from H, optionally substituted $C_{1-20}$alkyl, optionally substituted $C_{2-20}$alkenyl, optionally substituted $C_{3-20}$cycloalkyl, optionally substituted $C_{6-20}$aryl, optionally substituted heterocycloalkyl, optionally substituted heteroaryl, optionally substituted $C_{1-6}$alkylene$C_{3-10}$ ocycloalkyl, optionally substituted $C_{1-6}$alkylenearyl, optionally substituted $C_{1-6}$alkyleneheterocycloalkyl, optionally substituted $C_{1-6}$alkyleneheteroaryl, $OR^6$, CN, COOH, $COOR^6$, $COONH_2$, $COONR^6R^7$, $C_{1-6}$alkyleneOR$^6$, $NR^6R^7$, $C_{1-6}$alkyleneNR$^6R^7$, $C_{1-6}$alkyleneCONR$^6R^7$, $SR^6$, CN, $C_{1-6}$alkyleneOR$^6$, $NR^6R^7$, $C_{1-6}$alkyleneNCOR$^6$ and halogen;

$R^5$ is selected from H, optionally substituted monocyclic rings having 0-3 heteroatoms independently selected from N, O and S and the optional substituents are selected from 1 to 3 $C_{1-6}$alkyl and $C_{1-6}$alkoxy, optionally substituted $C_{1-20}$alkyl, optionally substituted $C_{2-20}$alkenyl, optionally substituted $C_{3-20}$cycloalkyl, optionally substituted $C_{6-20}$aryl, optionally substituted heterocycloalkyl, optionally substituted heteroaryl, optionally substituted $C_{1-6}$alkylene$C_{3-10}$ ocycloalkyl, optionally substituted $C_{1-6}$alkylenearyl, optionally substituted $C_{1-6}$alkyleneheterocycloalkyl, optionally substituted $C_{1-6}$alkyleneheteroaryl, $OR^6$, —CN, $COOR^6$, $CONR^6R^7$, $C_{1-6}$alkyleneOR$^6$, $C_{1-6}$alkyleneCOOR$^6$, $NR^6R^7$ and $C_{1-6}$alkyleneNR$^6R^7$, $C_{1-6}$alkyleneCONR$^6R^7$, $C_{1-6}$alkyleneNCOR$^6$ $C_{1-6}$alkyleneCSNR$^6R^7$ $SR^6$, $C_{1-6}$alkyleneSR$^6$, $SOR^6$, $C_{1-6}$alkyleneSOR$^6$, $SO_2R^6$ and $C_{1-6}$alkyleneSO$_2R^6$;

$R^6$ and $R^7$ are each independently selected from H, $C_{1-6}$alkyl, $C_{3-10}$cycloalkyl, heterocycloalkyl and haloC$_{1-6}$alkyl;

A is selected from $C_{0-6}$alkylene, O, S, SO, $SO_2$ and $NR^6$;

$X^1$, $X^2$ and $X^3$ are the same or different and are selected from H, halogen, and $C_{1-6}$alkyl, provided that at least one of $X^1$, $X^2$ and $X^3$ is F; and one or more of the atoms in the compounds of Formula I are optionally replaced with a radioactive isotope thereof.

In an embodiment, $R^1$ is selected from optionally substituted $C_{1-10}$alkyl, optionally substituted $C_{2-10}$alkenyl, optionally substituted $C_{3-10}$cycloalkyl, optionally substituted $C_{6-10}$aryl, optionally substituted $C_{5-10}$heterocycloalkyl, optionally substituted $C_{5-10}$heteroaryl, optionally substituted $C_{1-4}$alkylene$C_{3-10}$cycloalkyl, optionally substituted $C_{1-4}$alkylene$C_{6-10}$aryl, optionally substituted $C_{1-4}$alkylene$C_{5-10}$heterocycloalkyl, optionally substituted $C_{1-4}$alkylene$C_{5-10}$heteroaryl, $OR^6$, CN, $C_{1-4}$alkyleneOR$^6$, $NR^6R^7$ and $C_{1-4}$alkyleneNR$^6R^7$.

In an embodiment, $R^1$ is selected from optionally substituted $C_{1-6}$alkyl, optionally substituted $C_{2-6}$alkenyl, optionally substituted $C_{3-6}$cycloalkyl, optionally substituted phenyl, optionally substituted $C_{5-6}$heterocycloalkyl, optionally substituted $C_{5-6}$heteroaryl, optionally substituted $C_{1-2}$alkylene$C_{3-6}$cycloalkyl, optionally substituted $C_{1-2}$alkylenephenyl, optionally substituted $C_{1-2}$alkylene$C_{5-6}$heterocycloalkyl, optionally substituted $C_{1-2}$alkylene$C_{5-6}$heteroaryl, $OR^6$, $C_{1-2}$alkyleneOR$^6$, $NR^6R^7$ and $C_{1-2}$alkyleneNR$^6R^7$.

In an embodiment, $R^1$ is selected from optionally substituted $C_{3-6}$cycloalkyl, optionally substituted $C_{5-6}$heterocycloalkyl, optionally substituted $C_{5-6}$heteroaryl, optionally substituted $CH_2C_{5-6}$cycloalkyl, optionally substituted $CH_2C_{5-6}$heterocycloalkyl, optionally substituted $CH_2C_{5-6}$heteroaryl, $CH_2OR^6$ and $CH_2NR^6R^7$.

In an embodiment, $R^1$ is selected from optionally substituted $C_{3-6}$cycloalkyl, optionally substituted $C_{5-6}$heterocycloalkyl, optionally substituted $C_{5-6}$heteroaryl, optionally substituted $C_{1-2}$alkylene$C_{5-6}$heterocycloalkyl and $C_{1-2}$alkyleneNR$^6R^7$.

In an embodiment $R^1$ is an optionally substituted monocyclic heterocycloalkyl comprising 5 or 6 ring atoms in which one or two atoms are selected from O, N, NH and NC$_{1-4}$alkyl.

In an embodiment $R^1$ is an optionally substituted monocyclic heteroaryl comprising 5 or 6 ring atoms in which one or two atoms are selected from O, N, NH and NC$_{1-4}$alkyl.

In an embodiment $R^1$ is an optionally substituted $CH_2$heterocycloalkyl wherein the heterocycloalkyl is a monocyclic heteroaryl comprising 5 or 6 ring atoms in which one or two atoms are selected from O, N, NH and NC$_{1-4}$alkyl.

In an embodiment $R^1$ is an optionally substituted $CH_2$heteroaryl, in which the heteroaryl is a monocyclic heteroaryl comprising 5 or 6 ring atoms in which one or two atoms are selected from O, N, NH and NC$_{1-4}$alkyl.

In an embodiment, $R^1$ is optionally substituted $C_{3-6}$cycloalkyl or optionally substituted $CH_2C_{3-6}$cycloalkyl.

In an embodiment, the heterocycloalkyl in $R^1$ is an optionally substituted monocyclic heterocycloalkyl such as, but not limited to, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In an embodiment, the heterocycloalkyl in $R^1$ is an optionally substituted polycyclic heterocycloalkyl, such as but not limited to, pyrolizidinyl and quinolizidinyl.

In an embodiment, the heterocycloalkyl in $R^1$ is an optionally substituted polycyclic heterocycloalkyl wherein the ring fusion between two or more rings includes more than one bond common to both rings and more than two atoms common to both rings. Examples of such bridged heterocycles include, but are not limited to, quinuclidinyl, diazabicyclo[2.2.1]heptyl and 7-oxabicyclo[2.2.1]heptyl.

In an embodiment, the heteroaryl in $R^1$ is an optionally substituted monocyclic heteroaryl, for example but not limited to, pyridinyl, pyrazinyl, pyrimidinyl, triazinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4 oxadiazolyl.

In an embodiment, the heteroaryl in $R^1$ is an optionally substituted polycyclic heteroaryl, such as but not limited to, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl and acridinyl.

In an embodiment, $R^1$ is unsubstituted.

In an embodiment, the $R^1$ is substituted with 1 to 5, 1 to 4, 1 to 3, 1 to 2 or 1, substituent group.

In an embodiment, the substituent groups for $R^1$ are selected from $C_{1-12}$alkyl and chemical groups that contains one or more heteroatoms selected from N, O, S, F, Cl, Br, I, and P. Exemplary chemical groups containing one or more heteroatoms include heterocycloalkyl, $NO_2$, OR, R'OR, Cl, Br, I, F, $CF_3$, C(=O)R, $NR_2$, SR, $SO_2R$, S(=O)R, CN, C(=O)OR, C(=O)$NR_2$, NRC(=O)R, NRC(=O)OR, R'$NR_2$, oxo (=O), imino (=NR), thio (=S), and oximino (=N—OR), wherein each "R" is hydrogen or a $C_{1-12}$alkyl and "R'" is a $C_{1-12}$alkylene.

In an embodiment, the substituent groups for $R^1$ are selected from $C_{1-6}$alkyl, F, Cl, $NO_2$, OR, R'OR, $CF_3$, C(=O)R, $NR_2$, SR, $SO_2R$, S(=O)R, CN, C(=O)OR, C(=O)NR2, NRC(=O)R, NRC(=O)OR, R'$NR_2$, oxo (=O), imino (=NR), thio (=S), and oximino (=N—OR), wherein each "R" is hydrogen or a $C_{1-6}$alkyl and "R'" is a $C_{1-6}$alkylene.

In an embodiment, the substituent groups for $R^1$ are selected from $C_{1-4}$alkyl, F, Cl, $NO_2$, OR, R'OR, $CF_3$, C(=O)R, NR2, SR, $SO_2R$, S(=O)R, CN, C(=O)OR, C(=O)NR2, NRC(=O)R, NRC(=O)OR, R'$NR_2$, oxo (=O), imino (=NR), thio (=S), and oximino (=N—OR), wherein each "R" is hydrogen or a $C_{1-4}$alkyl and "R'" is a $C_{1-4}$alkylene.

In an embodiment, the substituent groups for $R^1$ are selected from methyl, ethyl, F, Cl, $NO_2$, OH, $OCH_3$, $CH_2OCH_3$, $CH_2OH$, $CF_3$, C(=O)$CH_3$, N($CH_3$)$_2$, $NH_2$, $NHCH_3$, SH, $SCH_3$, $SO_2CH_3$, S(=O)$CH_3$, CN, C(=O)$OCH_3$, C(=O)OH, C(=O)N($CH_3$)$_2$, C(=O)$NH_2$, C(=O)$NHCH_3$, $NCH_3$C(=O)$CH_3$, NHC(=O)$CH_3$, $NCH_3$C(=O)$OCH_3$, NHC(=O)$OCH_3$, $NCH_3$C(=O)OH, NHC(=O)OH, $CH_2NH_2$, $CH_2N(CH_3)_2$, $CH_2NHCH_3$, oxo (=O), =NH, =$NCH_3$, thio (=S), and =N—OH and =$NOCH_3$.

In an embodiment, the substituent groups for $R^1$ are selected from methyl, ethyl and F.

In an embodiment $R^1$ is selected from:

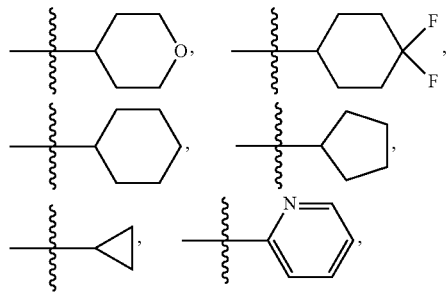

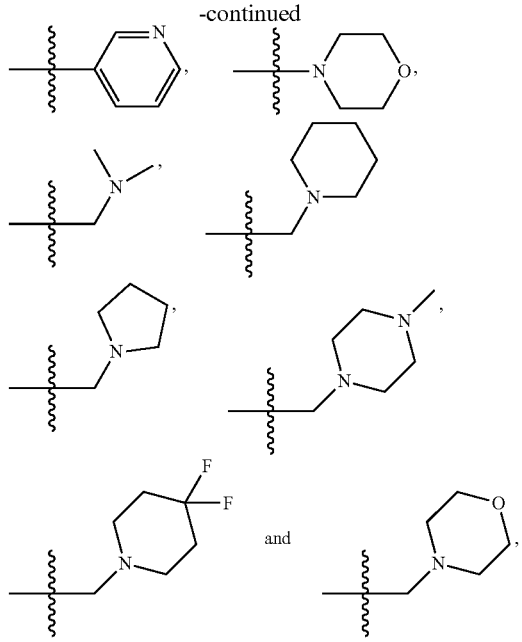

wherein ⁓ represents the point of attachment of the group to the remaining portion of the compounds of Formula I. In an embodiment, $R^1$ is

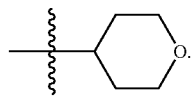

In an embodiment $R^2$ and $R^3$ are independently selected from H, fluoro, and $C_{1-4}$alkyl. In an embodiment, both of $R^2$ and $R^3$ are H. In an embodiment one of $R^2$ and $R^3$ is H and the other of $R^2$ and $R^3$ is methyl.

When at least one of $R^2$ and $R^3$ is other than H, the carbon to which $R^2$ and $R^3$ is attached is a chiral centre, therefore the compounds of Formula I include both R and S stereoisomers at this carbon atom, including all mixtures thereof. In an embodiment, the stereochemistry at the carbon to which $R^2$ and $R^3$ are attached, when at least one of $R^2$ and $R^3$ is other than H, is R. Therefore it is an embodiment that in the compounds of Formula I, greater than 50%, 65%, 70%, 75%, 80%, 85%, 90%, 95% or 99% of the molecules in a given sample of the compound, will have a stereochemistry at the carbon atom to which $R^2$ and $R^3$ is attached (where at least one of $R^2$ and $R^3$ is other than H) that is R. It is another embodiment that in the compounds of Formula I, greater than 50%, 65%, 70%, 75%, 80%, 85%, 90%, 95% or 99% of the molecules in a given sample of the compound, will have a stereochemistry at the carbon atom to which $R^2$ and $R^3$ is attached (where at least one of $R^2$ and $R^3$ is other than H) that is S.

In an embodiment, $R^2$ and $R^3$ together form an oxo (=O) group.

In an embodiment, $R^2$ and $R^3$, together with the carbon atom to which they are attached, form $C_{5-6}$cycloalkyl.

In an embodiment, $R^4$ is selected from OH, $OC_{1-6}$alkyl, $C_{1-6}$alkyleneOH, $C_{1-6}$alkyleneO$C_{1-6}$alkyl, $NH_2$, $NHC_{1-6}$alkyl, $N(C_{1-6}$alkyl)$_2$, $C_{1-6}$alkylene$NH_2$, $C_{1-6}$alkyleneNH$C_{1-6}$alkyl, $C_{1-6}$alkyleneN($C_{1-6}$alkyl)$_2$, F and Cl. In an embodiment, $R^4$ is selected from OH, $OC_{1-4}$alkyl, $C_{1-4}$alkyleneOH, $C_{1-4}$alkyleneO$C_{1-4}$alkyl, NH$_2$, NHC$_{1-4}$alkyl, N(C$_{1-4}$alkyl)$_2$, C$_{1-4}$alkyleneNH$_2$, C$_{1-4}$alkyleneNHC$_{1-4}$alkyl, C$_{1-4}$alkyleneN(C$_{1-6}$alkyl)$_2$, F and Cl. In an embodiment, R$^4$ is selected from OH, OCH$_3$, CH$_2$OH, CH$_2$OCH$_3$, NH$_2$, NHCH$_3$, N(CH$_3$)$_2$, CH$_2$NH$_2$, CH$_2$NHCH$_3$, CH$_2$N(CH$_3$)$_2$, F and Cl. In an embodiment, R$^4$ is OCH$_3$.

In an embodiment, R$^5$ is selected from optionally substituted monocyclic rings having 1-3 heteroatoms independently selected from N, O and S and the optional substituents are selected from 1 to 2 halo, C$_{1-4}$alkyl and C$_{1-4}$alkoxy. In an embodiment, R$^5$ is selected from optionally substituted monocyclic rings having 1-3 heteroatoms independently selected from N and O and the optional substituents are selected from 1 to 2 F, Cl, CH$_3$ and OCH$_3$. In an embodiment R$^5$ is an optionally substituted cyclic group having the following structure:

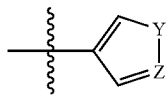

wherein Y and Z are selected from O, N, NH and NCH$_3$, and the optional substituents are selected from 1 to 2 F, Cl, CH$_3$ and OCH$_3$ and ⁓⁓⁓ represents the point of attachment of the group to the remaining portion of the compounds of Formula I. In an embodiment, R$^5$ is

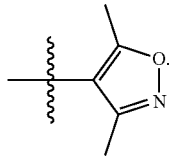 [SMILES: *c1c(C)noc1C]

In an embodiment, R$^6$ and R$^7$ are each independently selected from H, C$_{1-4}$alkyl, C$_{3-4}$cycloalkyl, C$_{5-6}$heterocycloalkyl and haloC$_{1-4}$alkyl. In an embodiment, R$^6$ and R$^7$ are each independently selected from H and C$_{1-4}$alkyl. In an embodiment, R$^6$ and R$^7$ are each independently selected from H and CH$_3$.

In an embodiment, A is selected from C$_{0-1}$alkylene, O, NH and NCH$_3$. In an embodiment, A is O or CH$_2$.

In an embodiment, X$^1$, X$^2$ and X$^3$ are the same or different and are selected from H, F, and C$_{1-4}$alkyl, provided that at least one of X$^1$, X$^2$ and X$^3$ is F. In an embodiment, X$^1$, X$^2$ and X$^3$ are the same or different and are selected from H, F, and CH$_3$, provided that at least one of X$^1$, X$^2$ and X$^3$ is F. In an embodiment one or two of X$^1$, X$^2$ and X$^3$ are F and the other of X$^1$, X$^2$ and X$^3$ is H. In an embodiment two of X$^1$, X$^2$ and X$^3$ are F and the other one of X$^1$, X$^2$ and X$^3$ is H.

In an embodiment one or more of the atoms in the compounds of Formula I are replaced with a radioactive isotope thereof. In an embodiment, the radioactive isotope is $^{18}$F. In an embodiment, at least one of X$^1$, X$^2$ and X$^3$ is $^{18}$F.

In an embodiment, R$^3$ in the compounds of Formula I is H, R$^2$ is C$_{1-6}$alkyl and the compounds have a stereochemistry that is predominately (i.e. greater than 50%, 65%, 70%, 75%, 80%, 85%, 90%, 95% or 99%) as follows:

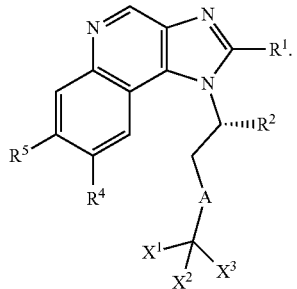

In an embodiment of the application there is included a compound of the Formula I, or a pharmaceutically acceptable salt, solvate or prodrug thereof:

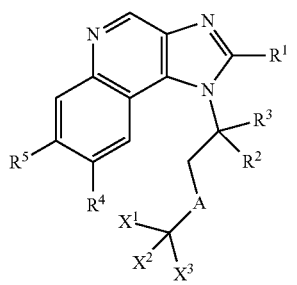

Formula I

R$^1$ is H, optionally substituted alkyl, optionally substituted alkenyl, optionally substituted cycloalkyl, optionally substituted aryl, optionally substituted heterocycloalkyl, optionally substituted heteroaryl, optionally substituted —CH$_2$-cycloalkyl, optionally substituted —CH$_2$-aryl, optionally substituted —CH$_2$-heterocycloalkyl, optionally substituted —CH$_2$-heteroaryl, optionally substituted —CH(C$_1$-C$_6$-alkyl)-alkyl, optionally substituted —CH(C$_1$-C$_6$-alkyl)cycloalkyl, optionally substituted —CH(C$_1$-C$_6$-alkyl)-aryl, optionally substituted —CH(C$_1$-C$_6$-alkyl)-heterocycloalkyl, or optionally substituted —CH(C$_1$-C$_6$-alkyl)-heteroaryl; OR$_6$, —CN, —CH$_2$OR$_6$, —NH-alkyl, —N(alkyl)$_2$', —CH$_2$N(alkyl)$_2$, —CH$_2$NH(alkyl);

R$^2$ and R$^3$ are independently H, fluoro, or alkyl; or R$^2$ and R$^3$ combined together to form an oxo group; alternatively, R$^2$ and R$^3$ can be taken together with the carbon atom to which they are attached to form a 3-6 membered cycloalkyl ring;

R$^4$ is OR$^6$, —CN, —CH$_2$OR$^6$, —NH-alkyl, —N(alkyl)$_2$', —CH$_2$N(alkyl)$_2$, —CH$_2$NH(alkyl), or halogen;

R$^5$ is an optionally substituted monocyclic ring having 1-3 heteroatoms independently selected from N and O; wherein the optional substituent is alkyl;

R$^6$ are each independently H, C$_1$-C$_6$ alkyl, cycloalkyl, or haloalkyl;

A is C, O, S, or NR$^6$; and

X$^1$, X$^2$, and X$^3$ are the same or different and is selected from H, halo, and lower alkyl.

In an embodiment, the compound of the present application is selected from the compounds of Examples 1 and 2 as illustrated below or a pharmaceutically acceptable salt, solvate and/or prodrug thereof:

4-[1-[(1  S)-2-(difluoromethoxy)-1-methyl-ethyl]-8-methoxy-2-tetrahydropyran-4-yl-imidazo[4,5-c]quinolin-7-yl]-3,5-dimethyl-isoxazole;

4-[2-(4,4-difluorocyclohexyl)-1-[(1  S)-2-(difluoromethoxy)-1-methyl-ethyl]-8-methoxy-imidazo[4,5-c]quinolin-7-yl]-3,5-dimethyl-isoxazole;

4-[2-cyclohexyl-1-[(1 S)-2-(difluoromethoxy)-1-methyl-ethyl]-8-methoxy-imidazo[4,5-c]quinolin-7-yl]-3,5-dimethyl-isoxazole;
4-[2-cyclopentyl-1-[(1 S)-2-(difluoromethoxy)-1-methyl-ethyl]-8-methoxy-imidazo[4,5-c]quinolin-7-yl]-3,5-dimethyl-isoxazole;
4-[2-cyclopropyl-1-[(1 S)-2-(difluoromethoxy)-1-methyl-ethyl]-8-methoxy-imidazo[4,5-c]quinolin-7-yl]-3,5-dimethyl-isoxazole hydrochloride;
4-[1-[(1 S)-2-(difluoromethoxy)-1-methyl-ethyl]-8-methoxy-2-(2-pyridyl)imidazo[4,5-c]quinolin-7-yl]-3,5-dimethyl-isoxazole;
4-[1-[(1R)-2-(difluoromethoxy)-1-methyl-ethyl]-8-methoxy-2-tetrahydropyran-4-yl-imidazo[4,5-c]quinolin-7-yl]-3,5-dimethyl-isoxazole;
4-[2-(4,4-difluorocyclohexyl)-1-[(1R)-2-(difluoromethoxy)-1-methyl-ethyl]-8-methoxy-imidazo[4,5-c]quinolin-7-yl]-3,5-dimethyl-isoxazole;
4-[1-[(1R)-2-(difluoromethoxy)-1-methyl-ethyl]-8-methoxy-2-(3-pyridyl)imidazo[4,5-c]quinolin-7-yl]-3,5-dimethyl-isoxazole;
4-[2-cyclohexyl-1-[(1R)-2-(difluoromethoxy)-1-methyl-ethyl]-8-methoxy-imidazo[4,5-c]quinolin-7-yl]-3,5-dimethyl-isoxazole;
4-[2-cyclopentyl-1-[(1R)-2-(difluoromethoxy)-1-methyl-ethyl]-8-methoxy-imidazo[4,5-c]quinolin-7-yl]-3,5-dimethyl-isoxazole;
4-[2-cyclopropyl-1-[(1R)-2-(difluoromethoxy)-1-methyl-ethyl]-8-methoxy-imidazo[4,5-c]quinolin-7-yl]-3,5-dimethyl-isoxazole hydrochloride;
4-[1-[(1R)-2-(difluoromethoxy)-1-methyl-ethyl]-8-methoxy-2-(2-pyridyl)imidazo[4,5-c]quinolin-7-yl]-3,5-dimethyl-isoxazole;
4-[8-methoxy-2-tetrahydropyran-4-yl-1-(3,3,3-trifluoropropyl)imidazo[4,5-c]quinolin-7-yl]-3,5-dimethyl-isoxazole;
4-[2-(4,4-difluorocyclohexyl)-8-methoxy-1-(3,3,3-trifluoropropyl)imidazo[4,5-c]quinolin-7-yl]-3,5-dimethyl-isoxazole;
4-[[1-[(1R)-2-(difluoromethoxy)-1-methyl-ethyl]-7-(3,5-dimethylisoxazol-4-yl)-8-methoxy-imidazo[4,5-c]quinolin-2-yl]methyl]morpholine trihydrochloride;
1-[1-[(1R)-2-(difluoromethoxy)-1-methyl-ethyl]-7-(3,5-dimethylisoxazol-4-yl)-8-methoxy-imidazo[4,5-c]quinolin-2-yl]-N, N-dimethyl-methanamine;
4-[1-[(1R)-2-(difluoromethoxy)-1-methyl-ethyl]-8-methoxy-2-(1-piperidylmethyl)imidazo[4,5-c]quinolin-7-yl]-3,5-dimethyl-isoxazole dihydrochloride;
4-[1-[(1R)-2-(difluoromethoxy)-1-methyl-ethyl]-8-methoxy-2-(pyrrolidin-1-ylmethyl)imidazo[4,5-c]quinolin-7-yl]-3,5-dimethyl-isoxazole dihydrochloride;
4-[1-[(1R)-2-(difluoromethoxy)-1-methyl-ethyl]-8-methoxy-2-[(4-methylpiperazin-1-yl)methyl]imidazo[4,5-c]quinolin-7-yl]-3,5-dimethyl-isoxazole;
4-[1-[(1R)-2-(difluoromethoxy)-1-methyl-ethyl]-2-[(4,4-difluoro-1-piperidyl)methyl]-8-methoxy-imidazo[4,5-c]quinolin-7-yl]-3,5-dimethyl-isoxazole;
and
4-[1-[2-(difluoromethoxy)ethyl]-8-methoxy-2-tetrahydropyran-4-yl-imidazo[4,5-c]quinolin-7-yl]-3,5-dimethyl-isoxazole.

In an embodiment, the compound of the present application is selected from:

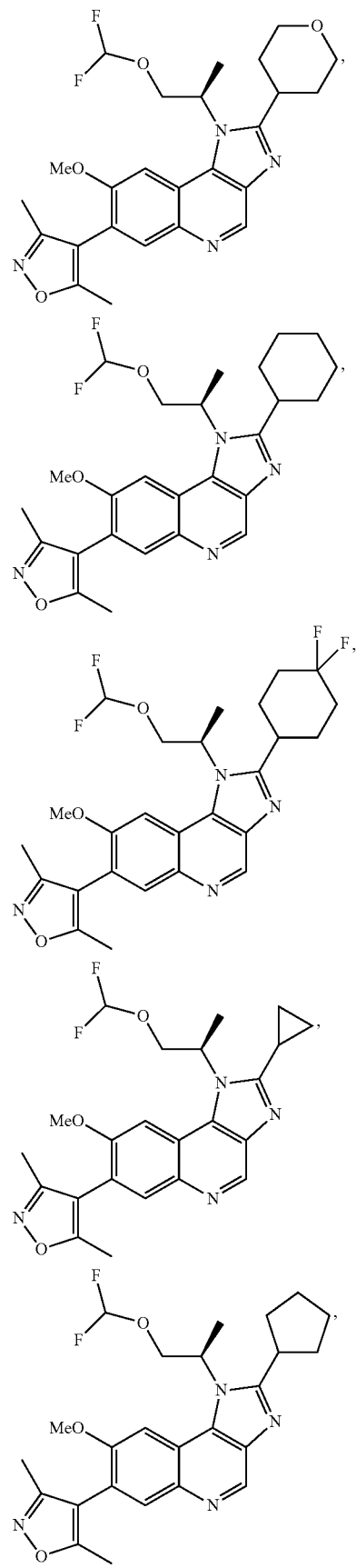

27
-continued
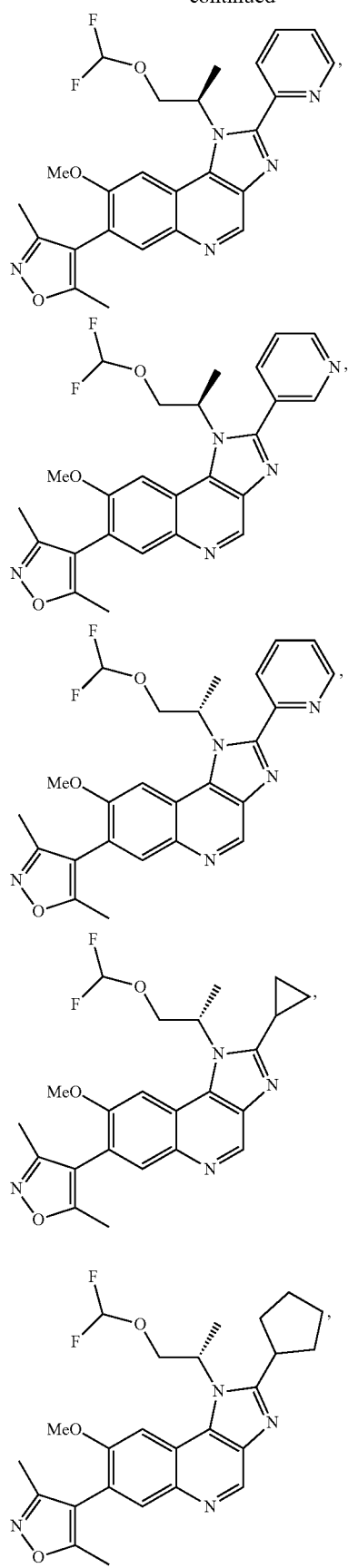
28
-continued
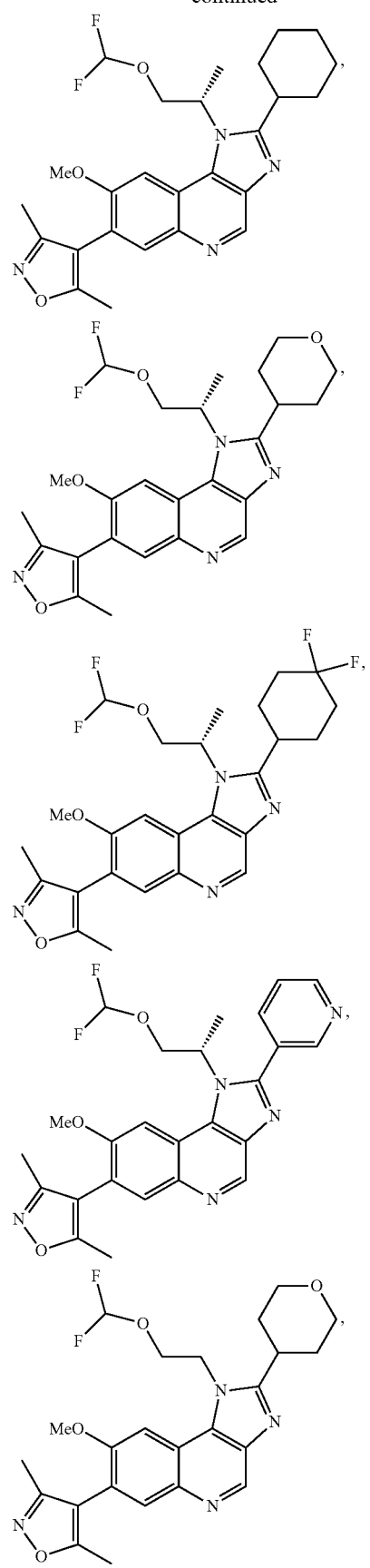

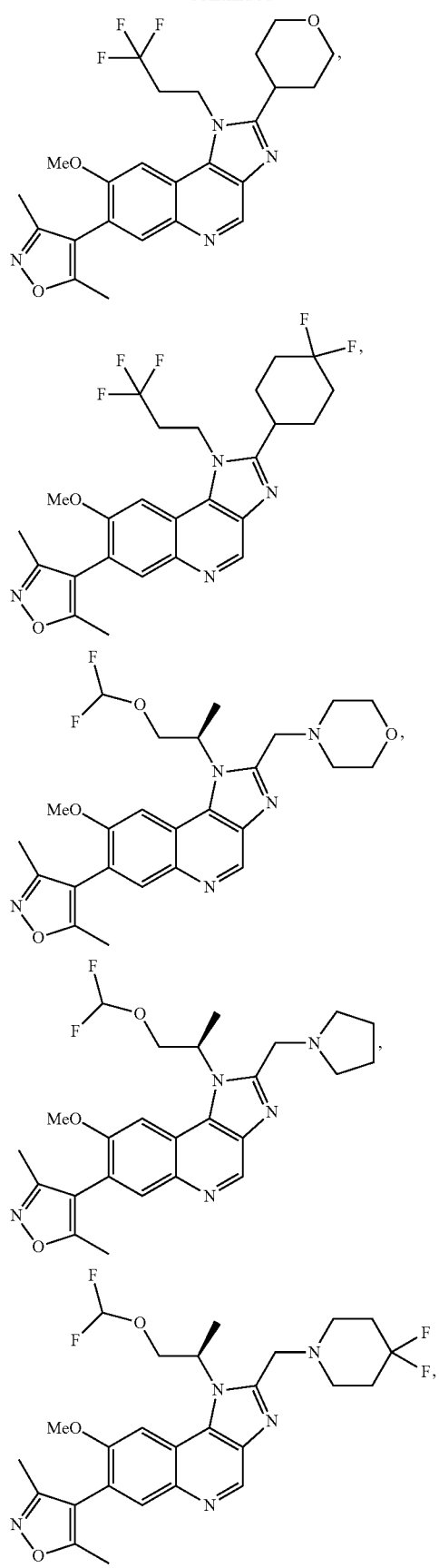
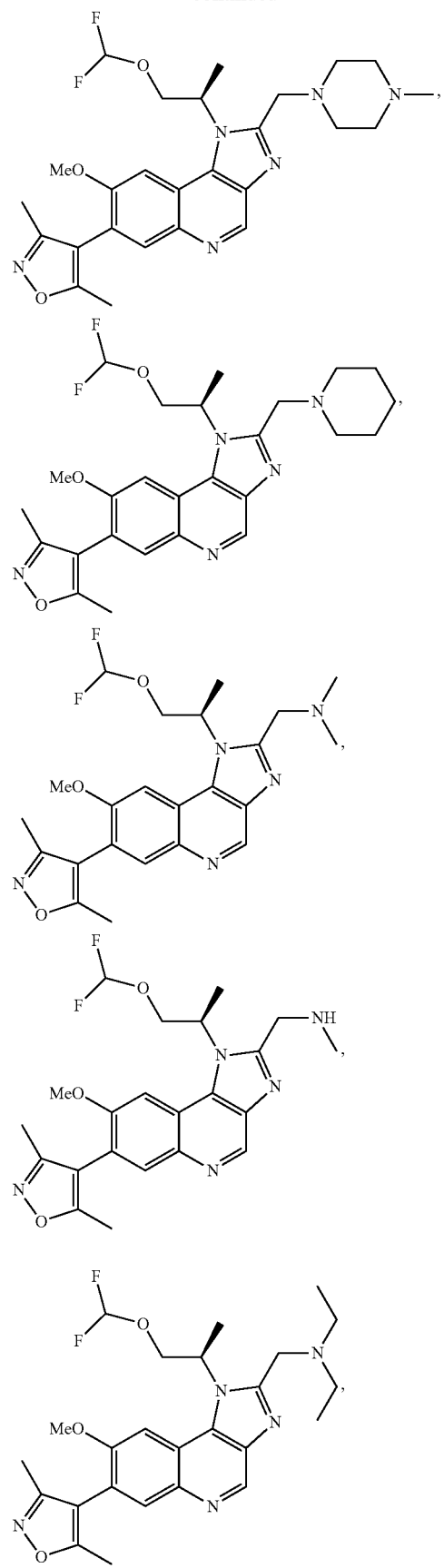

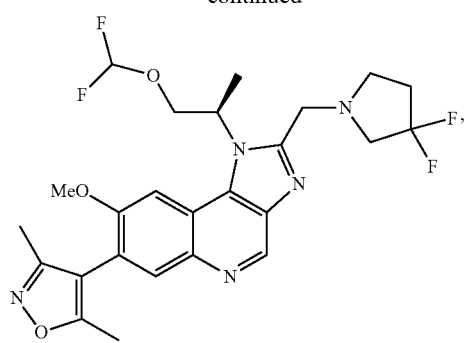
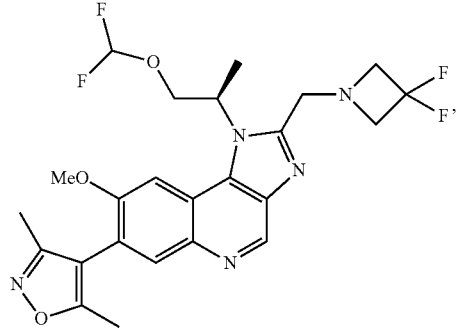
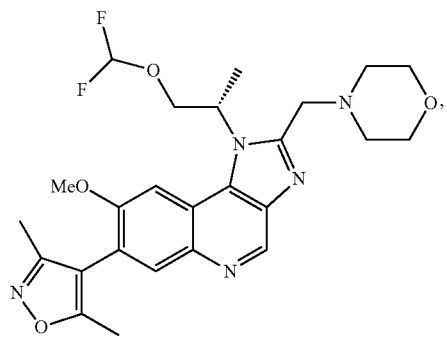
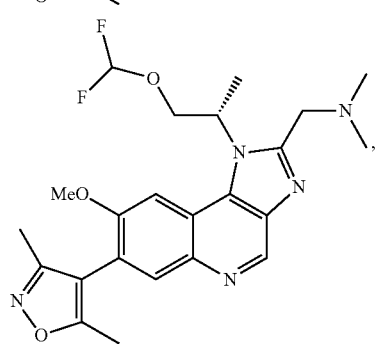
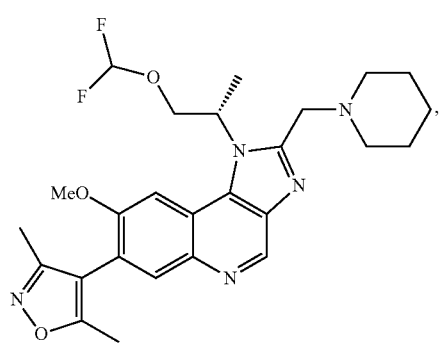
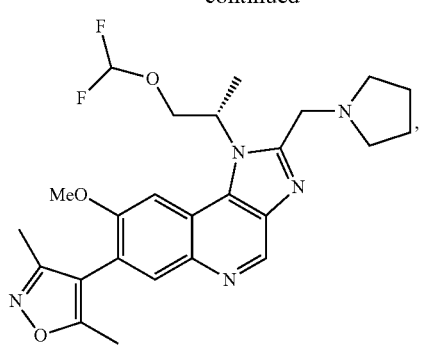
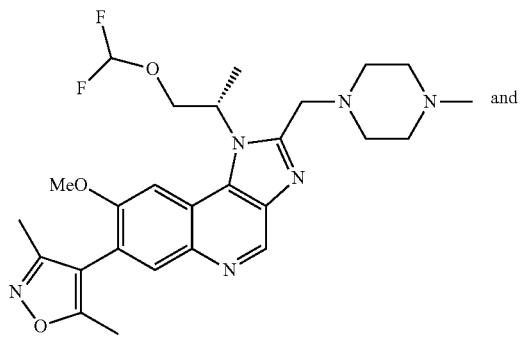
or a pharmaceutically acceptable salt, solvate and/or prodrug thereof.
In an embodiment, the compound of Formula I is selected from:

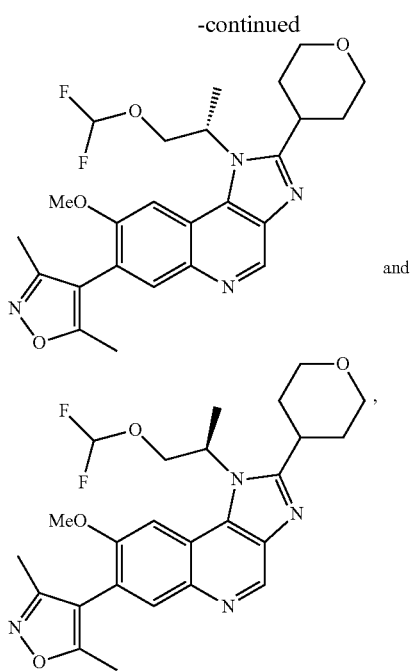

or a pharmaceutically acceptable salt, solvate and/or prodrug thereof.

In an embodiment, the compound of Formula I is:

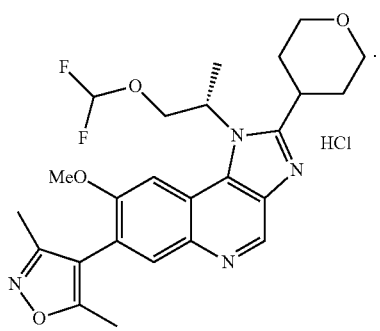 [SMILES: COc1cc2c(cc1-c1c(C)noc1C)ncc1nc(C3CCOCC3)n([C@@H](C)COC(F)F)c12 ; Cl]

In an embodiment, the application includes a compound of Formula Ia or a pharmaceutically acceptable salt, solvate or prodrug thereof:

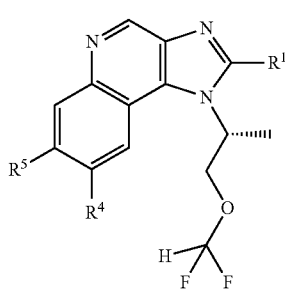

Formula Ia wherein $R^1$ is H, optionally substituted alkyl, optionally substituted alkenyl, optionally substituted cycloalkyl, optionally substituted aryl, optionally substituted heterocycloalkyl, optionally substituted heteroaryl, optionally substituted —CH$_2$-cycloalkyl, optionally substituted —CH$_2$-aryl, optionally substituted —CH$_2$-heterocycloalkyl, optionally substituted —CH$_2$-heteroaryl, optionally substituted —CH(C$_1$-C$_6$-alkyl)-alkyl, optionally substituted —CH(C$_1$-C$_6$-alkyl)cycloalkyl, optionally substituted —CH(C$_1$-C$_6$-alkyl)-aryl, optionally substituted —CH(C$_1$-C$_6$-alkyl)-heterocycloalkyl, or optionally substituted —CH(C$_1$-C$_6$-alkyl)-heteroaryl; OR$_6$, —CN, —CH$_2$OR$_6$, —NH-alkyl, —N(alkyl)$_2$', —CH$_2$N(alkyl)$_2$, —CH$_2$NH(alkyl);

$R^4$ is OR$^6$, —CN, —CH$_2$OR$^6$, —NH-alkyl, —N(alkyl)$_2$', —CH$_2$N(alkyl)$_2$, —CH$_2$NH(alkyl), or halogen;

$R^5$ is an optionally substituted monocyclic ring having 1-3 heteroatoms independently selected from N and O; wherein the optional substituent is alkyl; and $R^6$ are each independently H, C$_1$-C$_6$ alkyl, cycloalkyl, or haloalkyl.

In an embodiment, the application includes a compound of Formula Ib or a pharmaceutically acceptable salt, solvate or prodrug thereof:

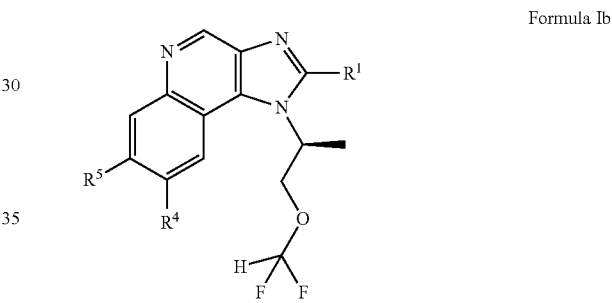

Formula Ib wherein $R^1$ is H, optionally substituted alkyl, optionally substituted alkenyl, optionally substituted cycloalkyl, optionally substituted aryl, optionally substituted heterocycloalkyl, optionally substituted heteroaryl, optionally substituted —CH$_2$-cycloalkyl, optionally substituted —CH$_2$-aryl, optionally substituted —CH$_2$-heterocycloalkyl, optionally substituted —CH$_2$-heteroaryl, optionally substituted —CH(C$_1$-C$_6$-alkyl)-alkyl, optionally substituted —CH(C$_1$-C$_6$-alkyl)cycloalkyl, optionally substituted —CH(C$_1$-C$_6$-alkyl)-aryl, optionally substituted —CH(C$_1$-C$_6$-alkyl)-heterocycloalkyl, or optionally substituted —CH(C$_1$-C$_6$-alkyl)-heteroaryl; OR$_6$, —CN, —CH$_2$OR$_6$, —NH-alkyl, —N(alkyl)$_2$', —CH$_2$N(alkyl)$_2$, —CH$_2$NH(alkyl);

$R^4$ is OR$^6$, —CN, —CH$_2$OR$^6$, —NH-alkyl, —N(alkyl)$_2$', —CH$_2$N(alkyl)$_2$, —CH$_2$NH(alkyl), or halogen;

$R^5$ is an optionally substituted monocyclic ring having 1-3 heteroatoms independently selected from N and O; wherein the optional substituent is alkyl; and $R^6$ are each independently H, C$_1$-C$_6$ alkyl, cycloalkyl, or haloalkyl.

In an embodiment, the present application also includes a compound of Formula Ic:

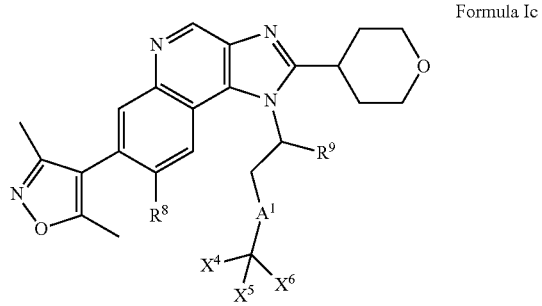

Formula Ic or a pharmaceutically acceptable salt, solvate and/or prodrug thereof,
wherein:
$R^8$ is selected from $OC_{1-6}$alkyl and halogen;
$R^9$ is selected from H, fluoro, and $C_{1-6}$alkyl;
A is selected from $C_{0-6}$alkylene, O, S, NH and $NC_{1-6}$alkyl;
$X^4$, $X^5$ and $X^6$ are the same or different and are selected from H, halogen, and $C_{1-6}$alkyl, provided that at least one of $X^4$, $X^5$ and $X^6$ is F; and
one or more of the atoms in the compounds of Formula Ic are optionally replaced with a radioactive isotope thereof.

In an embodiment, $R^8$ is selected from $OCH_3$, F and Cl. In an embodiment, $R^8$ is $OCH_3$.

In an embodiment, $R^9$ is selected from H, fluoro, and methyl. In an embodiment $R^9$ is methyl.

In an embodiment, A is selected from $C_{0-4}$alkylene, O, NH and $NC_{1-4}$alkyl. In an embodiment, A is $CH_2$ or O.

In an embodiment, $X^4$, $X^5$ and $X^6$ are the same or different and are selected from H, F, and $C_{1-4}$alkyl, provided that at least one of $X^4$, $X^5$ and $X^6$ is F. In an embodiment, $X^4$, $X^5$ and $X^6$ are the same or different and are selected from H, F, and $CH_3$, provided that at least one of $X^4$, $X^5$ and $X^6$ is F. In an embodiment one or two of $X^4$, $X^5$ and $X^6$ are F and the other of $X^4$, $X^5$ and $X^6$ is H. In an embodiment two of $X^4$, $X^5$ and $X^6$ are F and the other one of $X^4$, $X^5$ and $X^6$ is H.

In an embodiment, the compound of Formula Ic has a stereochemistry that is predominately greater than 50%, 65%, 70%, 75%, 80%, 85%, 90%, 95% or 99% as follows:

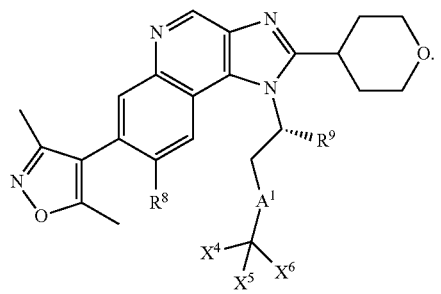

In an embodiment, the compounds of the application are in the form of a pharmaceutically acceptable salt.

Preparation of Compounds

Compounds of the present application can be prepared by various synthetic processes. The choice of particular structural features and/or substituents may influence the selection of one process over another. The selection of a particular process to prepare a given compound of The application is within the purview of the person of skill in the art. Some starting materials for preparing compounds of the present application are available from commercial chemical sources. Other starting materials, for example as described below, are readily prepared from available precursors using straightforward transformations that are well known in the art.

In some embodiments of the application, the compounds of the application are generally prepared according to the process illustrated in Scheme I. Variables in the following schemes are as defined above for Formula I unless otherwise specified.

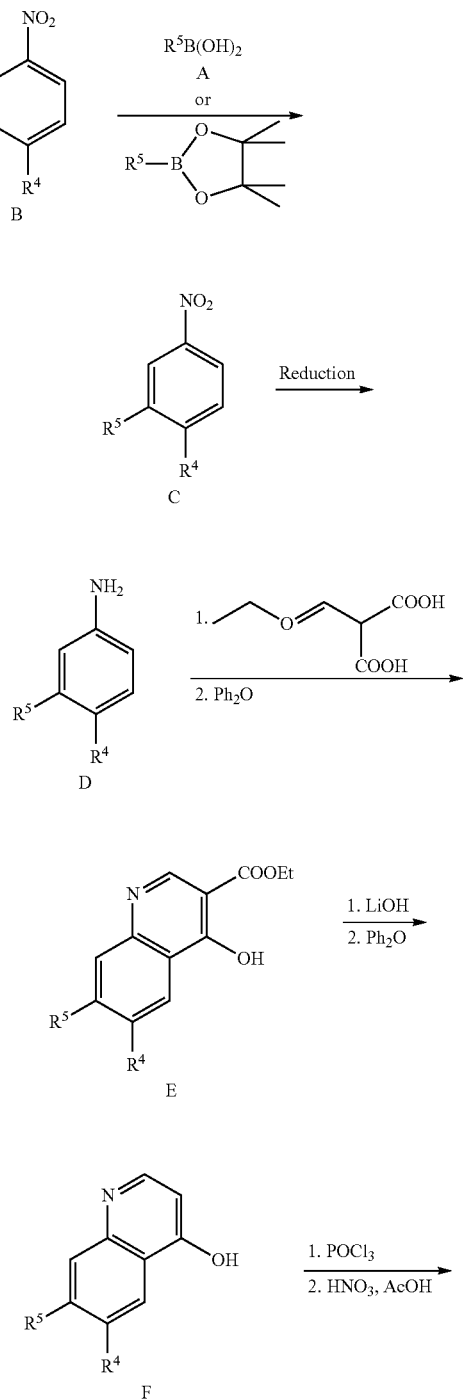

Scheme I

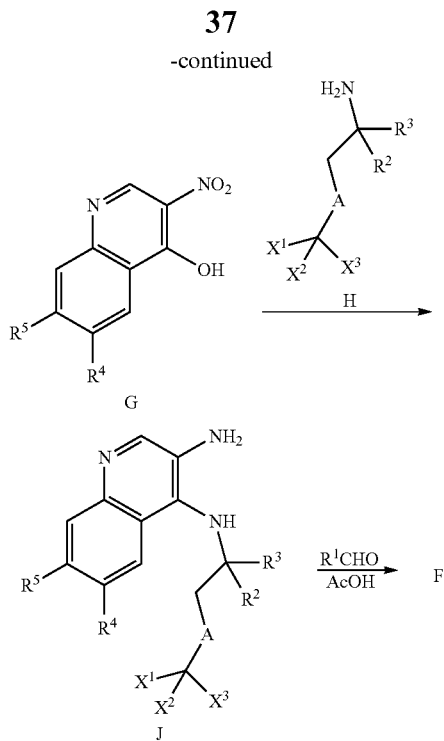

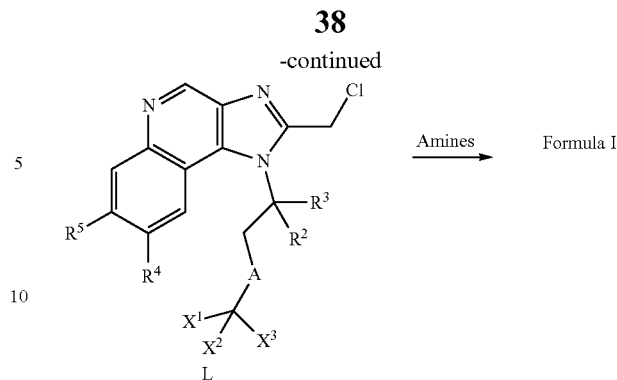

In accordance with the embodiment as shown in Scheme I, the compounds of the present application are prepared by coupling a boronic acid or boronated derivative A with iodonitrobenzene B to give intermediate C. Subsequent reduction of intermediate C with reducing agents provide the aniline intermediate D. Coupling of D with the malonic acid derivative followed by cyclization affords quinoline E. Hydrolysis of E followed by decarcarboxylation affords F which is then chlorinated with POCl₃ followed by selective nitration with concentrated nitric acid to give G. Nucleophilic displacement of chloro-quinoline G with primary amine H (prepared, for example, as shown in Scheme IV) followed by reduction under palladium catalysed hydrogenation gives the diamino derivative J which is then cyclized with various aldehydes K, or alternatively acetals or orthoformates, to afford compounds of Formula I.

In other embodiments, compounds of the application are prepared by acid-catalyzed cyclization of compounds J with halomethylorthoformates K to provide compounds L, followed by nucleophilic displacement of nucleophiles to provide compounds of the application as shown in Scheme II.

Scheme II

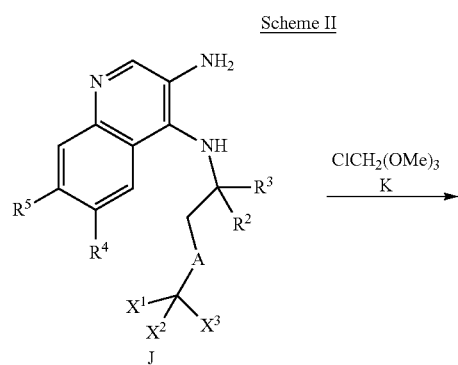

In other embodiments, compounds of the application are prepared by coupling of intermediate J to acids under activating conditions (e.g. EDCl, HATU, HBTU etc.) or acyl halides to give intermediate M which on cyclization affords the desired products as shown in Scheme III.

Scheme III

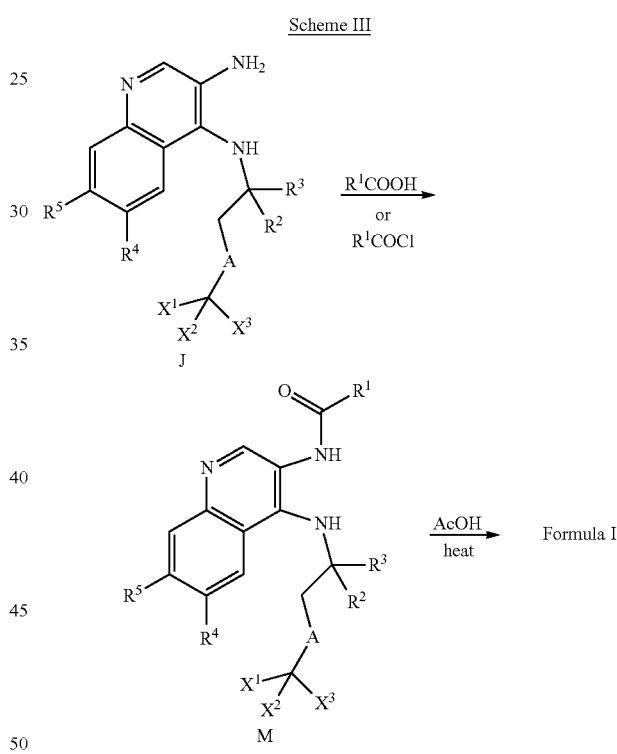

In some embodiments, amines H are obtained from commercial sources or prepared by methods known in the art, for example as shown in Scheme IV, for compounds of Formula H wherein $X^1$ and $X^2$ are F and $X^3$ is H.

Scheme IV

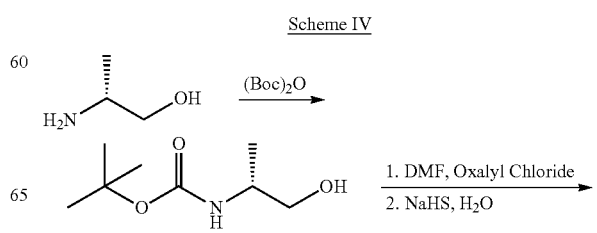

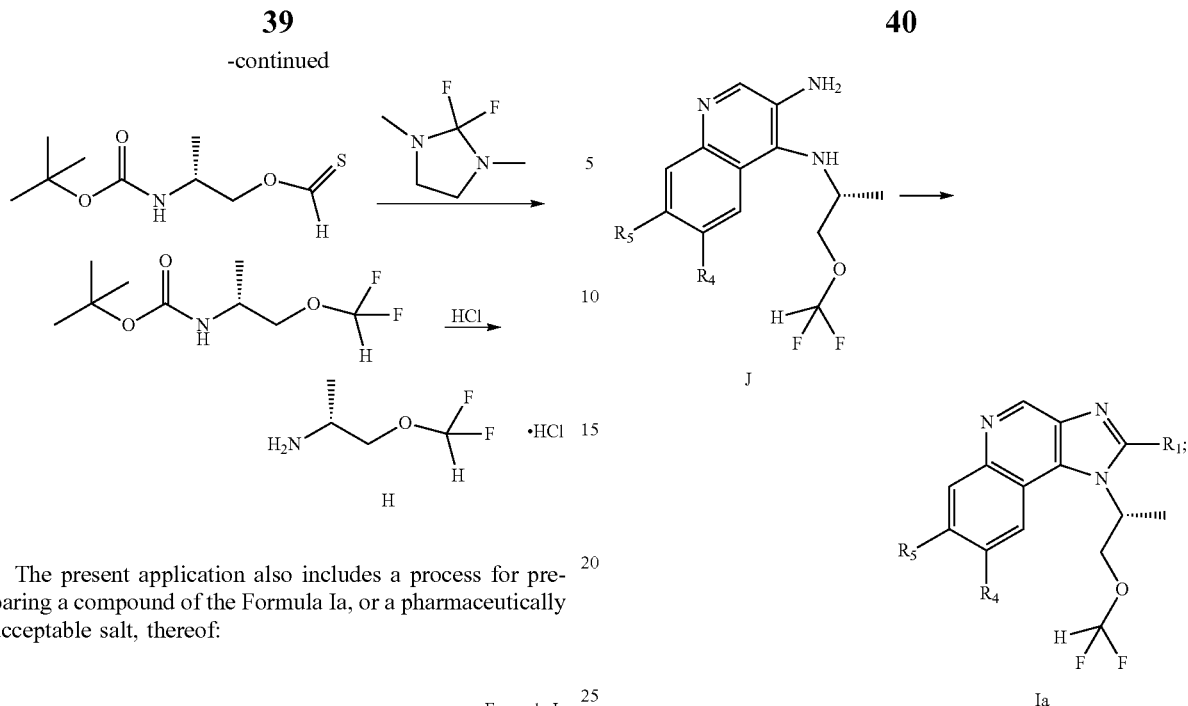

The present application also includes a process for preparing a compound of the Formula Ia, or a pharmaceutically acceptable salt, thereof:

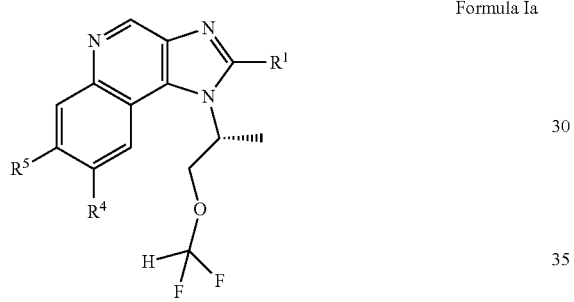

Formula Ia wherein

R¹ is H, optionally substituted alkyl, optionally substituted alkenyl, optionally substituted cycloalkyl, optionally substituted aryl, optionally substituted heterocycloalkyl, optionally substituted heteroaryl, optionally substituted —CH$_2$-cycloalkyl, optionally substituted —CH$_2$-aryl, optionally substituted —CH$_2$-heterocycloalkyl, optionally substituted —CH$_2$-heteroaryl, optionally substituted —CH(C$_1$-C$_6$-alkyl)-alkyl, optionally substituted —CH(C$_1$-C$_6$-alkyl)cycloalkyl, optionally substituted —CH(C$_1$-C$_6$-alkyl)-aryl, optionally substituted —CH(C$_1$-C$_6$-alkyl)-heterocycloalkyl, or optionally substituted —CH(C$_1$-C$_6$-alkyl)-heteroaryl; OR$_6$, —CN, —CH$_2$OR$_6$, —NH-alkyl, —N(alkyl)$_2$', —CH$_2$N(alkyl)$_2$, —CH$_2$NH(alkyl);

R⁴ is OR⁶, —CN, —CH$_2$OR⁶, —NH-alkyl, —N(alkyl)$_2$', —CH$_2$N(alkyl)$_2$, —CH$_2$NH(alkyl), or halogen;

R⁵ is an optionally substituted monocyclic ring having 1-3 heteroatoms independently selected from N and O; wherein the optional substituent is alkyl; and R⁶ are each independently H, C$_1$-C$_6$ alkyl, cycloalkyl, or haloalkyl.

said process comprising the steps of:

(a) reacting a compound of the formula J with an aldehydes of the formula R¹CHO, or alternatively acetals or orthoformates, under conditions to provide the compound of Formula Ia:

(b) acid-catalyzed cyclization of compounds J with halomethylorthoformates of the formula ClCH$_2$(OMe)$_3$ under conditions to provide compounds of formula L, followed by nucleophilic displacement of nucleophiles with amines under conditions to provide compounds of Formula Ia:

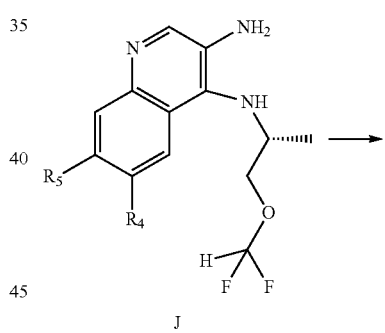

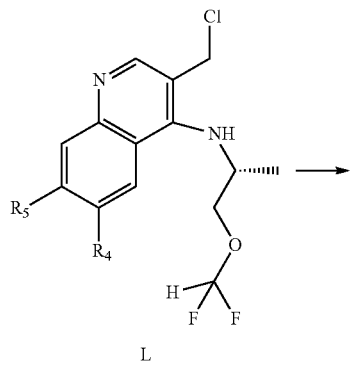

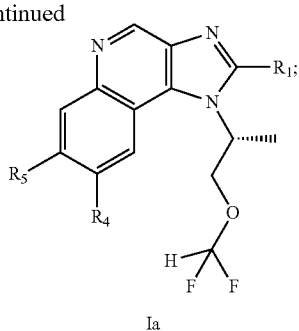

(c) coupling of intermediate J to acids of Formula $R^1CO_2H$ or acid halides of Formula $R^1C(O)Cl$ under activating conditions (e.g. EDCl, HATU, HBTU etc.) under conditions to give intermediate M which on cyclization provides compounds of Formula Ia:

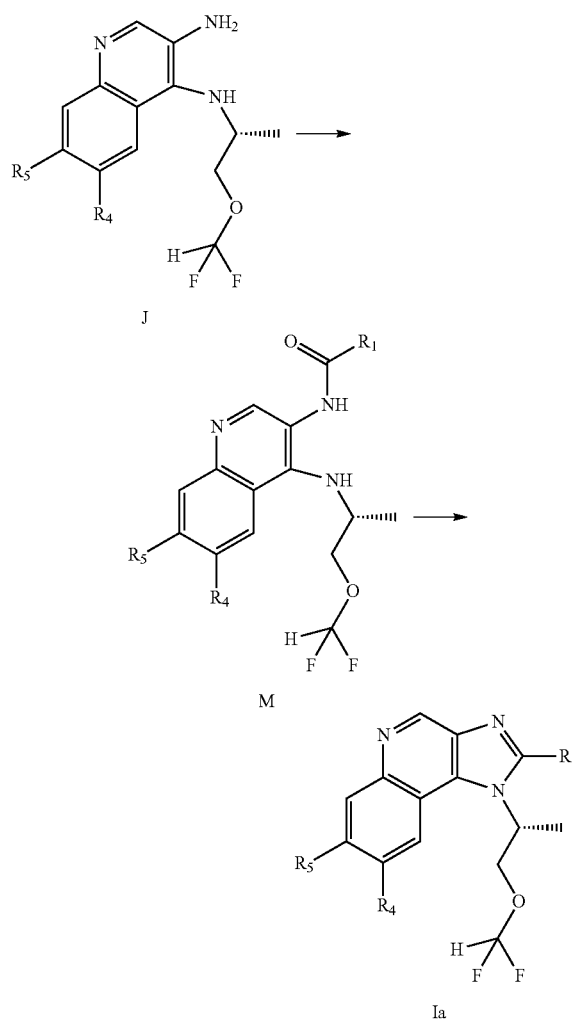

wherein $R^1$, $R^4$ and $R^5$ are as defined for Formula Ia.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

All process/method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

Compositions

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier. In embodiments of the application the pharmaceutical compositions are used in the treatment of nay of the diseases, disorders or conditions described herein.

The compounds of the application are administered to a subject in a variety of forms depending on the selected route of administration, as will be understood by those skilled in the art. For example, a compound of the application is administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, a compound of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluorom ethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein a compound of the application is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

In some embodiments a compound of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound of the application including pharmaceutically acceptable salts, solvates and/or prodrugs thereof is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

A compound of the application is either used alone or in combination with other known agents useful for treating diseases, disorders or conditions that are mediated by BET protein, and those that are treatable with a BET protein inhibitor. When used in combination with other agents useful in treating diseases, disorders or conditions mediated by BET protein inhibition, it is an embodiment that a compound of the application is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application, an additional therapeutic agent, and a pharmaceutically acceptable carrier.

The dosage of a compound of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a compound of the application is administered initially in a suitable dosage that is adjusted as required, depending on the clinical response. Dosages will generally be selected to maintain a serum level of the compound of the application from about 0.01 µg/cc to about 1000 µg/cc, or about 0.1 µg/cc to about 100 µg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. In an embodiment of the application, compositions are formulated for oral administration and the one or more compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. In embodiments of the application the one or more compounds of the application are administered in a single daily, weekly or monthly dose or the total daily dose is divided into two, three or four daily doses.

In the above, the term "a compound" also includes embodiments wherein one or more compounds are referenced.

III. Methods and Uses of the Application

The compounds of the application have been shown to be inhibitors of BET protein activity.

Accordingly, the present application includes a method for inhibiting BET protein in a cell, either in a biological sample or in a patient, comprising administering an effective amount of one or more compounds of the application to the cell. The application also includes a use of one or more compounds of the application for inhibition of BET protein activity in a cell as well as a use of one or more compounds of the application for the preparation of a medicament for inhibition of BET protein in a cell. The application further includes one or more compounds of the application for use in inhibiting BET protein in a cell.

As the compounds of the application have been shown to be capable of inhibiting BET protein activity, the compounds of the application are useful for treating diseases, disorders or conditions mediated by a BET protein. Therefore the compounds of the present application are useful as medicaments. Accordingly, the present application includes a compound of the application for use as a medicament.

The present application also includes a method of treating a disease, disorder or condition that is treatable with a BET protein inhibitor comprising administering a therapeutically effective amount of one or more compounds of the application to a subject in need thereof.

The present application also includes a use of one or more compounds of the application for treatment of a disease, disorder or condition mediated by a BET protein as well as a use of one or more compounds of the application for the preparation of a medicament for treatment of a disease, disorder or condition mediated by a BET protein. The application further includes one or more compounds of the application for use in treating a disease, disorder or condition mediated by a BET protein.

In an embodiment, the disease, disorder or condition mediated by a BET protein is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

Compounds of the application have been demonstrated to be effective against the cell lines of a 60 human tumor cell line panel. Therefore in another embodiment of the present application, the disease, disorder or condition treatable by BET protein inhibition is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

In an embodiment, the cancer is selected from a cancer of the skin, blood, prostate, colorectum, pancreas, kidney, ovary, breast, for example mammary, liver, tongue and lung. In another embodiment, the cancer is selected from leukaemia, lymphoma, non-Hodgkin's lymphoma, Burkitt lymphoma, MLL-fusion lymphoma, primary effusion leukemia and multiple myeloma. In a further embodiment of the present application, the cancer is selected from leukemia, melanoma, lung cancer, colon cancer, brain cancer, ovarian cancer, breast cancer, prostate cancer and kidney cancer.

In an embodiment, the BET-mediated disease, disorder or condition is a disease, disorder or condition associated with an uncontrolled and/or abnormal cellular activity affected directly or indirectly by a BET protein or by a variant and undesired form of a BET protein. In another embodiment, the uncontrolled and/or abnormal cellular activity that is affected directly or indirectly by a BET protein is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities mediated directly or indirectly by BET protein in a cell, either in a biological sample or in a subject, comprising administering an effective amount of one or more compounds of the application to the cell. The application also includes a use of one or more compounds of the application for inhibition of uncontrolled and/or abnormal cellular activities mediated directly or indirectly by BET protein in a cell as well as a use of one or more compounds of the application for the preparation of a medicament for inhibition of uncontrolled and/or abnormal cellular activities mediated directly or indirectly by BET protein in a cell. The application further includes one or more compounds of the application for use in inhibiting uncontrolled and/or abnormal cellular activities mediated directly or indirectly by BET protein in a cell.

Accordingly, the present application also includes a method of treating a disease, disorder or condition that is mediated by BET protein comprising administering a therapeutically effective amount of one or more compounds of the application in combination with another known agent useful for treatment of a disease, disorder or condition mediated by BET protein to a subject in need thereof. The present application also includes a use of one or more compounds of the application in combination with a known agent useful for treatment of a disease, disorder or condition mediated by a BET protein, for treatment of a disease, disorder or condition mediated by BET protein.

In an embodiment, the disease, disorder or condition treatable with a BET protein inhibitor is cancer such as multiple myeloma, lymphoma, leukemia, ovarian cancer, brain cancer, lung cancer, pancreatic cancer and brain cancers.

In a further embodiment, the disease, disorder or condition mediated BET is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

The following non-limiting examples are illustrative of the present application:

EXAMPLES

The following non-limiting examples are illustrative of the present application:

Example 1

A. General Methods

All starting materials used herein were commercially available or earlier described in the literature. The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as an internal reference, in deuterated chloroform as solvent unless otherwise indicated. All reported chemical shifts are in ppm on the delta-scale, and the fine splitting of the signals as appearing in the recordings is generally indicated, for example as s: singlet, br s: broad singlet, d: doublet, t: triplet, q: quartet, m: multiplet. Unless otherwise indicated, in the tables below, $^1$H NMR data was obtained at 400 MHz, using CDCl$_3$ as the solvent. A summary the $^1$H NMR and liquid chromatograph mass spectral (LCMS) characteristics of representative compounds is provided in Tables 1 and 2.

Purification of products was carried out using Chem Elut Extraction Columns (Varian, cat #1219-8002), Mega BE-SI (Bond Elut Silica) SPE Columns (Varian, cat #12256018; 12256026; 12256034) or by flash chromatography in silica-filled glass columns.

Example 2: Representative Synthesis of Compounds Using Aldehydes and AcOH (Method A)

Scheme V: General Scheme for making claimed compounds using Method A:

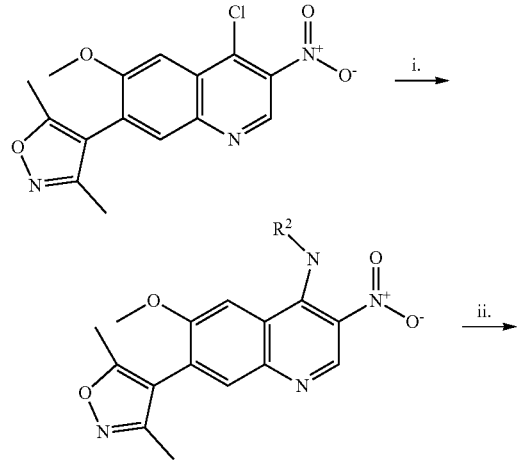

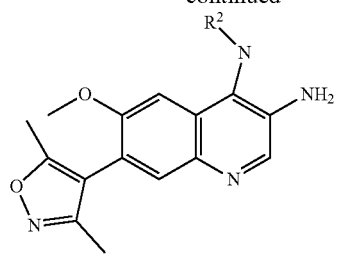

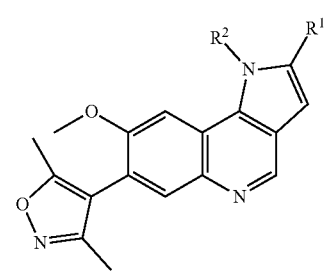

i. R$^2$NH$_2$, DCM, Et$_3$N. ii. 10% Pd/C, THF, 1 atm H$_2$. iii. R$^1$CHO, HOAc, DMF.

(a) 4-[1-[(1 S)-2-(difluoromethoxy)-1-methyl-ethyl]-8-methoxy-2-tetrahydropyran-4-yl-imidazo[4,5-c]quinolin-7-yl]-3,5-dimethyl-isoxazole

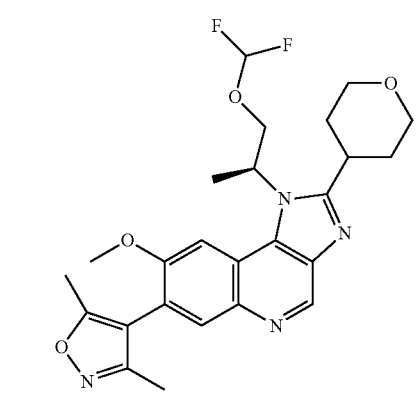 [SMILES: COc1cc2c(cc1-c1c(C)noc1C)ncc1nc(C3CCOCC3)n([C@@H](C)COC(F)F)c12]

Step 1:

To a stirred solution of N4-[(1 S)-2-(difluoromethoxy)-1-methyl-ethyl]-7-(3,5-dimethylisoxazol-4-yl)-6-methoxy-quinoline-3,4-diamine (100 mg, 0.255 mmol) in DMF (5 mL) and AcOH (0.62 mL) was added tetrahydropyran-4-carbaldehyde (91.1 mg, 0.765 mmol) and the resulting mixture was stirred overnight at room temperature. The mixture was diluted with ethyl acetate and washed with saturated NaHCO$_3$(3×) and brine (1×). The organic phase was dried, filtered and concentrated in vacuo then chromatographed on silica gel eluting with EtOAc. The product containing fractions were concentrated in vacuo and stirred in diethyl ether/hexanes and the resulting suspension was filtered to collect the desired product as an off-white solid (45 mg, 36%).

(b) 4-[2-(4,4-difluorocyclohexyl)-1-[(1 S)-2-(difluoromethoxy)-1-methyl-ethyl]-8-methoxy-imidazo[4,5-c]quinolin-7-yl]-3,5-dimethyl-isoxazole

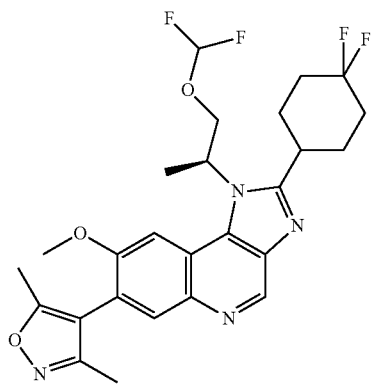 [SMILES: COc1cc2c(cc1-c1c(C)noc1C)ncc1nc(C3CCC(F)(F)CC3)n([C@@H](C)COC(F)F)c12]

To a stirred solution of N4-[(1S)-2-(difluoromethoxy)-1-methyl-ethyl]-7-(3,5-dimethylisoxazol-4-yl)-6-methoxy-quinoline-3,4-diamine (100 mg, 0.255 mmol) in DMF (5 mL) and AcOH (0.62 mL) was added 4,4-difluorocyclohexanecarbaldehyde (114 mg, 0.765 mmol) and the resulting mixture was stirred overnight at room temperature. The mixture was diluted with ethyl acetate and washed with saturated NaHCO$_3$(3×) and brine (1×). The organic phase was dried, filtered and concentrated in vacuo then chromatographed on silica gel eluting with 50-60% EtOAc in hexanes. The product containing fractions were concentrated in vacuo and stirred in diethyl ether and the resulting suspension was filtered to collect the desired product as an off-white solid (30 mg, 23%).

(c) 4-[2-cyclohexyl-1-[(1S)-2-(difluoromethoxy)-1-methyl-ethyl]-8-methoxy-imidazo[4,5-c]quinolin-7-yl]-3,5-dimethyl-isoxazole

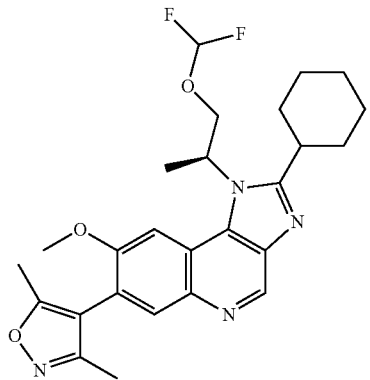 [SMILES: COc1cc2c(cc1-c1c(C)noc1C)ncc1nc(C3CCCCC3)n([C@@H](C)COC(F)F)c12]

To a stirred solution of N4-[(1 S)-2-(difluoromethoxy)-1-methyl-ethyl]-7-(3,5-dimethylisoxazol-4-yl)-6-methoxy-quinoline-3,4-diamine (89.2 mg, 0.227 mmol) in DMF (4.5 mL) and HOAc (0.61 mL) was added tetrahydropyran-4-carbaldehyde (76.5 mg, 0.681 mmol) and the resulting mixture was stirred at room temperature for 2 d. The mixture was diluted with ethyl acetate and washed with saturated NaHCO$_3$(3×) and brine (1×). The organic phase was dried, filtered and concentrated in vacuo then triturated with diethyl ether. The desired product was collected via vacuum filtration (73 mg, 66%).

(d) 4-[2-cyclopentyl-1-[(1 S)-2-(difluoromethoxy)-1-methyl-ethyl]-8-methoxy-imidazo[4,5-c]quinolin-7-yl]-3,5-dimethyl-isoxazole

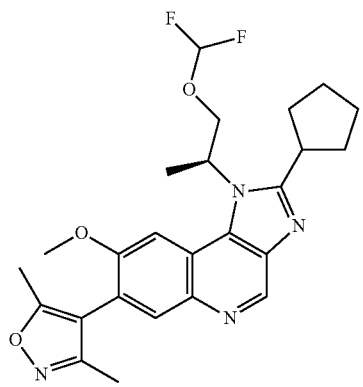 [SMILES: COc1cc2c(cc1-c1c(C)noc1C)ncc1nc(C3CCCC3)n([C@@H](C)COC(F)F)c12]

To a stirred solution of N4-[(1 S)-2-(difluoromethoxy)-1-methyl-ethyl]-7-(3,5-dimethylisoxazol-4-yl)-6-methoxy-quinoline-3,4-diamine (89.2 mg, 0.227 mmol) in DMF (4.5 mL) and HOAc (0.61 mL) was added cyclopentanecarbaldehyde (66.9 mg, 0.681 mmol) and the resulting mixture was stirred at room temperature for 2 d. The mixture was diluted with ethyl acetate and washed with saturated NaHCO$_3$(3×) and brine (1×). The organic phase was dried, filtered and concentrated in vacuo then triturated with diethyl ether/hexanes. The desired product was collected via vacuum filtration (45 mg, 42%).

(e) 4-[2-cyclopropyl-1-[(1 S)-2-(difluoromethoxy)-1-methyl-ethyl]-8-methoxy-imidazo[4,5-c]quinolin-7-yl]-3,5-dimethyl-isoxazole hydrochloride

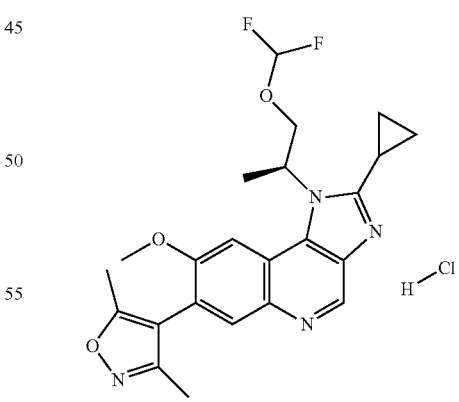

To a stirred solution of N4-[(1 S)-2-(difluoromethoxy)-1-methyl-ethyl]-7-(3,5-dimethylisoxazol-4-yl)-6-methoxy-quinoline-3,4-diamine (89.2 mg, 0.227 mmol) in DMF (4.5 mL) and HOAc (0.61 mL) was added cyclopropanecarbaldehyde (47 mg, 0.681 mmol) and the resulting mixture was stirred at room temperature for 2 d. The mixture was diluted with ethyl acetate and washed with saturated NaHCO$_3$(3×)

and brine (1×). The organic phase was dried, filtered and concentrated in vacuo then chromatographed in 50-80% ethyl acetate in hexanes. The product containing fractions were concentrated in vacuo and treated with HCl, 2 M in diethyl ether (1 eq.). The mixture was stirred with ether and filtered to collect the desired product as a white solid (46 mg, 42%).

(f) 4-[1-[(1 S)-2-(difluoromethoxy)-1-methyl-ethyl]-8-methoxy-2-(2-pyridyl)imidazo[4,5-c]quinolin-7-yl]-3,5-dimethyl-isoxazole

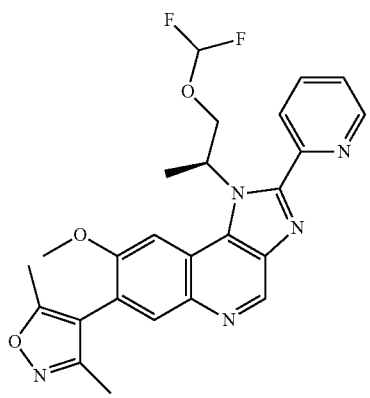 [SMILES: COc1cc2c(cc1-c1c(C)noc1C)ncc1nc(-c3ccccn3)n([C@@H](C)COC(F)F)c12]

To a stirred solution of N4-[(1 S)-2-(difluoromethoxy)-1-methyl-ethyl]-7-(3,5-dimethylisoxazol-4-yl)-6-methoxy-quinoline-3,4-diamine (89.2 mg, 0.227 mmol) in DMF (4.5 mL) and HOAc (0.61 mL) was added pyridine-2-carbaldehyde (73 mg, 0.681 mmol) and the resulting mixture was stirred at 70° C. for 2 h then at room temperature overnight. The mixture was diluted with ethyl acetate and washed with saturated NaHCO$_3$(3×) and brine (1×). The organic phase was dried, filtered and concentrated in vacuo then chromatographed in 0-5% MeOH in ethyl acetate. The product containing fractions were concentrated in vacuo and triturated with diethyl ether. The product was obtained by vacuum filtration as a fine white powder (67 mg, 61%).

(g) 4-[1-[(1R)-2-(difluoromethoxy)-1-methyl-ethyl]-8-methoxy-2-tetrahydropyran-4-yl-imidazo[4,5-c]quinolin-7-yl]-3,5-dimethyl-isoxazole

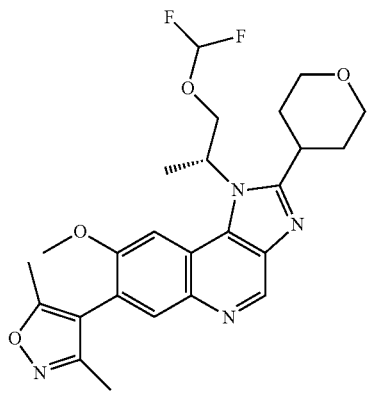 [SMILES: COc1cc2c(cc1-c1c(C)noc1C)ncc1nc(C3CCOCC3)n([C@H](C)COC(F)F)c12]

To a stirred solution of N4-[(1R)-2-(difluoromethoxy)-1-methyl-ethyl]-7-(3,5-dimethylisoxazol-4-yl)-6-methoxy-quinoline-3,4-diamine (100 mg, 0.254 mmol) in DMF 94.5 mL) and AcOH (0.68 mL) was added tetrahydropyran-4-carbaldehyde (87.2 mg, 0.764 mmol) and the resulting mixture was stirred vigorously overnight at room temperature. The mixture was diluted with ethyl acetate and washed with saturated NaHCO$_3$(3×) and brine (1×). The organic phase was dried, filtered and concentrated in vacuo then chromatographed in 50-100% ethyl acetate in hexanes. The product containing fractions were concentrated in vacuo and triturated with hexanes giving the desired product as a white solid, collected via vacuum filtration (48 mg, 39%).

(h) 4-[2-(4,4-difluorocyclohexyl)-1-[(1R)-2-(difluoromethoxy)-1-methyl-ethyl]-8-methoxy-imidazo[4,5-c]quinolin-7-yl]-3,5-dimethyl-isoxazole

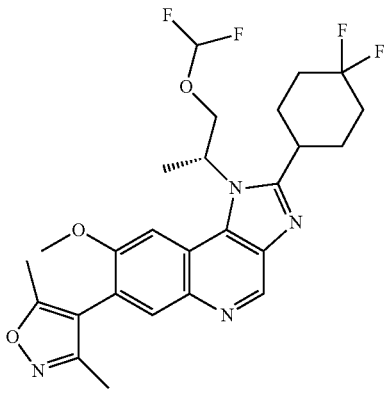 [SMILES: COc1cc2c(cc1-c1c(C)noc1C)ncc1nc(C3CCC(F)(F)CC3)n([C@H](C)COC(F)F)c12]

To a stirred solution of N4-[(1R)-2-(difluoromethoxy)-1-methyl-ethyl]-7-(3,5-dimethylisoxazol-4-yl)-6-methoxy-quinoline-3,4-diamine (100 mg, 0.254 mmol) in DMF 94.5 mL) and AcOH (0.68 mL) was added 4,4-difluorocyclohexanecarbaldehyde (113.2 mg, 0.764 mmol) and the resulting mixture was stirred vigorously overnight at room temperature. The mixture was diluted with ethyl acetate and washed with saturated NaHCO$_3$(3×) and brine (1×). The organic phase was dried, filtered and concentrated in vacuo then chromatographed in 50-100% ethyl acetate in hexanes. The product containing fractions were concentrated in vacuo and triturated with hexanes giving the desired product as a white solid, collected via vacuum filtration (52 mg, 39%).

(i) 4-[1-[(1R)-2-(difluoromethoxy)-1-methyl-ethyl]-8-methoxy-2-(3-pyridyl)imidazo[4,5-c]quinolin-7-yl]-3,5-dimethyl-isoxazole

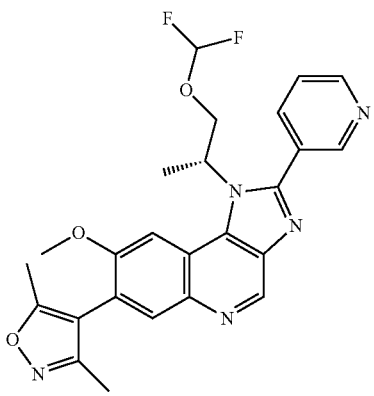 [SMILES: COc1cc2c(cc1-c1c(C)noc1C)ncc1nc(-c3cccnc3)n([C@H](C)COC(F)F)c12]

To a stirred solution of N4-[(1R)-2-(difluoromethoxy)-1-methyl-ethyl]-7-(3,5-dimethylisoxazol-4-yl)-6-methoxy-quinoline-3,4-diamine (100 mg, 0.254 mmol) in DMF 94.5 mL) and AcOH (0.68 mL) was added pyridine-2-carbaldehyde (81.9 mg, 0.764 mmol) and the resulting mixture was stirred vigorously overnight at 70-80° C. The mixture was diluted with ethyl acetate and washed with saturated NaHCO₃(3×) and brine (1×). The organic phase was dried, filtered and concentrated in vacuo then chromatographed in 5% MeOH in ethyl acetate. The product containing fractions were concentrated in vacuo and triturated with diethyl ether giving the desired product as a white solid, collected via vacuum filtration (76 mg, 62%).

(j) 4-[2-cyclohexyl-1-[(1R)-2-(difluoromethoxy)-1-methyl-ethyl]-8-methoxy-imidazo[4,5-c]quinolin-7-yl]-3,5-dimethyl-isoxazole

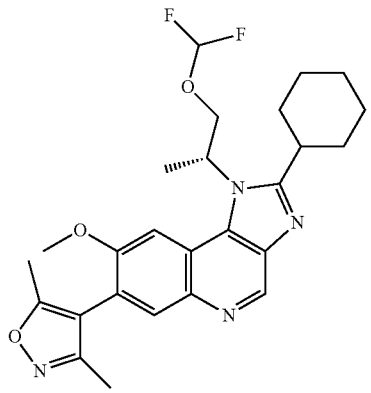

To a stirred solution of N4-[(1R)-2-(difluoromethoxy)-1-methyl-ethyl]-7-(3,5-dimethylisoxazol-4-yl)-6-methoxy-quinoline-3,4-diamine (100 mg, 0.254 mmol) in DMF 94.5 mL) and AcOH (0.68 mL) was added cyclohexanecarbaldehyde (85.7 mg, 0.764 mmol) and the resulting mixture was stirred vigorously overnight at room temperature. The mixture was diluted with ethyl acetate and washed with saturated NaHCO₃(3×) and brine (1×). The organic phase was dried, filtered and concentrated in vacuo then chromatographed in 50-100% ethyl acetate in hexanes. The product containing fractions were concentrated in vacuo and triturated with hexanes giving the desired product as a white solid, collected via vacuum filtration (85 mg, 70%).

(k) 4-[2-cyclopentyl-1-[(1R)-2-(difluoromethoxy)-1-methyl-ethyl]-8-methoxy-imidazo[4,5-c]quinolin-7-yl]-3,5-dimethyl-isoxazole

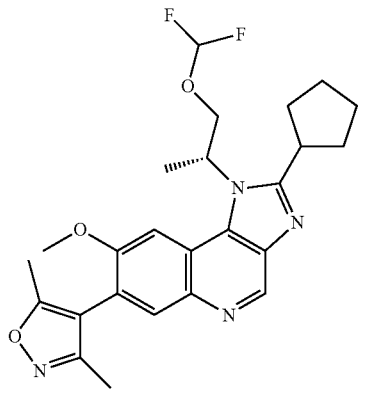 [SMILES: COc1cc2c(cc1-c1c(C)noc1C)ncc1nc(C3CCCC3)n([C@H](C)COC(F)F)c12]

To a stirred solution of N4-[(1R)-2-(difluoromethoxy)-1-methyl-ethyl]-7-(3,5-dimethylisoxazol-4-yl)-6-methoxy-quinoline-3,4-diamine (100 mg, 0.254 mmol) in DMF 94.5 mL) and AcOH (0.68 mL) was added cyclopentanecarbaldehyde (75 mg, 0.764 mmol) and the resulting mixture was stirred vigorously overnight at room temperature. The mixture was diluted with ethyl acetate and washed with saturated NaHCO₃(3×) and brine (1×). The organic phase was dried, filtered and concentrated in vacuo then triturated with hexanes/diethyl ether giving the desired product as a white solid, collected via vacuum filtration (90 mg, 73%).

(l) 4-[2-cyclopropyl-1-[(1R)-2-(difluoromethoxy)-1-methyl-ethyl]-8-methoxy-imidazo[4,5-c]quinolin-7-yl]-3,5-dimethyl-isoxazole hydrochloride

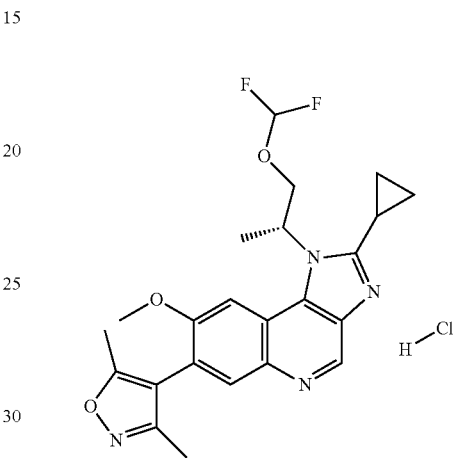

To a stirred solution of N4-[(1R)-2-(difluoromethoxy)-1-methyl-ethyl]-7-(3,5-dimethylisoxazol-4-yl)-6-methoxy-quinoline-3,4-diamine (100 mg, 0.254 mmol) in DMF 94.5 mL) and AcOH (0.68 mL) was added cyclopropylcarbaldehyde (53 mg, 0.764 mmol) and the resulting mixture was stirred vigorously overnight at room temperature. The mixture was diluted with ethyl acetate and washed with saturated NaHCO₃(3×) and brine (1×). The organic phase was dried, filtered and concentrated in vacuo then treated with HCl, 1M in diethyl ether (1 eq.). The resulting mixture was stirred in ether and filtered to collect the desired product as a white, slightly sticky solid (91 mg, 75%).

(m) 4-[1-[(1R)-2-(difluoromethoxy)-1-methyl-ethyl]-8-methoxy-2-(2-pyridyl)imidazo[4,5-c]quinolin-7-yl]-3,5-dimethyl-isoxazole

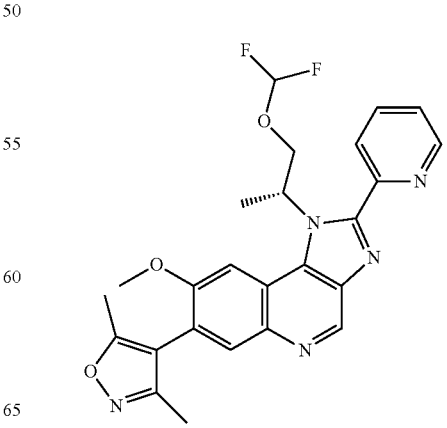

To a stirred solution of N4-[(1R)-2-(difluoromethoxy)-1-methyl-ethyl]-7-(3,5-dimethylisoxazol-4-yl)-6-methoxy-quinoline-3,4-diamine (100 mg, 0.254 mmol) in DMF 94.5 mL) and AcOH (0.68 mL) was added pyridine-2-carbaldehyde (82 mg, 0.764 mmol) and the resulting mixture was stirred vigorously overnight at room temperature. The mixture was diluted with ethyl acetate and washed with saturated NaHCO$_3$(3×) and brine (1×). The organic phase was dried, filtered and concentrated in vacuo then chromatographed in 0-10% MeOH in ethyl acetate. The product containing fractions were concentrated in vacuo and triturated with diethyl ether/hexanes giving the desired product as a white solid, collected via vacuum filtration (33 mg, 27%).

(n) 4-[1-[2-(difluoromethoxy)ethyl]-8-methoxy-2-tetrahydropyran-4-yl-imidazo[4,5-c]quinolin-7-yl]-3,5-dimethyl-isoxazole

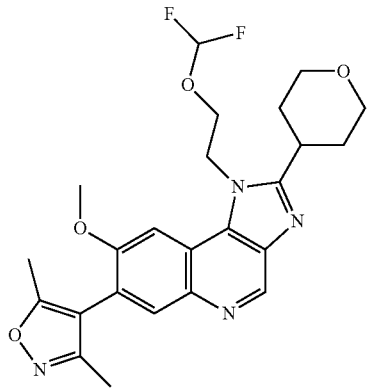 [SMILES: COc1cc2c(cc1-c1c(C)noc1C)ncc1nc(C3CCOCC3)n(CCOC(F)F)c12]

To a stirred solution of N4-[2-(difluoromethoxy)ethyl]-7-(3,5-dimethylisoxazol-4-yl)-6-methoxy-quinoline-3,4-diamine (100 mg, 0.264) in DMF (4.5 mL) and AcOH (0.68 mL) was added tetrahydropyran-4-carbaldehyde (90.5 mg, 0.792 mmol) and the resulting mixture was stirred at 70-80° C. for 2 h then at room temperature overnight. The mixture was The mixture was diluted with ethyl acetate and washed with saturated NaHCO$_3$(3×) and brine (1×). The organic phase was dried, filtered and concentrated in vacuo then triturated with diethyl ether. The resulting suspension was filtered to collect the desired product as a pale off-white solid (70 mg, 56%).

(o) 4-[8-methoxy-2-tetrahydropyran-4-yl-1-(3,3,3-trifluoropropyl)imidazo[4,5-c]quinolin-7-yl]-3,5-dimethyl-isoxazole

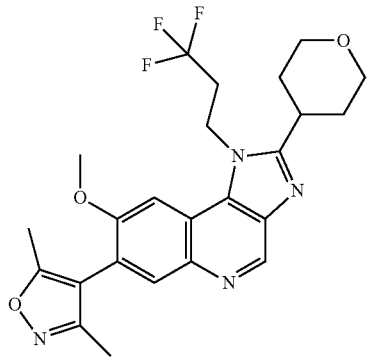 [SMILES: COc1cc2c(cc1-c1c(C)noc1C)ncc1nc(C3CCOCC3)n(CCC(F)(F)F)c12]

To a stirred solution of 7-(3,5-dimethylisoxazol-4-yl)-6-methoxy-N4-(3,3,3-trifluoropropyl)quinoline-3,4-diamine (124 mg, 0.325 mmol) in DMF (4.5 mL) and AcOH (0.86 mL) was added tetrahydropyran-4-carbaldehyde (112 mg, 0.978 mmol) and the resulting mixture was stirred vigorously for 2 d. The mixture was diluted with ethyl acetate and washed with saturated NaHCO$_3$(3×) and brine (1×). The organic phase was dried, filtered and concentrated in vacuo then chromatographed in 50-100% ethyl acetate in hexanes. The product containing fractions were concentrated in vacuo then triturated with diethyl ether to give the desired product as an off-white solid (84 mg, 54%).

(p) 4-[2-(4,4-difluorocyclohexyl)-8-methoxy-1-(3,3,3-trifluoropropyl)imidazo[4,5-c]quinolin-7-yl]-3,5-dimethyl-isoxazole

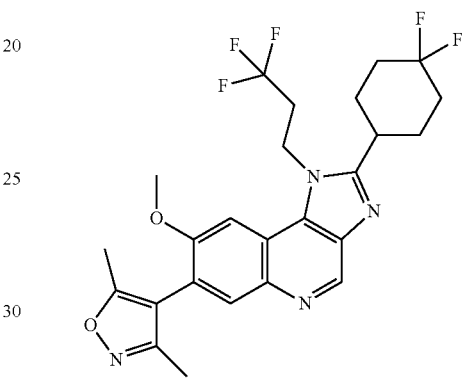

To a stirred solution of 7-(3,5-dimethylisoxazol-4-yl)-6-methoxy-N4-(3,3,3-trifluoropropyl)quinoline-3,4-diamine (124 mg, 0.325 mmol) in DMF (4.5 mL) and AcOH (0.86 mL) was added 4,4-difluorocyclohexanecarbaldehyde (112 mg, 0.978 mmol) and the resulting mixture was stirred vigorously for 2 d. The mixture was diluted with ethyl acetate and washed with saturated NaHCO$_3$(3×) and brine (1×). The organic phase was dried, filtered and concentrated in vacuo then chromatographed in 20-60% ethyl acetate in hexanes. The product containing fractions were concentrated in vacuo then triturated with diethyl ether to give the desired product as an pale yellow solid (104 mg, 63%).

In a like manner, the following additional compounds of the application were prepared using Method A:

2(q)

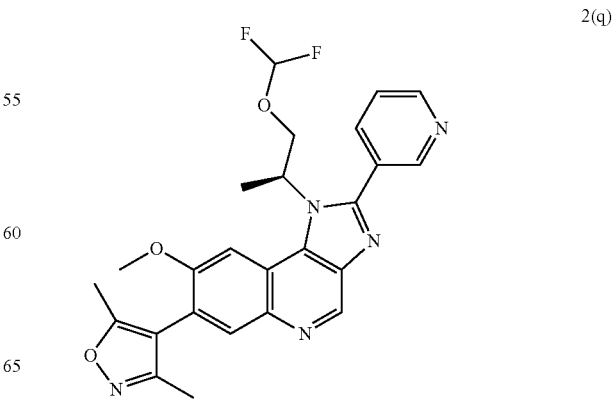

-continued

2(r)

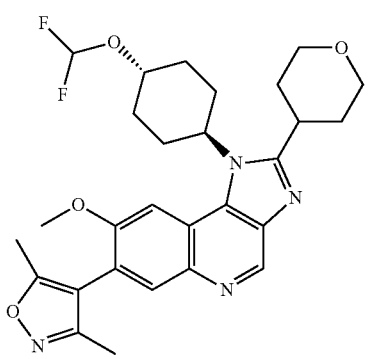

To a stirred solution of N4-[4-(difluoromethoxy)cyclohexyl]-7-(3,5-dimethylisoxazol-4-yl)-6-methoxy-quinoline-3,4-diamine (100 mg, 0.231 mmol) in DMF (5 mL) and AcOH (0.62 mL) was added tetrahydropyran-4-carbaldehyde (91.1 mg, 0.798 mmol) and the resulting mixture was stirred at room temperature overnight. The mixture was diluted with ethyl acetate and washed with saturated NaHCO$_3$(3×) and brine (1×). The organic phase was dried, filtered and concentrated in vacuo then chromatographed in ethyl acetate to give the desired product as an off-white solid (36 mg, 30%).

$^1$H NMR (d6-DMSO 400 MHz) δ 9.06 (s, 1H), 8.02 (s, 1H), 7.70 (s, 1H), 6.82 (t, J=76 Hz, 1H), 5.26 (brs, 1H), 5.01-4.75 (m, 1H), 4.52-4.25 (m, 2H), 4.09 (s, 3H), 4.03-3.97 (m, 2H), 3.67-3.49 (m, 3H), 2.76-2.65 (m, 1H), 2.36 (s, 3H), 2.32-2.20 (m, 2H), 2.17 (s, 3H), 2.15-1.75 (m, 7H).

2(s)

2(t)

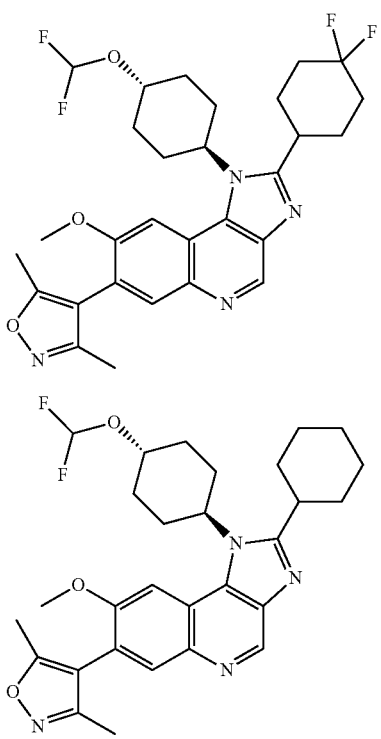

Table 1 provides a summary the $^1$H NMR and LCMS characteristics of representative compounds prepared using Method A.

Example 3: Representative Synthesis of Compounds Using the Chloromethylderivative with Various Amines (Method B)

(a) 4-[[1-[(1R)-2-(difluoromethoxy)-1-methylethyl]-7-(3,5-dimethylisoxazol-4-yl)-8-methoxy-imidazo[4,5-c]quinolin-2-yl]methyl]morpholine trihydrochloride

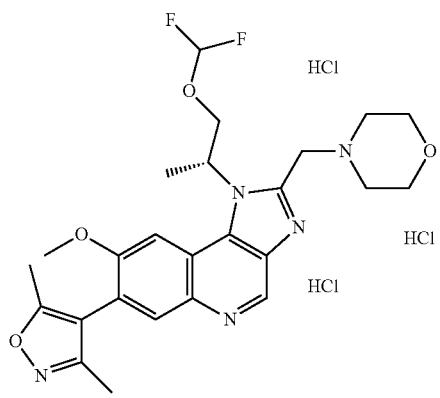 [SMILES: COc1cc2c(cc1-c1c(C)noc1C)ncc1nc(CN3CCOCC3)n([C@H](C)COC(F)F)c12 ; Cl ; Cl ; Cl]

To a stirred solution of 4-[2-(chloromethyl)-1-[(1R)-2-(difluoromethoxy)-1-methyl-ethyl]-8-methoxy-imidazo[4,5-c]quinolin-7-yl]-3,5-dimethyl-isoxazole (80 mg, 0.177 mmol) in ACN (7.5 mL) was added morpholine (90 mg, 1.03 mmol) followed by potassium carbonate (21.6 mg, 0.177 mmol) and the resulting mixture was stirred at room temperature overnight. The resulting mixture was diluted with ethyl acetate and washed with saturated NaHCO$_3$(2×) and brine (1×). The organic phase was dried, filtered and concentrated in vacuo then treated with HCl, 2 M in diethyl ether (0.3 mL). The resulting mixture was concentrated in vacuo and triturated with diethyl ether to give the desired product as an off-white solid (76 mg, 70%).

(b) 1-[1-[(1R)-2-(difluoromethoxy)-1-methyl-ethyl]-7-(3,5-dimethylisoxazol-4-yl)-8-methoxy-imidazo[4,5-c]quinolin-2-yl]-N,N-dimethyl-methanamine

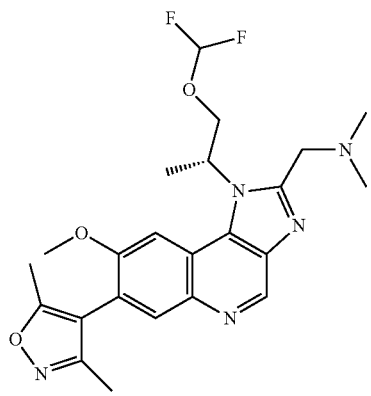 [SMILES: COc1cc2c(cc1-c1c(C)noc1C)ncc1nc(CN(C)C)n([C@H](C)COC(F)F)c12]

To a stirred solution of 4-[2-(chloromethyl)-1-[(1R)-2-(difluoromethoxy)-1-methyl-ethyl]-8-methoxy-imidazo[4,5-c]quinolin-7-yl]-3,5-dimethyl-isoxazole (100 mg, 0.222 mmol) in THF (5 mL) was added dimethylamine, 2 M in THF (1.1 mL, 2.2 mmol) and the resulting mixture was stirred at room temperature overnight. The mixture was diluted with ethyl acetate and washed with saturated NaHCO₃(2×) and brine (1×). The organic phase was dried, filtered and concentrated in vacuo then triturated with diethyl ether/hexanes giving the desired product as an off-white solid (77 mg, 75%).

(c) 4-[1-[(1R)-2-(difluoromethoxy)-1-methyl-ethyl]-8-methoxy-2-(1-piperidylmethyl)imidazo[4,5-c]quinolin-7-yl]-3,5-dimethyl-isoxazole dihydrochloride

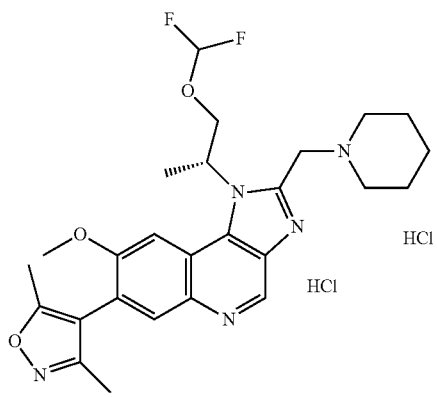 [SMILES: COc1cc2c(cc1-c1c(C)noc1C)ncc1nc(CN3CCCCC3)n([C@H](C)COC(F)F)c12 ; Cl ; Cl]

To a stirred solution of 4-[2-(chloromethyl)-1-[(1R)-2-(difluoromethoxy)-1-methyl-ethyl]-8-methoxy-imidazo[4,5-c]quinolin-7-yl]-3,5-dimethyl-isoxazole (100 mg, 0.222 mmol) in THF (5 mL) was added piperidine (187.3 mg, 2.2 mmol) and the resulting mixture was stirred at room temperature overnight. The mixture was diluted with ethyl acetate and washed with saturated NaHCO₃(2×) and brine (1×). The organic phase was dried, filtered and concentrated in vacuo then treated with HCl, 2 M in diethyl ether. The resulting suspension was filtered to collect the desired product as an off-white solid (23 mg, 18%).

(d) 4-[1-[(1R)-2-(difluoromethoxy)-1-methyl-ethyl]-8-methoxy-2-(pyrrolidin-1-ylmethyl)imidazo[4,5-c]quinolin-7-yl]-3,5-dimethyl-isoxazole dihydrochloride

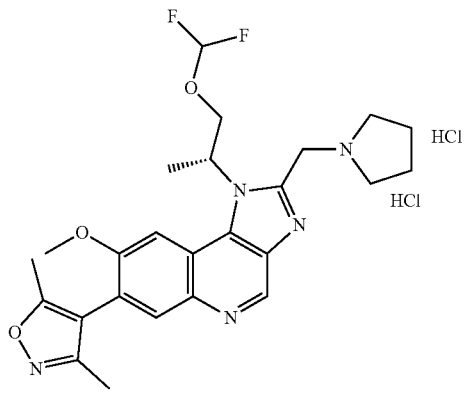 [SMILES: COc1cc2c(cc1-c1c(C)noc1C)ncc1nc(CN3CCCC3)n([C@H](C)COC(F)F)c12 ; Cl ; Cl]

To a stirred solution of 4-[2-(chloromethyl)-1-[(1R)-2-(difluoromethoxy)-1-methyl-ethyl]-8-methoxy-imidazo[4,5-c]quinolin-7-yl]-3,5-dimethyl-isoxazole (100 mg, 0.222 mmol) in THF (5 mL) was added pyrrolidine (156.5 mg, 2.2 mmol) and the resulting mixture was stirred at room temperature overnight. The mixture was diluted with ethyl acetate and washed with saturated NaHCO₃(2×) and brine (1×). The organic phase was dried, filtered and concentrated in vacuo then treated with HCl, 2 M in diethyl ether. The resulting suspension was filtered to collect the desired product as an off-white solid (66 mg, 54%).

(e) 4-[1-[(1R)-2-(difluoromethoxy)-1-methyl-ethyl]-8-methoxy-2-[(4-methylpiperazin-1-yl)methyl]imidazo[4,5-c]quinolin-7-yl]-3,5-dimethyl-isoxazole

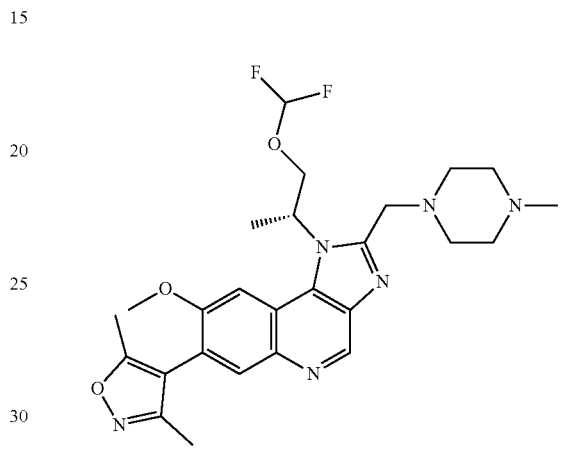

To a stirred solution of 4-[2-(chloromethyl)-1-[(1R)-2-(difluoromethoxy)-1-methyl-ethyl]-8-methoxy-imidazo[4,5-c]quinolin-7-yl]-3,5-dimethyl-isoxazole (100 mg, 0.222 mmol) in THF (5 mL) was added 1-methylpiperazine (200.3 mg, 2.0 mmol) and the resulting mixture was stirred at room temperature overnight. The mixture was diluted with ethyl acetate and washed with saturated NaHCO₃ (2×) and brine (1×). The organic phase was dried, filtered and concentrated in vacuo then triturated with diethyl ether/hexanes giving the desired product as an off-white solid (69 mg, 61%).

(f) 4-[1-[(1R)-2-(difluoromethoxy)-1-methyl-ethyl]-2-[(4,4-difluoro-1-piperidyl)methyl]-8-methoxy-imidazo[4,5-c]quinolin-7-yl]-3,5-dimethyl-isoxazole

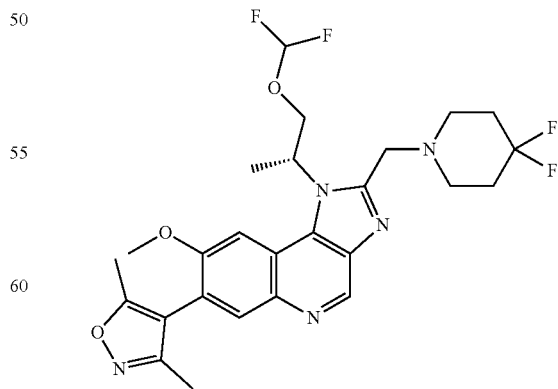

To a stirred solution of 4-[2-(chloromethyl)-1-[(1R)-2-(difluoromethoxy)-1-methyl-ethyl]-8-methoxy-imidazo[4, 5-c]quinolin-7-yl]-3,5-dimethyl-isoxazole (100 mg, 0.222 mmol) in THF (5 mL) was added 4,4-difluoropiperidine hydrochloride (175 mg, 1.1 mmol) followed by potassium carbonate (184 mg, 1.33 mmol) and triethylamine (0.2 mL, 1.43 mmol). The resulting mixture was 70° C. for 6 h. The mixture was diluted with ethyl acetate and washed with saturated NaHCO₃ (2×) and brine (1×). The organic phase was dried, filtered and concentrated in vacuo then triturated with diethyl ether/hexanes giving the desired product as an off-white solid (74 mg, 59%).

In a like manner, the following additional compounds of the application were prepared using Method B:

3(g)

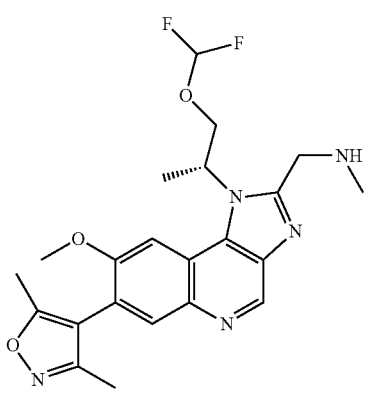

3(h)

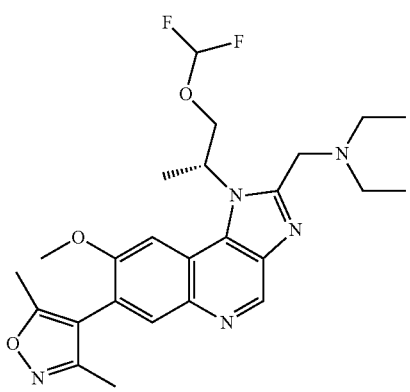

3(i)

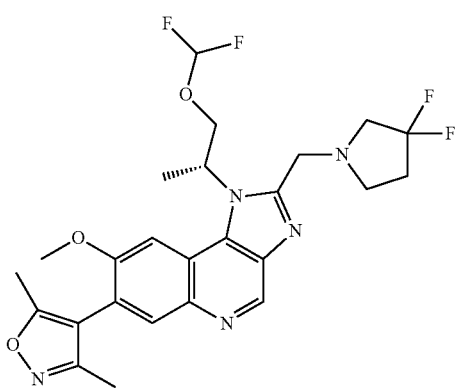

3(j)

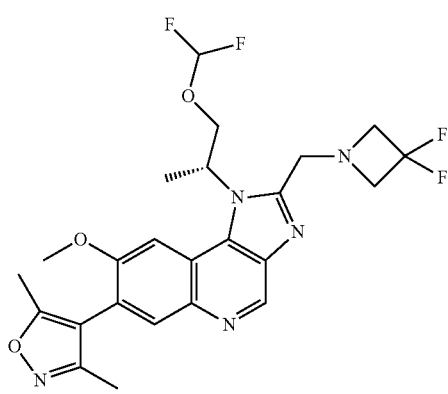

Table 2 provides a summary the ¹H NMR and LCMS characteristics of representative compounds prepared from the reaction of intermediate I (Scheme II) with various amines using Method B.

Example 4: Preparation of Intermediates (a) tert-butyl N-(2-hydroxyethyl)carbamate

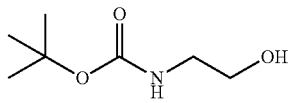

To a stirred solution of ethanolamine (5 g, 4.94 mL, 81.8 mmol) and sodium hydroxide (327 mg, 8.18 mmol) in water (30 mL) was added di-tert-butyl dicarbonate (19.65 g, 90.0 mmol) as a solution in tetrahydrofuran (30 mL). The mixture was stirred overnight at room temperature (mild exotherm, steady bubbling observed). The mixture was diluted with diethyl ether and washed with brine (2×), water (2×) and brine (1×). The organic phase was dried, filtered and concentrated in vacuo then chromatographed in 25-75% ethyl acetate in hexanes. The product containing fractions were concentrated in vacuo giving a thick colourless syrup (11.06 g, 83%).

(b) O-[2-(tert-butoxycarbonylamino)ethyl]methanethioate

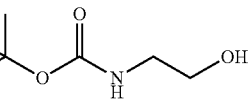

To a stirred solution of DMF (4.80 mL, 62.0 mmol) in DCM (75 mL) cooled to −20° C. under nitrogen was added oxalyl chloride (5.32 mL, 62.0 mmol) slowly over a period of 30 min (bubbling observed). The mixture was stirred for a further 15 min then treated with tert-butyl N-(2-hydroxyethyl)carbamate (5 g, 31.0 mmol) as a solution in DCM (10 mL). The mixture was stirred for a further 10 min (at −20° C.) then treated with NaHS (7.4 g) as a solution in water (10 mL, quickly, with vigorous stirring) then warmed to room temperature. The mixture was diluted with water and the organic phase was washed with water (1×) and brine (1×). The organic phase was dried, filtered and concentrated in vacuo then chromatographed in 0-15% ethyl acetate in hexanes. The product containing fractions were concentrated in vacuo giving a yellow oil (5.36 g, 84%). ¹H NMR (CDCl₃, 300 MHz) δ 9.72 (s, 1H), 4.80 (brs, 1H), 4.59-4.55 (m, 2H), 3.60-3.51 (m, 2H), 1.45 (s, 9H).

(c) tert-butyl N-[2-(difluoromethoxy)ethyl]carbamate

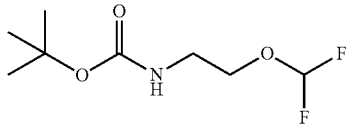

2-chloro-1,3-dimethyl-4,5-dihydroimidazol-1-ium chloride (8.5 g, 50 mmol) and KF (12.8 g, 220 mmol) were combined with ACN (100 mL) and stirred at reflux temperature overnight. The mixture was then cooled to room temperature and treated with O-[2-(tert-butoxycarbonylamino)ethyl] methanethioate (5.3 g, 25.8 mmol) as a solution in DCM (10 mL). The resulting mixture was stirred for 2 h. The mixture was diluted with diethyl ether and washed with brine (2×) water (2×) and brine (1×). The organic phase was dried, filtered and concentrated in vacuo then chromatographed in 0-30% ethyl acetate in hexanes. The product containing fractions were concentrated in vacuo giving the desired product as a clear oil (5.1 g, 93%). ¹H NMR (d6-DMSO, 300 MHz) δ 6.81, (brs, 1H), 6.62 (t, J=75 Hz, 1H), 3.75-3.54 (m, 4H), 1.37 (s, 9H).

(d) 2-(difluoromethoxy)ethanamine hydrochloride

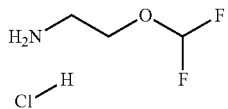

To a stirred solution of tert-butyl N-[2-(difluoromethoxy)ethyl]carbamate (5.1 g, 24.1 mmol) in DCM (10 mL) was added TFA (10 mL). The resulting mixture was stirred at room temperature for 1 h (bubbling observed). The mixture was concentrated in vacuo and stirred with HCl, 2 M in diethyl ether (1 eq.). The resulting suspension was stirred in diethyl ether and filtered to collect the desired product as a white solid (3.5 g, 98%, slightly hygroscopic). ¹H NMR (d6-DMSO, 300 MHz) δ 8.11 (brs, 3H), 6.74 (t, J=75 Hz, 1H), 3.99-3.80 (m, 2H), 3.56-3.33 (m, 2H).

(e) tert-butyl N-[(1R)-2-hydroxy-1-methyl-ethyl]carbamate

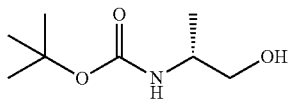

To a stirred solution of D-alaninol (9.5 g, 126 mmol) and sodium hydroxide (506 mg, 12.6 mmol) in water (100 mL) was added di-tert-butyl dicarbonate (30.3 g, 139 mmol) as a solution in THF (100 mL). The resulting mixture was stirred at room temperature overnight (steady bubbling observed). The mixture was diluted with diethyl ether and washed with brine (2×), water (2×) and brine (1×). The organic phase was dried, filtered and concentrated in vacuo. The residue was stirred in hexanes. The resulting suspension was filtered to collect the desired product as a white solid (18.56 g, 84%).

(f) O-[(2R)-2-(tert-butoxycarbonylamino)propyl] methanethioate

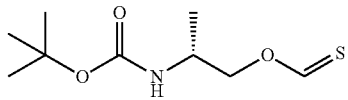

To a stirred solution of DMF (4.42 mL, 57.1 mmol) in DCM (50 mL) cooled to −20° C. under nitrogen was added oxalyl chloride (4.89 mL, 57.1 mmol) slowly over a period of 30 min (bubbling observed). The mixture was stirred for a further 15 min then treated with tert-butyl N-[(1R)-2-hydroxy-1-methyl-ethyl]carbamate (5 g, 28.5 mmol) as a solution in DCM (10 mL). The mixture was stirred for a further 10 min (at −20° C.) then treated with NaHS (6 g) as a solution in water (10 mL, quickly, with vigorous stirring) then warmed to room temperature. The mixture was diluted with water and the organic phase was washed with water (1×) and brine (1×). The organic phase was dried, filtered and concentrated in vacuo then chromatographed in 0-15% ethyl acetate in hexanes. The product containing fractions were concentrated in vacuo giving a yellow oil which slowly solidified (5.34 g, 85%). ¹H NMR (CDCl₃, 300 MHz) δ 9.74 (s, 1H), 4.56 (brs, 1H), 4.49-4.42 (m, 2H), 4.20-4.10 (m, 1H), 1.45 (s, 9H), 1.24 (d, J=3 Hz, 3H).

(g) tert-butyl N-[(1R)-2-(difluoromethoxy)-1-methyl-ethyl]carbamate

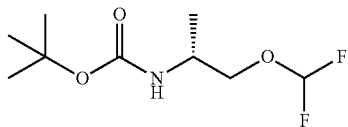

2-chloro-1,3-dimethyl-4,5-dihydroimidazol-1-ium chloride (8.5 g, 50 mmol) and KF (12.8 g, 220 mmol) were combined with ACN (100 mL) and stirred at reflux temperature overnight. The mixture was then cooled to room temperature and treated with O-[2-(tert-butoxycarbonylamino)ethyl] methanethioate (5.3 g, 24.1 mmol) as a solution in DCM (10 mL). The resulting mixture was stirred for 2 h. The mixture was diluted with diethyl ether and washed with brine (2×) water (2×) and brine (1×). The organic phase was dried, filtered and concentrated in vacuo then chromatographed in 0-30% ethyl acetate in hexanes. The product containing fractions were concentrated in vacuo giving the desired product as a clear oil (5.36 g, 98%). ¹H NMR (d6-DMSO, 300 MHz) δ 6.83, (brs, 1H), 6.63 (t, J=76 Hz, 1H), 3.70-3.55 (m, 3H), 1.36 (s, 9H), 1.01 (d, J=3 Hz, 3H).

(h) (2R)-1-(difluoromethoxy)propan-2-amine hydrochloride

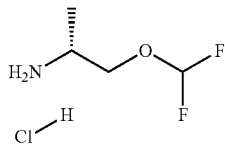

To a stirred solution of tert-butyl N-[(1R)-2-(difluoromethoxy)-1-methyl-ethyl]Carbamate (5.36 g, 23.6 mmol) in DCM (10 mL) was added trifluoroacetic acid (10 mL). The resulting mixture was stirred at room temperature for 1 h (steady bubbling observed). The mixture was concentrated in vacuo and stirred with HCl, 2M in diethyl ether (1 eq.). The resulting suspension was stirred with diethyl ether and filtered to collect the desired product as a white solid (3.42 g, 89%, slightly hygroscopic). $^1$H NMR (d6-DMSO, 300 MHz) δ 8.19 (brs, 3H), 6.75 (t, J=75 Hz, 1H), 3.99-3.90 (m, 1H), 3.89-3.81 (m, 1H), 3.49-3.33 (m, 1H), 1.18 (d, J=6 Hz, 3H).

(i) tert-butyl N-[(1 S)-2-(difluoromethoxy)-1-methyl-ethyl]carbamate

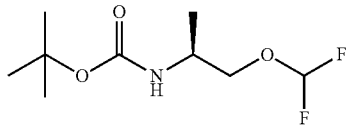

2-Chloro-1,3-dimethyl-4,5-dihydroimidazol-1-ium chloride (8.5 g, 50 mmol) and KF (12.8 g, 220 mmol) were combined with ACN (100 mL) and stirred at reflux temperature overnight. The mixture was then cooled to room temperature and treated with O-[(2S)-2-(tert-butoxycarbonylamino)propyl] methanethioate (5 g, 22.7 mmol) as a solution in DCM (10 mL). The resulting mixture was stirred for 2 h. The mixture was diluted with diethyl ether and washed with brine (2×) water (2×) and brine (1×). The organic phase was dried, filtered and concentrated in vacuo then chromatographed in 0-30% ethyl acetate in hexanes. The product containing fractions were concentrated in vacuo giving the desired product as a clear oil (5.01 g, 97%). 1H NMR (d6-DMSO, 300 MHz) δ 6.83, (brs, 1H), 6.63 (t, J=76 Hz, 1H), 3.70-3.55 (m, 3H), 1.36 (s, 9H), 1.01 (d, J=3 Hz, 3H).

(j) (2S)-1-(difluoromethoxy)propan-2-amine hydrochloride

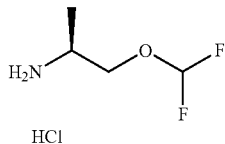

To a stirred solution of tert-butyl N-[(1R)-2-(difluoromethoxy)-1-methyl-ethyl]Carbamate (5.36 g, 23.6 mmol) in DCM (10 mL) was added trifluoroacetic acid (10 mL). The resulting mixture was stirred at room temperature for 1 h (steady bubbling observed). The mixture was concentrated in vacuo and stirred with HCl, 2M in diethyl ether (1 eq.). The resulting suspension was stirred with diethyl ether and filtered to collect the desired product as a white solid (3.42 g, 89%, slightly hygroscopic). $^1$H NMR (d6-DMSO, 300 MHz) δ 8.19 (brs, 3H), 6.75 (t, J=75 Hz, 1H), 3.99-3.90 (m, 1H), 3.89-3.81 (m, 1H), 3.49-3.33 (m, 1H), 1.18 (d, J=6 Hz, 3H).

(k) 7-(3,5-dimethylisoxazol-4-yl)-6-methoxy-3-nitro-N-(3,3,3-trifluoropropyl)quinolin-4-amine

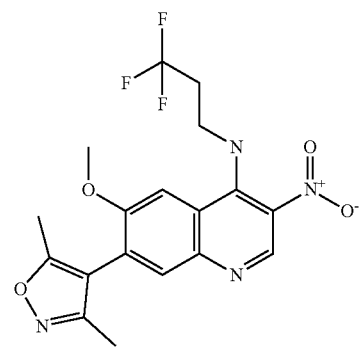 [SMILES: COc1cc2c(NCCC(F)(F)F)c([N+](=O)[O-])cnc2cc1-c1c(C)noc1C]

To a stirred solution of 4-(4-chloro-6-methoxy-3-nitro-7-quinolyl)-3,5-dimethyl-isoxazole (400 mg, 1.198 mmol) in DCM (5 mL) was added 3,3,3-trifluoropropan-1-amine (176 µL, 1.797 mmol) followed by triethylamine (334 µL, 2.397 mmol). The resulting mixture was stirred at room temperature for 3 h. The mixture was diluted with diethyl ether and washed with saturated NaHCO$_3$(2×) and brine (1×). The organic phase was dried, filtered and concentrated giving the desired product as a yellow/orange solid (491 mg, quantitative). $^1$H NMR (d6-DMSO, 300 MHz) δ 8.92 (s, 1H), 8.45 (brs, 1H), 7.82-7.78 (m, 2H), 3.95 (s, 3H), 3.72-3.62 (m, 2H), 2.89-2.72 (m, 2H), 2.31 (s, 3H), 2.12 (m, 3H).

(l) 7-(3,5-dimethylisoxazol-4-yl)-6-methoxy-N4-(3,3,3-trifluoropropyl)quinoline-3,4-diamine

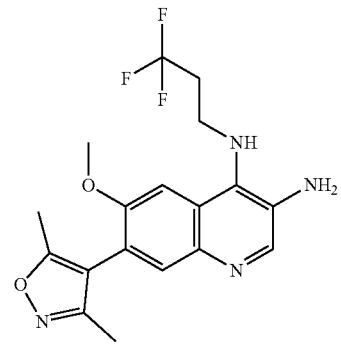 [SMILES: COc1cc2c(NCCC(F)(F)F)c(N)cnc2cc1-c1c(C)noc1C]

To a stirred solution on 7-(3,5-dimethylisoxazol-4-yl)-6-methoxy-3-nitro-N-(3,3,3-trifluoropropyl)quinolin-4-amine (488 mg, 1.19 mmol) in THF (10 mL) was added palladium, 10 wt. % on activated carbon (126 mg, 0.119 mmol). The resulting mixture was stirred overnight under an atmosphere of hydrogen (balloon pressure). The mixture was concentrated onto silica gel and chromatographed in 50-100% ethyl acetate in hexanes. The product containing fractions were concentrated in vacuo giving the desired product as a yellow oil which slowly solidified (250 mg, 55%). $^1$H NMR (d6-DMSO, 300 MHz) δ 8.29 (s, 1H), 7.56 (s, 1H), 7.40 (s, 1H), 5.17 (brs, 2H), 4.88 (t, J=7.5 Hz, 1H), 3.87 (s, 3H), 3.38-3.27 (m, 2H), 2.59-2.49 (m, 2H), 2.27 (s, 3H), 2.08 (s, 3H).

(m) N-[2-(difluoromethoxy)ethyl]-7-(3,5-dimethyl-isoxazol-4-yl)-6-methoxy-3-nitro-quinolin-4-amine

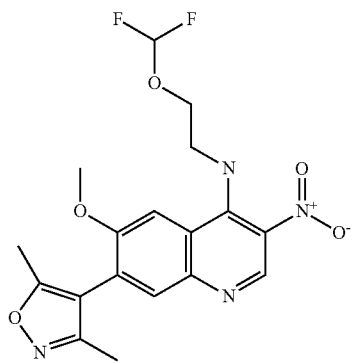 [SMILES: COc1cc2c(NCCOC(F)F)c([N+](=O)[O-])cnc2cc1-c1c(C)noc1C]

To a stirred solution of 4-(4-chloro-6-methoxy-3-nitro-7-quinolyl)-3,5-dimethyl-isoxazole (1 g, 2.99 mmol) in DCM (15 mL) was added 2-(difluoromethoxy)ethanamine hydrochloride (486 mg, 3.29 mmol) followed by triethylamine (1.25 mL, 8.98 mmol). The resulting mixture was stirred at room temperature overnight. The mixture was diluted with EtOAc and washed with brine (2×). The organic phase was dried, filtered and concentrated in vacuo. The residue was stirred in diethyl ether and hexanes and the resulting suspension was filtered to collect the desired product as a yellow solid (1.12 g, 92%). $^1$H NMR (d6-DMSO, 300 MHz) δ 8.96 (s, 1H), 8.69 (m, 1H), 7.84 (s, 1H), 7.80 (s, 1H), 6.70 (t, J=6.70 (t, J=75 Hz, 1H), 4.14 (t, J=4.5 Hz, 2H), 3.95 (s, 3H), 3.88-3.80 (m, 2H), 2.32 (s, 3H), 2.12 (s, 3H).

(n) N4-[2-(difluoromethoxy)ethyl]-7-(3,5-dimethyl-isoxazol-4-yl)-6-methoxy-quinoline-3,4-diamine

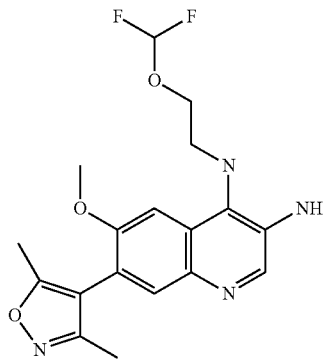 [SMILES: COc1cc2c(NCCOC(F)F)c(N)cnc2cc1-c1c(C)noc1C]

To a stirred solution of N-[2-(difluoromethoxy)ethyl]-7-(3,5-dimethylisoxazol-4-yl)-6-methoxy-3-nitro-quinolin-4-amine (1.12 g, 2.74 mmol) in THF (10 mL) was added palladium, 10 wt. % on activated carbon (290 mg, 0.274 mmol). The resulting mixture was stirred overnight under an atmosphere of hydrogen (balloon pressure). The mixture was concentrated onto silica gel and chromatographed in 50-100% ethyl acetate in hexanes. The product containing fractions were concentrated in vacuo giving the desired product as a yellow oil which slowly solidified (0.42 g, 41%). $^1$H NMR (d6-DMSO, 300 MHz) δ 8.28 (s, 1H), 7.54 (s, 1H), 7u.43 (s, 1H), 6.69 (t, J=75 Hz, 1H), 5.13 (s, 2H), 4.89 (t, J=7.5 Hz, 1H), 3.93-3.85 (m, 2H), 3.87 (s, 3H), 3.42-3.31 (m, 2H), 2.27 (s, 3H), 2.08 (s, 3H).

(o) N-[(1 S)-2-(difluoromethoxy)-1-methyl-ethyl]-7-(3,5-dimethylisoxazol-4-yl)-6-methoxy-3-nitro-quinolin-4-amine

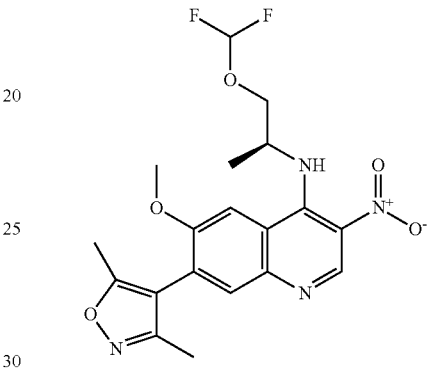

To a stirred solution of 4-(4-chloro-6-methoxy-3-nitro-7-quinolyl)-3,5-dimethyl-isoxazole (1 g, 2.99 mmol) in DCM (10 mL) was added (2S)-1-(difluoromethoxy)propan-2-amine hydrochloride (727 mg, 4.5 mmol) followed by triethylamine (1.25 mL, 9.0 mmol) and the resulting mixture was stirred at room temperature overnight. The mixture was diluted with DCM and washed with water and brine. The organic phase was dried, filtered and concentrated in vacuo. The residue was stirred in diethyl ether giving a suspension which was filtered to collect the desired product as a yellow solid (1.1 g, 94%). $^1$H NMR (d6-DMSO, 300 MHz) δ 9.00 (s, 1H), 8.31 (d, J=12 Hz, 1H), 7.82 (s, 1H), 7.72 (s, 1H), 6.65 (t, J=75 Hz, 1H), 4.42-4.26 (m, 1H), 4.11-3.97 (m, 2H), 3.96 (s, 3H), 2.32 (s, 3H), 2.13 (s, 1H), 1.42 (d, J=6 Hz, 3H).

(p) N4-[(1 S)-2-(difluoromethoxy)-1-methyl-ethyl]-7-(3,5-dimethylisoxazol-4-yl)-6-methoxy-quinoline-3,4-diamine

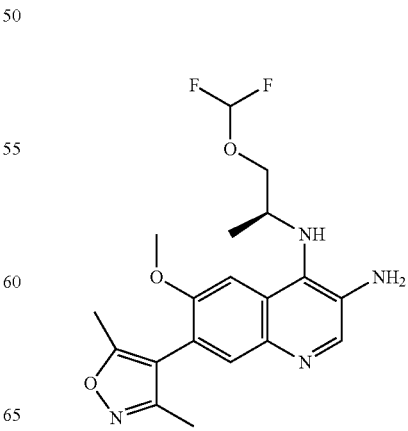

To a stirred solution of N-[(1S)-2-(difluoromethoxy)-1-methyl-ethyl]-7-(3,5-dimethylisoxazol-4-yl)-6-methoxy-3-nitro-quinolin-4-amine (1.1 g, 2.6 mmol) in THF (20 mL) was added palladium, 10 wt. % on activated carbon (220 mg) and the resulting mixture was stirred under an atmosphere of hydrogen (balloon pressure). The resulting mixture was filtered then chromatographed in 50-80% ethyl acetate in hexanes. The product containing fractions were concentrated in vacuo giving the desired product (700 mg, 69%). $^1$H NMR (d6-DMSO, 300 MHz) δ 8.29 (s, 1H), 7.55 (s, 1H), 7.40 (s, 1H), 6.70 (t, J=76 Hz, 1H), 5.15 (s, 2H), 4.60 (d, J=6 Hz, 1H), 3.86 (s, 3H), 3.88-3.73 (m, 2H), 3.70-3.53 (m, 1H), 2.28 (s, 3H), 2.08 (s, 3H), 1.17 (d, J=6 Hz, 3H).

(q) N-[(1R)-2-(difluoromethoxy)-1-methyl-ethyl]-7-(3,5-dimethylisoxazol-4-yl)-6-methoxy-3-nitro-quinolin-4-amine

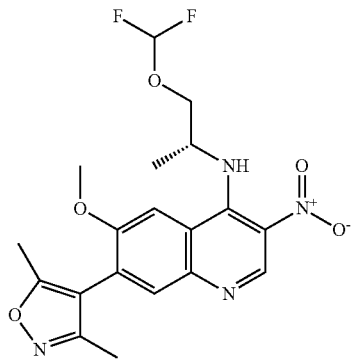 [SMILES: COc1cc2c(N[C@H](C)COC(F)F)c([N+](=O)[O-])cnc2cc1-c1c(C)noc1C]

To a stirred solution of 4-(4-chloro-6-methoxy-3-nitro-7-quinolyl)-3,5-dimethyl-isoxazole (1 g, 2.99 mmol) in DCM (10 mL) was added (2R)-1-(difluoromethoxy)propan-2-amine hydrochloride (727 mg, 4.5 mmol) followed by triethylamine (1.25 mL, 9.0 mmol) and the resulting mixture was stirred at room temperature overnight. The mixture was diluted with DCM and washed with water and brine. The organic phase was dried, filtered and concentrated in vacuo. The residue was stirred in diethyl ether and hexanes giving a suspension which was filtered to collect the desired product as a yellow solid (1.2 g, 95%). $^1$H NMR (d6-DMSO, 300 MHz) δ 9.00 (s, 1H), 8.31 (d, J=12 Hz, 1H), 7.81 (s, 1H), 7.72 (s, 1H), 6.65 (t, J=75 Hz, 1H), 4.40-4.26 (m, 1H), 4.12-3.97 (m, 2H), 3.96 (s, 3H), 2.32 (s, 3H), 2.12 (s, 1H), 1.42 (d, J=6 Hz, 3H).

(r) N4-[(1R)-2-(difluoromethoxy)-1-methyl-ethyl]-7-(3,5-dimethylisoxazol-4-yl)-6-methoxy-quinoline-3,4-diamine

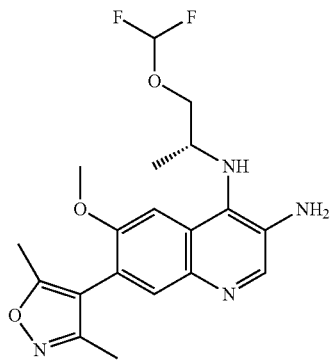 [SMILES: COc1cc2c(N[C@H](C)COC(F)F)c(N)cnc2cc1-c1c(C)noc1C]

To a stirred solution of N-[(1R)-2-(difluoromethoxy)-1-methyl-ethyl]-7-(3,5-dimethylisoxazol-4-yl)-6-methoxy-3-nitro-quinolin-4-amine (1.2 g, 2.8 mmol) in THF (20 mL) was added palladium, 10 wt. % on activated carbon (300 mg) and the resulting mixture was stirred under an atmosphere of hydrogen (balloon pressure). The resulting mixture was filtered then chromatographed in 50-80% ethyl acetate in hexanes. The product containing fractions were concentrated in vacuo giving the desired product (1.05 g, 95%). $^1$H NMR (d6-DMSO, 300 MHz) δ 8.29 (s, 1H), 7.55 (s, 1H), 7.40 (s, 1H), 6.70 (t, J=76 Hz, 1H), 5.15 (s, 2H), 4.60 (d, J=12 Hz, 1H), 3.86 (s, 3H), 3.88-3.73 (m, 2H), 3.70-3.53 (m, 1H), 2.28 (s, 3H), 2.08 (s, 3H), 1.17 (d, J=6 Hz, 3H).

(s) 7-(3,5-dimethylisoxazol-4-yl)-6-methoxy-N-[(1S)-2-methoxy-1-methyl-ethyl]-3-nitro-quinolin-4-amine

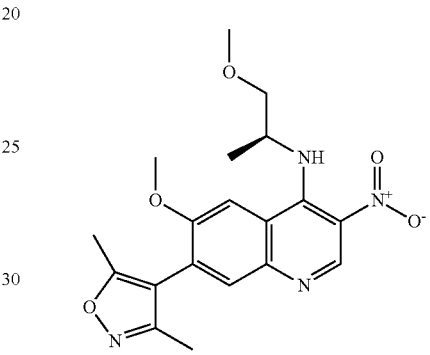

To a stirred solution of 4-(4-chloro-6-methoxy-3-nitro-7-quinolyl)-3,5-dimethyl-isoxazole (1 g, 2.99 mmol) in DCM (10 mL) was added (2S)-1-methoxypropan-2-amine (0.81 mg, 9.0 mmol) followed by triethylamine (0.626 mL, 4.5 mmol) and the resulting mixture was stirred at room temperature for 4 h. The mixture was concentrated in vacuo then stirred with water and hexanes. The mixture was filtered to collect the pale yellow solid which was washed with ether/hexanes giving the desired product (1.16 g, quantitative). $^1$H NMR (d6-DMSO, 300 MHz) δ 9.02 (s, 1H), 8.62 (d, J=9 Hz, 1H), 7.83-7.78 (m, 2H), 4.42-4.28 (m, 1H), 3.95 (s, 3H), 3.57-3.46 (m, 2H), 3.24 (s, 3H), 2.32 (s, 3H), 2.13 (s, 3H), 1.39 (d, J=6 Hz, 3H).

(t) (2R)-2-[[7-(3,5-dimethylisoxazol-4-yl)-6-methoxy-3-nitro-4-quinolyl]amino]propan-1-ol

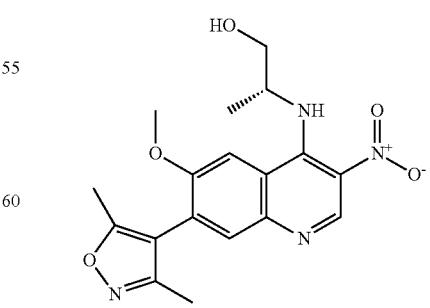

To a stirred solution of 4-(4-chloro-6-methoxy-3-nitro-7-quinolyl)-3,5-dimethyl-isoxazole (250 mg, 0.75 mmol) in DCM (5 mL) was added D-alaninol (225 mg, 3.0 mmol) and the resulting mixture was stirred at room temperature overnight. The mixture was diluted with DCM and washed with water (3×) and brine (1×). The organic phase was dried, filtered and concentrated in vacuo. The residue was stirred with diethyl ether and the resulting suspension was filtered to collect the desired product (258 mg, 92%). $^1$H NMR (d6-DMSO, 300 MHz) δ 9.01 (s, 1H), 8.82 (d, J=9 Hz, 1H), 7.83 (s, 1H), 7.79 (s, 1H), 5.16 (t, J=6 Hz, 1H), 4.33-4.22 (m, 1H), 3.95 (s, 3H), 3.60-3.51 (m, 2H), 2.32 (s, 3H), 2.13 (s, 3H), 1.39 (d, J=6 Hz, 3H).

(u) (2R)-2-[[3-amino-7-(3,5-dimethylisoxazol-4-yl)-6-methoxy-4-quinolyl]amino]propan-1-ol

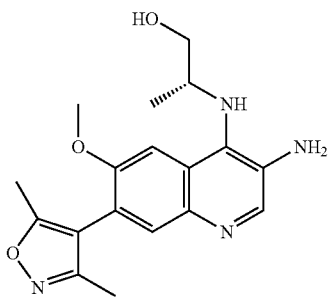 [SMILES: COc1cc2c(N[C@H](C)CO)c(N)cnc2cc1-c1c(C)noc1C]

To a stirred solution of (2R)-2-[[7-(3,5-dimethylisoxazol-4-yl)-6-methoxy-3-nitro-4-quinolyl]amino]propan-1-ol (258 mg, 0.693 mmol) in THF (10 mL) was added palladium, 10 wt. % on activated carbon (60 mg) and the resulting suspension was stirred under an atmosphere of hydrogen (balloon pressure) overnight. The mixture was filtered through a pad of celite and concentrated in vacuo giving the desired product (248 mg, quantitative). $^1$H NMR (d6-DMSO, 300 MHz) δ 8.26 (s, 1H), 7.53 (s, 1H), 7.45 (s, 1H), 5.17 (s, 2H), 4.87 (t, J=4.5 Hz, 1H), 4.36 (d, J=6 Hz, 1H), 3.86 (s, 3H), 3.61-3.56 (m, 1H), 3.46-3.34 (m, 2H), 2.28 (s, 3H), 2.09 (s, 3H), 1.13 (d, J=6 Hz, 3H).

(v) (2S)-2-[[7-(3,5-dimethylisoxazol-4-yl)-6-methoxy-3-nitro-4-quinolyl]amino]propan-1-ol

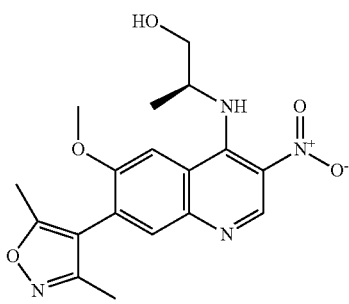 [SMILES: COc1cc2c(N[C@@H](C)CO)c([N+](=O)[O-])cnc2cc1-c1c(C)noc1C]

To a stirred solution of 4-(4-chloro-6-methoxy-3-nitro-7-quinolyl)-3,5-dimethyl-isoxazole (250 mg, 0.75 mmol) in DCM (5 mL) was added L-alaninol (225 mg, 3.0 mmol) and the resulting mixture was stirred at room temperature overnight. The mixture was diluted with DCM and washed with water (3×) and brine (1×). The organic phase was dried, filtered and concentrated in vacuo. The residue was stirred with diethyl ether and the resulting suspension was filtered to collect the desired product (258 mg, 92%). $^1$H NMR (d6-DMSO, 300 MHz) δ 9.01 (s, 1H), 8.82 (d, J=9 Hz, 1H), 7.83 (s, 1H), 7.79 (s, 1H), 5.16 (t, J=6 Hz, 1H), 4.33-4.22 (m, 1H), 3.95 (s, 3H), 3.60-3.51 (m, 2H), 2.32 (s, 3H), 2.13 (s, 3H), 1.39 (d, J=6 Hz, 3H).

(w) (2S)-2-[[3-amino-7-(3,5-dimethylisoxazol-4-yl)-6-methoxy-4-quinolyl]amino]propan-1-ol

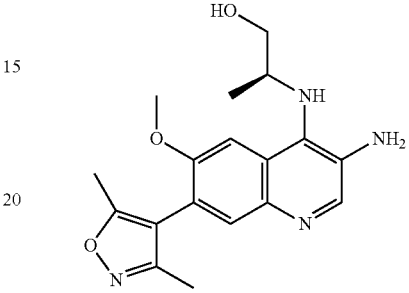

To a stirred solution of (2S)-2-[[7-(3,5-dimethylisoxazol-4-yl)-6-methoxy-3-nitro-4-quinolyl]amino]propan-1-ol (258 mg, 0.693 mmol) in THF (10 mL) was added palladium, 10 wt. % on activated carbon (60 mg) and the resulting suspension was stirred under an atmosphere of hydrogen (balloon pressure) overnight. The mixture was filtered through a pad of celite and concentrated in vacuo giving the desired product (248 mg, quantitative). $^1$H NMR (d6-DMSO, 300 MHz) δ 8.26 (s, 1H), 7.53 (s, 1H), 7.45 (s, 1H), 5.17 (s, 2H), 4.87 (t, J=4.5 Hz, 1H), 4.36 (d, J=6 Hz, 1H), 3.86 (s, 3H), 3.61-3.56 (m, 1H), 3.46-3.34 (m, 2H), 2.28 (s, 3H), 2.09 (s, 3H), 1.13 (d, J=6 Hz, 3H).

(x) 4-[2-(chloromethyl)-1-[(1R)-2-(difluoromethoxy)-1-methyl-ethyl]-8-methoxy-imidazo[4,5-c]quinolin-7-yl]-3,5-dimethyl-isoxazole

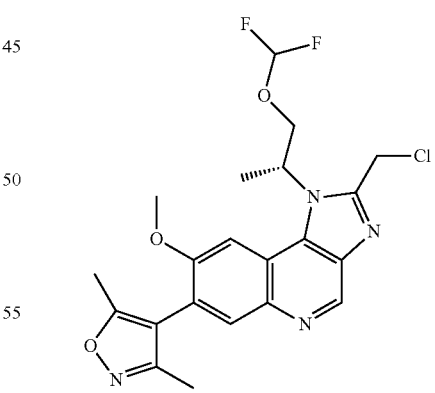

To a stirred solution of N4-[(1R)-2-(difluoromethoxy)-1-methyl-ethyl]-7-(3,5-dimethylisoxazol-4-yl)-6-methoxy-quinoline-3,4-diamine (1.4 g, 3.58 mmol) in 2-chloro-1,1,1-trimethoxy-ethane (10 mL, 74.2 mmol) was added para-toluenesulfonic acid hydrate (68 mg, 0.356 mmol). The resulting mixture was stirred at 80OC for 3 h. The mixture was purified by column chromatography on silica gel eluting with 0-100% ethyl acetate in hexanes. The product containing fractions were concentrated in vacuo and stirred in diethyl ether to give a white solid, collected via vacuum filtration (1.21 g, 75%). $^1$H NMR (d6-DMSO, 300 MHz) δ 9.10 (s, 1H), 8.05 (s, 1H), 7.54 (s, 1H), 6.67 (t, J=75 Hz, 1H), 5.86-5.38 (m, 1H), 5.27-5.17 (m, 2H), 4.68-4.38 (m, 2H), 4.00 (s, 3H), 2.33 (s, 3H), 2.14 (s, 3H), 1.95-1.76 (m, 3H).

Example 5: Alternate method to 4-[1-[(1S)-2-(difluoromethoxy)-1-methyl-ethyl]-8-methoxy-2-tetrahydropyran-4-yl-imidazo[4,5-c]quinolin-7-yl]-3,5-dimethyl-isoxazole (a) (N-[4-[[(1 S)-2-(difluoromethoxy)-1-methyl-ethyl]amino]-7-(3,5-dimethylisoxazol-4-yl)-6-methoxy-3-quinolyl]tetrahydropyran-4-carboxamide

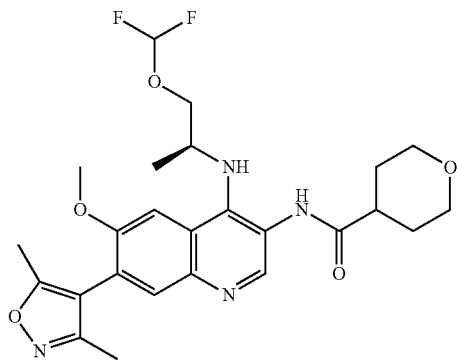 [SMILES: COc1cc2c(N[C@@H](C)COC(F)F)c(NC(=O)C3CCOCC3)cnc2cc1-c1c(C)noc1C]

To a stirred solution of N4-[(1 S)-2-(difluoromethoxy)-1-methyl-ethyl]-7-(3,5-dimethylisoxazol-4-yl)-6-methoxy-quinoline-3,4-diamine (304 mg, 0.775 mmol) in DMF (5 mL) was added tetrahydropyran-4-carboxylic acid (151 mg, 1.16 mmol) and hydroxybenzotriazole (11.8 mg, 0.077 mmol). The resulting mixture was treated with HBTU (440 mg, 1.16 mmol) followed by DIPEA (404 µL, 2.32 mmol) and stirred overnight. The mixture was diluted with ethyl acetate and washed with saturated NaHCO$_3$(3×). The organic phase was dried, filtered and concentrated in vacuo then chromatographed in 40-100% ethyl acetate in hexanes followed by 0-2% MeOH in ethyl acetate giving the desired product as a sticky oil (257 mg, 66%). $^1$H NMR (d6-DMSO) δ 9.54 (s, 1H), 8.29 (s, 1H), 7.70 (s, 1H), 7.60 (s, 1H), 6.68 (t, J=76 Hz, 1H), 5.42 (d, J=9 Hz, 1H), 4.09-3.72 (m, 5H), 3.91 (s, 3H), 3.45-3.32 (m, 2H), 2.75-2.59 (m, 1H), 2.30 (s, 3H), 2.10 (s, 3H), 1.83-1.54 (m, 4H), 1.23-1.16 (m, 3H).

(b) 4-[1-[(1 S)-2-(difluoromethoxy)-1-methyl-ethyl]-8-methoxy-2-tetrahydropyran-4-yl-imidazo[4,5-c]quinolin-7-yl]-3,5-dimethyl-isoxazole

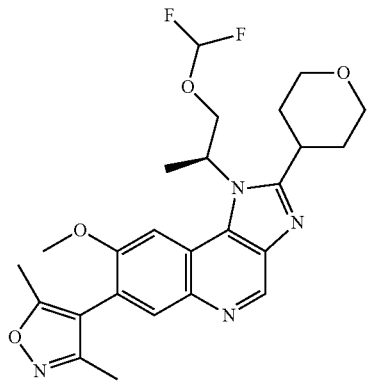 [SMILES: COc1cc2c(cc1-c1c(C)noc1C)ncc1nc(C3CCOCC3)n([C@@H](C)COC(F)F)c12]

A stirred solution N-[4-[[(1S)-2-(difluoromethoxy)-1-methyl-ethyl]amino]-7-(3,5-dimethylisoxazol-4-yl)-6-methoxy-3-quinolyl]tetrahydropyran-4-carboxamide (190 mg, 0.38 mmol) in acetic acid (4 mL) was stirred at 90-1000C overnight. The mixture was diluted with ethyl acetate and washed with saturated NaHCO$_3$(3×) and brine (1×). The organic phase was dried, filtered and concentrated in vacuo then chromatographed in 0-2% methanol in ethyl acetate. The product containing fractions were concentrated in vacuo giving the product (46 mg, 25%).

Biological Testing

Example 6: Binding of the Compounds of the Application to Bromodomains BRD2, BRD3 and BRD4

The binding of the compounds of the application to bromodomains BRD2, BRD3 and BRD4 was assessed using a time resolved fluorescent resonance energy transfer binding assay (Alpha Screen Technology), that measures the binding of an acetylated histone peptide to the bromodomain protein. The bromodomain protein, histone peptide and a variable concentration of test compound were incubated together to reach thermodynamic equilibrium. The assay was configured such that in the absence of test compound the bromodomain and peptide were significantly bound (~30%) and in the presence of a sufficient concentration of a potent inhibitor this interaction was disrupted leading to a measurable drop in fluorescent resonance energy transfer. The IC$_{50}$ values of the representative compounds of the application for binding at BRD2, BRD3 and BRD4 are provided in Table 3.

Example 7: National Cancer Institute (NCI) Screening Panel

Representative compounds of the application were screened using the National Cancer Institute (NCI) screening panel, which consists of a panel of 60 different human tumor cell lines, representing leukemia [CCRF-CEM, HL-60 (TB), K-562, MOLT-4, SR], melanoma [LOX IMVI, MALME-3M, M14, SMDA-MB-435, SK-MEL-2, SK-MEL-28, SK-MEL-5, UACC-257 and UACC-62] and cancers of the lung [A549/ATCC, EKVX, HOP-62, HOP-93, NCI-H226, NCI-H23, NCI-H322M, NCI-H460], colon [COLO 205, HCT-116, HCT-15, HT29, KM12, SW-620], brain [SF-268, SF-295, SF-539, SNB-19, SNB-75, U251], ovary [IGROV1, OVCAR-3, OVCAR-4, OVCAR-5, OVCAR-8, NCI/ADR-RES, SK-OV-3], breast [MCF7, MDA-MB-231, BT-549, T-47D, MDA-MB-468], prostate [PC-3, DU-145], and renal [786-0, A498, ACHN, CAKI-1, RXF-393, SN12C, TK-10, UO-31]cancers.

After 24 h, two plates of each cell line were fixed in situ with TCA, to represent a measurement of the cell population for each cell line at the time of drug addition (T$_z$). Experimental drugs were solubilised in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 µg/ml gentamicin. Additional four, 10-fold or ½ log serial dilutions were made to provide a total of five drug concentrations plus control. Aliquots of 100 µl of these different drug dilutions were added to the appropriate microtiter wells already containing 100 µl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA (trichloroacetic acid). Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilised with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA). Using the seven absorbance measurements [time zero, ($T_z$), control growth, (C), and test growth in the presence of drug at the five concentration levels ($T_i$)], the percentage growth was calculated at each of the drug concentration levels. Percentage growth inhibition was calculated as: $[(T_i-T_z)/(C-T_z)]\times100$ for concentrations in which $T_i >/= T_z$ and $[(T_i-T_z)/T_z]\times100$ for concentrations in which $T_i < T_z$.

Three dose response parameters were calculated for each experimental agent. Growth inhibition of 50% ($GI_{50}$) was calculated from $[(T_i-T_z)/(C-T_z)]\times100=50$, which is the drug concentration resulting in a 50% reduction in the net protein increase (as measured by SRB staining) in control cells during the drug incubation. The drug concentration resulting in total growth inhibition (TGI) was calculated from $T_i=T_z$. The $LC_{50}$ (concentration of drug resulting in a 50% reduction in the measured protein at the end of the drug treatment as compared to that at the beginning) indicating a net loss of cells following treatment was calculated from $[(T_i-T_z)/T_z]\times100=-50$. Values were calculated for each of these three parameters if the level of activity was reached. However, if the effect was not reached or was exceeded, the value for that parameter was expressed as greater or less than the maximum or minimum concentration tested.

The results obtained from this study shows compounds of the application are effective against the cell lines of the 60 human tumor cell lines panel. Inhibition of human cancer cell lines in vitro by representative compounds of Formula (I) are shown in Table 4.

Example 8: Oncology Cell Growth Assay

Human cell lines were cultured in RPMI-1640 containing 10% fetal bovine serum, 1000 viable cells per well were plated in 384-well black flat bottom polystyrene plates (Greiner #781086) in 48-1 of culture media. All plates were placed at 5% $CO_2$, 37° C. overnight. The following day one plate was harvested with CeliTiter-Glo (CTG, Promega #G7573) for a time equal to 0 (T0) measurement and compound (20 point titration from 14.7 uM to 7 pM) was added to the remaining plates. The final concentration of DMSO in all wells was 0.15%. Cells were incubated for 72 hours or the indicated time and each plate was developed with CeliTiterGlo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results are expressed as a percent of the TO and plotted against the compound concentration. The TO value was normalized to 100% and represents the number of cells at time of compound addition and the concentration response data were fit with a 4 parameter curve fit using XLfit software (model 205). The concentration that inhibited cell growth by 50% (gIC50) is the midpoint of the 'growth window' (between the TO and DMSO control). The Ymin –TO value was determined by subtracting the TO value (100%) from the Ymin value (%) determined from the fit of the concentration response curve. Values from the wells with no cells were subtracted from all samples for background correction. Representative compounds were tested in accordance with the above procedure and found to have the gIC50 as shown in Table 5.

Example 9: BET Bromodomain: AlphaScreen Assay

Protocol

Assay Format:

The reader assay was a binding assay using the AlphaScreen technology fluorescence energy resonance transfer (FRET) assay. The biotinylated peptide binding to the reader domain of His-tagged protein is monitored by the singlet oxygen transfer from the Streptavidin-coated donor beads to the AlphaScreen Ni-chelate acceptor beads.

Reagent:

Reaction buffer: 50 mM Hepes, pH7.5, 100 mM NaCl, 0.05% CHAPS, 0.1% BSA, and 1% DMSO (Buffer and DMSO concentration may be different for different reader).

Ligand:

Biotin-peptide; sequences were different for different targets.

Reaction Procedure:

1. Deliver 4×BRD in wells of reaction plate except No BRD control wells. Add buffer instead.
2. Deliver compounds in 100% DMSO into the BRD mixture by Acoustic technology (Echo550; nanoliter range). Spin down and pre-incubation for 30 min.
3. Deliver 4× Ligand. Spin and shake.
4. Incubate for 30 min at room temperature with gentle shaking.
5. Deliver 4× donor beads. Spin and shake.
6. Deliver 4× acceptor beads. Spin and shake. Then gentle shaking in the dark for 60 min.
7. Alpha measurement (Ex/Em=680/520–620 nm) in Enspire.

Results:

Table 6 presents the bromodomain $EC_{50}$ values for a representative group of compounds of the application.

Example 10: Liver Microsome Stability Studies (Human & Mouse)

Protocol

For Phase I analysis, test compounds (10 mM stock in DMSO) were incubated at a final concentration of 1 μM (this concentration was assumed to be well below the Km values to ensure linear reaction conditions). Working stocks were initially diluted to a concentration of 40.0 μM in 0.1 M potassium phosphate buffer before addition to the reaction vials. Pooled mouse (CD-1, male) or human (50 donors) liver microsomes were utilized at a final concentration of 0.5 mg/ml. Duplicate wells were used for each time point (0 and 30 minutes). Reactions were carried out at 37° C. in a shaker, and the final concentration of DMSO was kept constant at 0.01%. The final volume for each reaction was 100 μL, which includes the addition of an NADPH-Regeneration solution (NRS) mix. This NRS mix was comprised of glucose 6-phosphate dehydrogenase (0.4 U/mL), NADP+ (1.3 mM), $MgCl_2$ (3.3 mM), and glucose 6-phosphate (3.3 mM) in assay mixtures. Upon completion of the 30 minute time point, reactions were terminated by the addition of 1.5-volumes (150 μL) of ice-cold, acetonitrile with 0.5% formic acid and internal standard. Samples were then centrifuged at 4,000 rpm for 10 minutes to remove debris and precipitated protein. Approximately 150 μL of supernatant was subsequently transferred to a new 96 well microplate for LC/MS analysis.

Narrow-window mass extraction LC/MS analysis was performed for all samples using a Waters Xevo quadrupole time-of-flight (QTof) mass spectrometer and an ACQUITY UPLC system, to determine relative peak areas of parent compound.

$$\% \text{ remaining} = \frac{\text{Area count of } t = 30 \text{ min}}{\text{Area count of } t = 0 \text{ min}} \times 100$$

The % recovery of compounds of the application from human and mouse liver microsomes is provided in Table 7.

Example 11: MV4-11 Subcutaneous Human AML Xenograft Model

Protocol
1. Study Design
Animals
  Species & Strain: NOD SCID mice
  Age: 7-8 week
  Total Number: 60 mice plus 40% spare
  Sex: Female
  Body Weight: 18 to 22 g
Animal Maintenance
  Quarantine: Animals were quarantined for 7 days before the study. The general health of the animals was evaluated by a veterinarian, and complete health checks were performed. Animals with abnormalities were excluded prior the study.
  Housing: General procedures for animal care and housing were in accordance with the standard, Commission on Life Sciences, National Research Council, Standard operating procedures (SOPs) of Pharmaron, Inc. The mice were kept in laminar flow rooms at constant temperature and humidity with 3-5 mice in each cage. Animals were housed in a polycarbonate cage which is in the size of 300×180×150 $mm^3$ and in an environmentally monitored, well-ventilated room maintained at a temperature of (22±3° C.) and a relative humidity of 40%-80%. Fluorescent lighting provided illumination approximately 12 hours per day. The bedding material was soft wood, which was changed once per week.
  Animal ID: Each animal was assigned an identification number; the following identification method was applied. Each cage card was labeled with such information as study number, group, sex, dose, animal number, initiation date, study director and telephone number. Individual animal was identified by ear coding.
  Diet: Animals had free access to irradiation sterilized dry granule food during the entire study period except for time periods specified by the protocol.
  Water: Sterile drinking water in a bottle was available to all animals ad libitum during the quarantine and study periods. The bottle and the stopper with attached sipper tube were autoclaved prior to use. Samples of water from the animal facility were analyzed and results of water analysis were retained in the facility records and were reviewed by the veterinarian, or designee, to assure that no known contaminants were present that could interfere with or affect the outcome of studies.
Groups and Treatments
  Groups and treatments started when the mean tumor volume reached 138 $mm^3$. Based on the tumor volume, mice were randomly assigned to respective groups using a computer-generated randomization procedure.
2. Experimental Method and Measurement Parameters
Method for Tumor Inoculation
  Each mouse was inoculated subcutaneously on the right flank with MV4-11 tumor cells (1×107) in 0.1 ml of IMDM without serum for tumor development. The treatment started when the mean tumor size reached approximately 138 $mm^3$. Mice were randomized into groups. The treatments were administrated to the tumor-bearing mice accordingly to the study design shown in Table 8.
Measurement Parameters
  For routine monitoring, all study animals were monitored not only tumor growth but also behavior such as mobility, food and water consumption (by cage side checking only), body weight (BW), eye/hair matting and any other abnormal effect. Any mortality and/or abnormal clinical signs would be recorded.
Body Weight
  Body weights of all animals were measured twice weekly throughout the study.
Tumor Measurements and the Endpoints
  During the course of study, the tumor size was measured twice a week in two dimensions using a caliper, and the volume was expressed in $mm^3$ using the formula: TV=a× b2/2 where a and b were the long and short diameters of the tumor, respectively. The tumor size was then used for T/C and TGI (tumor growth inhibition) values, which were indicators of anti-tumor effectiveness. T/C was calculated with the formula [(Td −T0)/(Cd −C0)]×100%, TGI is calculated with the formula [1−(Td −T0)/(Cd −C0)]×100%. Td and Cd were the mean tumor volumes (or median tumor volumes) of the treated and control animals, and T0 and C0 were the mean tumor volumes of the treated and control animals at the start of the experiment.
Data Acquisition and Statistical Analysis
  Data Acquisition: Protocol-required measurements and observations were recorded manually on appropriate forms, or directly on a computerized database.
  Statistical Analysis: All statistical tests were conducted, and the level of significance was set at 5% or $P<0.05$. The group means, standard deviation were calculated for all measurement parameters as study designed. One-way analysis of variance (ANOVA) testing was applied among the groups.
Results and Discussion
  In this study, the therapeutic efficacy and tolerance of compounds of the application including 2(g).HCl and 2(l).HCl were evaluated in the MV4-11 human AML xenograft model. Overall, the test compound 2(g).HCl at a dose levels of 30 mg/kg and 50 mg/kg had significant antitumor activity in a dose dependent manner. The low-dose of 2(g).HCl (10 mg/kg) also showed moderate antitumor activity. Noteworthy, the test compound 2(l).HCl at both 30 mg/kg and 50 mg/kg also showed significant antitumor activity in the MV4-11 human AML xenograft model. Regarding the safety profile, the test compound 2(g).HCl at the dose level of 50 mg/kg caused 9.1% body weight loss during the dosing period and after a two days dose suspension on Day 8 and 9, with sponsor approval, body weight of the treated animals in this group were maintained or recovered. Nonetheless, the rest of the treatment groups at low and mid dose were tolerated well by the animals. The test compound 2(l).HCl was tolerated well by the treated animals at all dose levels. No gross clinical abnormalities were observed in all treatment groups over the course of study period.

Example 12: MM.1S Mouse Subcutaneous Human Multiple Myeloma Xenograft Model

Protocol
1. Study Design
Animals
  Species & Strain: NOD SCID mice
  Age: 7-8 week
  Total Number: 50 mice plus 40% spare
  Sex: Female
  Body Weight: 18 to 22 g
Animal Maintenance
  Quarantine: Animals were quarantined for 7 days before the study. The general health of the animals were evaluated by a veterinarian, and complete health checks were performed. Animals with abnormalities were excluded prior the study.
  Housing: General procedures for animal care and housing are in accordance with the standard, Commission on Life Sciences, National Research Council, Standard operating procedures (SOPs) of Pharmaron, Inc. The mice were kept in laminar flow rooms at constant temperature and humidity with 3-5 mice in each cage. Animals were housed in polycarbonate cage which is in the size of 300×180×150 mm$^3$ and in an environmentally monitored, well-ventilated room maintained at a temperature of (22±3° C.) and a relative humidity of 40%-80%. Fluorescent lighting provided illumination approximately 12 hours per day. The bedding material was soft wood, which was changed once per week.
  Animal ID: Each animal was assigned an identification number; the following identification method was applied. Each cage card was labeled with such information as study number, group, sex, dose, animal number, initiation date, study director and telephone number. Individual animal was identified by ear coding.
  Diet: Animals had free access to irradiation sterilized dry granule food during the entire study period except for time periods specified by the protocol.
  Water: Sterile drinking water in a bottle was available to all animals ad libitum during the quarantine and study periods. The bottle and the stopper with attached sipper tube was autoclaved prior to use. Samples of water from the animal facility were analyzed and results of water analysis were retained in the facility records and were reviewed by the veterinarian, or designee, to assure that no known contaminants were present that could interfere with or affect the outcome of studies.
Groups and Treatments
  Groups and treatments started when the mean tumor volume reached about 100-150 mm$^3$. Based on the tumor volume, mice were randomly assigned to respective groups using a computer-generated randomization procedure. The study groups and number of animals per group are shown in Table 9.

Formulation and Dosing Procedure
  The preparation of the vehicle, compound 2(g) and carfilzomib (CFZ) formulations are shown in Table 10. Further, Table 11 illustrates the dosing route, frequency and duration of the treatment.
2. Experimental Method and Measurement Parameters
2.1 Method for Tumor Inoculation
  Each mouse was inoculated subcutaneously on the right flank with MM. 1S tumor cells (5×10$^6$) in 0.1 ml of RPMI-1640 without serum (mixed matrigel) for tumor development. The treatment started when the mean tumor size reached approximately 100-150 mm$^3$. Mice were then randomized into groups. The treatments were administrated to the tumor-bearing mice accordingly to the study design showed in Table 9.
2.2 Measurement Parameters
  For routine monitoring, all study animals monitored not only tumor growth but also behavior such as mobility, food and water consumption (by cage side checking only), body weight (BW), eye/hair matting and any other abnormal effect. Any mortality and/or abnormal clinical signs were recorded.
Body Weight
  Body weights of all animals were measured twice weekly throughout the study. Body weight change, expressed in %, was calculated using the following formula:

$$BW \text{ change } (\%) = ((BWDay\ X - BWDay\ 0)/BWDay\ 0) \times 100$$

The measurement of tumor size was conducted twice weekly with a caliper and the tumor volume (mm$^3$) was estimated using the formula: TV=a×b$^2$/2, where "a" and "b" are long and short diameters of a tumor, respectively. The TVs were used for calculation of the tumor growth inhibition (TGI, an indicator of antitumor effectiveness) value using the formula: TGI=(1−T/C)×100%, where "T" and "C" is the mean relative volumes (% tumor growth) of the tumors in the treated and the control groups, respectively, on a given day after tumor inoculation. The experiment terminated when the mean tumor volume exceeded 2000 mm$^3$ or severe body weight loss was observed.
2.3 Data Acquisition and Statistical Analysis:
  Data Acquisition: Protocol-required measurements and observations were recorded manually on appropriate forms, or directly on a computerized database.
  Statistical Analysis: All statistical tests were conducted, and the level of significance was set at 5% or P<0.05. The group means, standard deviation were calculated for all measurement parameters as study designed. One-way analysis of variance (ANOVA) following LSD multiple comparisons testing was applied among the groups.
Results and Discussion
  In this study, the therapeutic efficacy and tolerance of compound 2(g) was evaluated in a MM.1S subcutaneous human multiple myeloma xenograft model. Overall, the test compound 2(g) at the dose levels of 10 mg/kg, 30 mg/kg and 60 mg/kg significantly reduced the tumor volume (mm$^3$) with a dose dependent manner, 21 days post administration. In particular, the dose levels of 30 mg/kg and 60 mg/kg reduced the tumor volume to a greater extent than carfilzomib (CFZ), 21 days post administration. Nevertheless, the low-dose of compound 2(g) (10 mg/kg) still produced a moderate antitumor activity, FIG. 1.
  While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Summary the ¹H NMR and LCMS characteristics of representative compounds prepared using Method A

| Example # | Structure | NMR | MW [M] | Observed LCMS [M + 1] |
|---|---|---|---|---|
| 2(g) | 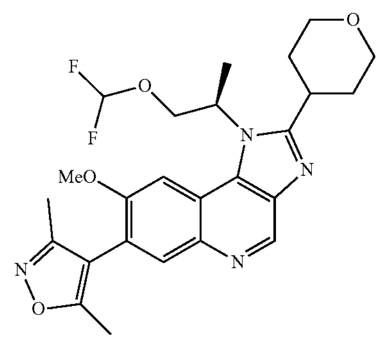 [SMILES: COc1cc2c(cc1-c1c(C)noc1C)ncc1nc(C3CCOCC3)n([C@H](C)COC(F)F)c12] | ¹H NMR (d6-DMSO 400 MHz) δ 9.07 (s, 1H), 8.01 (s, 1H), 7.47 (s, 1H), 6.60 (t, J = 767 Hz, 1H), 5.86-5.83 (m, 1H), 5.47-5.33 (m, 1H), 4.74 (m, 1H), 4.56-4.41 (m, 2H), 3.98 (s, 3H), 3.98-3.91 (m, 1H), 3.63-3.50 (m, 2H), 3.50-3.38 (m, 1H), 2.33 (s, 3H), 2.14 (s, 3H), 2.02-1.73 (m, 6H). | 486.51 | 487.16 |
| 2(j) | 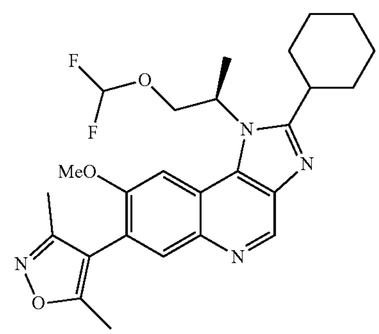 [SMILES: COc1cc2c(cc1-c1c(C)noc1C)ncc1nc(C3CCCCC3)n([C@H](C)COC(F)F)c12] | ¹H NMR (d6-DMSO 400 MHz) δ 9.04 (s, 1H), 8.00 (s, 1H), 7.46 (s, 1H), 6.62 (t, J = 76 Hz, 1H), 5.86-5.81 (m, 1H), 5.41-5.27 (m, 1H), 4.73-4.61 (m, 1H), 4.56-4.39 (m, 2H), 3.98 (s, 3H), 3.20-3.05 (m, 1H), 2.33 (s, 3H), 2.14 (s, 3H), 1.94-1.66 (m, 6H), 1.57-1.39 (m, 3H), 1.39-1.30 (m, 2H). | 484.54 | 485.40 |
| 2(h) | 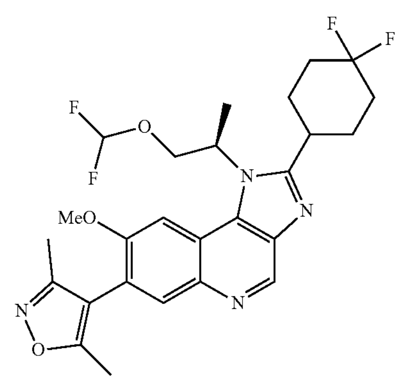 [SMILES: COc1cc2c(cc1-c1c(C)noc1C)ncc1nc(C3CCC(F)(F)CC3)n([C@H](C)COC(F)F)c12] | ¹H NMR (d6-DMSO 400 MHz) δ 9.06 (s, 1H), 8.01 (s, 1H), 7.48 (s, 1H), 6.61 (t, J = 76 Hz, 1H), 5.88-5.71 (m, 1H), 5.48-5.34 (m, 1H), 4.76-4.62 (m, 1H), 4.62-4.39 (m, 2H), 3.98 (s, 3H), 3.46-3.34 (m, 1H), 2.33 (s, 3H), 2.21-1.93 (m, 6H), 2.14 (s, 3H), 1.90-1.76 (m, 3H). | 520.52 | 521.39 |
| 2(l) | 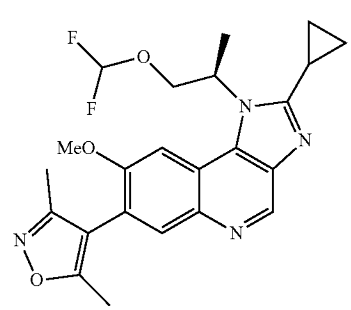 [SMILES: COc1cc2c(cc1-c1c(C)noc1C)ncc1nc(C3CC3)n([C@H](C)COC(F)F)c12] | ¹H NMR (d6-DMSO 400 MHz) δ 9.46 (s, 1H), 8.19 (s, 1H), 7.94 (s, 1H), 6.67 (t, J = 76 Hz, 1H), 5.99-5.81 (m, 1H), 4.81-4.69 (m, 1H), 4.57-4.43 (m, 1H), 4.07 (s, 3H), 3.74-3.49 (m, 1H), 2.36 (s, 3H), 2.16 (s, 3H), 1.86 (d, J = 8 Hz, 3H), 1.33-1.17 (m, 4H). | 442.45 | 443.27 |

TABLE 1-continued

Summary the ¹H NMR and LCMS characteristics of representative compounds prepared using Method A

| Example # | Structure | NMR | MW [M] | Observed LCMS [M + 1] |
|---|---|---|---|---|
| 2(k) | 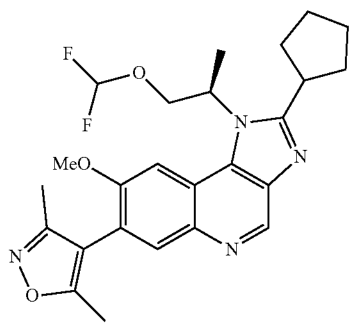 | ¹H NMR (d6-DMSO 400 MHz) δ 9.04 (s, 1H), 8.00 (s, 1H), 7.46 (s, 1H), 6.62 (t, J = 76 Hz, 1H), 5.87-5.83 (m, 1H), 5.45-5.30 (m, 1H), 4.75-4.61 (m, 1H), 4.61-4.31 (m, 2H), 3.97 (s, 3H), 3.64-3.49 (m, 1H), 2.33 (s, 3H), 2.14 (s, 3H), 2.08-1.62 (m, 9H). | 470.51 | 471.30 |
| 2(m) | 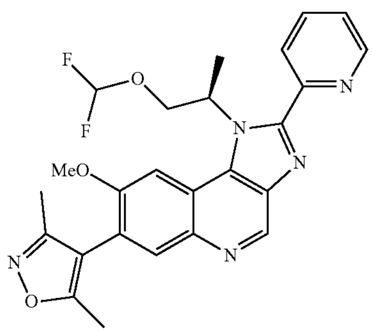 [SMILES: COc1cc2c(cc1-c1c(C)noc1C)ncc1nc(-c3ccccn3)n([C@H](C)COC(F)F)c12] | ¹H NMR (d6-DMSO 400 MHz) δ 9.16 (s, 1H), 8.79 (s, 1H), 8.23-8.13 (m, 1H), 8.10-7.80 (m, 3H), 7.65-7.55 (m, 1H), 6.60 (t, J = 76 Hz, 1H), 5.96-5.80 (m, 1H), 4.94-4.80 (m, 1H), 4.50-4.39 (m, 1H), 4.02 (s, 3H), 2.34 (s, 3H), 2.15 (s, 3H), 1.77-1.53 (m, 3H). | 479.48 | 480.14 |
| 2(i) | 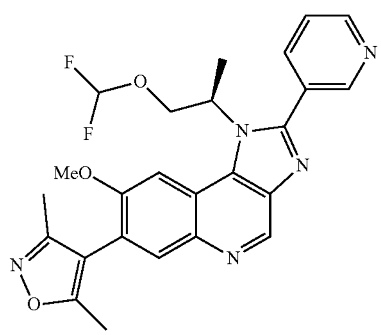 [SMILES: COc1cc2c(cc1-c1c(C)noc1C)ncc1nc(-c3cccnc3)n([C@H](C)COC(F)F)c12] | ¹H NMR (d6-DMSO 400 MHz) δ 9.06 (s, 1H), 8.01 (s, 1H), 7.48 (s, 1H), 6.61 (t, J = 76 Hz, 1H), 5.88-5.71 (m, 1H), 5.48-5.34 (m, 1H), 4.76-4.62 (m, 1H), 4.62-4.39 (m, 2H), 3.98 (s, 3H), 3.46-3.34 (m, 1H), 2.33 (s, 3H), 2.21-1.93 (m, 6H), 2.14 (s, 3H), 1.90-1.76 (m, 3H). | 479.48 | 480.14 |
| 2(f) | 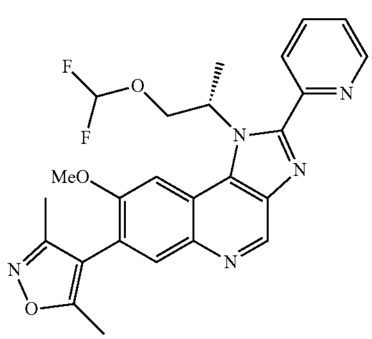 [SMILES: COc1cc2c(cc1-c1c(C)noc1C)ncc1nc(-c3ccccn3)n([C@@H](C)COC(F)F)c12] | ¹H NMR (d6-DMSO 400 MHz) δ 9.16 (s, 1H), 8.79 (s, 1H), 8.23-8.13 (m, 1H), 8.10-7.80 (m, 3H), 7.65-7.55 (m, 1H), 6.60 (t, J = 76 Hz, 1H), 5.96-5.80 (m, 1H), 4.94-4.80 (m, 1H), 4.50-4.39 (m, 1H), 4.02 (s, 3H), 2.34 (s, 3H), 2.15 (s, 3H), 1.77-1.53 (m, 3H). | 479.48 | 480.14 |

TABLE 1-continued

Summary the ¹H NMR and LCMS characteristics of representative compounds prepared using Method A

| Example # | Structure | NMR | MW [M] | Observed LCMS [M + 1] |
|---|---|---|---|---|
| 2(e) | 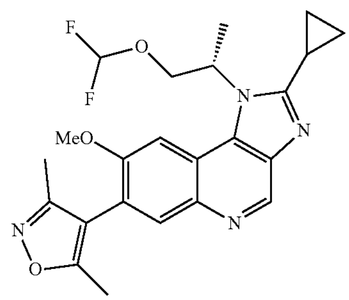 [SMILES: COc1cc2c(cc1-c1c(C)noc1C)ncc1nc(C3CC3)n([C@@H](C)COC(F)F)c12] | ¹H NMR (d6-DMSO 400 MHz) δ 9.46 (s, 1H), 8.19 (s, 1H), 7.94 (s, 1H), 6.67 (t, J = 76 Hz, 1H), 5.99-5.81 (m, 1H), 4.81-4.69 (m, 1H), 4.57-4.43 (m, 1H), 4.07 (s, 3H), 3.74-3.49 (m, 1H), 2.36 (s, 3H), 2.16 (s, 3H), 1.86 (d, J = 8 Hz, 3H), 1.33-1.17 (m, 4H). | 442.45 | 443.27 |
| 2(d) | 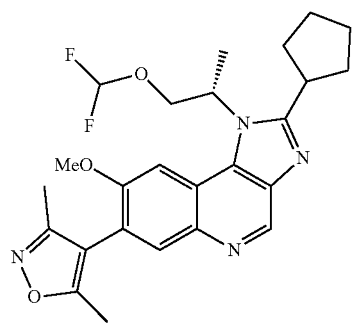 [SMILES: COc1cc2c(cc1-c1c(C)noc1C)ncc1nc(C3CCCC3)n([C@@H](C)COC(F)F)c12] | ¹H NMR (d6-DMSO 400 MHz) δ 9.04 (s, 1H), 8.00 (s, 1H), 7.46 (s, 1H), 6.62 (t, J = 76 Hz, 1H), 5.87-5.83 (m, 1H), 5.45-5.30 (m, 1H), 4.75-4.61 (m, 1H), 4.61-4.31 (m, 2H), 3.97 (s, 3H), 3.64-3.49 (m, 1H), 2.33 (s, 3H), 2.14 (s, 3H), 2.08-1.62 (m, 9H). | 470.51 | 471.30 |
| 2(c) | 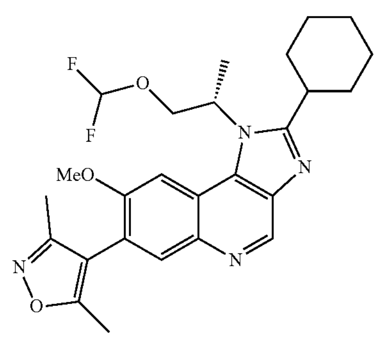 [SMILES: COc1cc2c(cc1-c1c(C)noc1C)ncc1nc(C3CCCCC3)n([C@@H](C)COC(F)F)c12] | ¹H NMR (d6-DMSO 400 MHz) δ 9.04 (s, 1H), 8.00 (s, 1H), 7.46 (s, 1H), 6.62 (t, J = 76 Hz, 1H), 5.86-5.81 (m, 1H), 5.41-5.27 (m, 1H), 4.73-4.61 (m, 1H), 4.56-4.39 (m, 2H), 3.98 (s, 3H), 3.20-3.05 (m, 1H), 2.33 (s, 3H), 2.14 (s, 3H), 1.94-1.66 (m, 6H), 1.57-1.39 (m, 3H), 1.39-1.30 (m, 2H). | 484.54 | 485.40 |
| 2(a) | 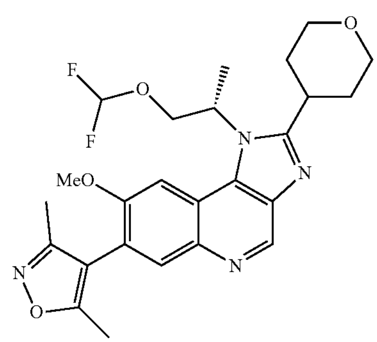 [SMILES: COc1cc2c(cc1-c1c(C)noc1C)ncc1nc(C3CCOCC3)n([C@@H](C)COC(F)F)c12] | ¹H NMR (d6-DMSO 400 MHz) δ 9.07 (s, 1H), 8.01 (s, 1H), 7.47 (s, 1H), 6.60 (t, J = 767 Hz, 1H), 5.86-5.83 (m, 1H), 5.47-5.33 (m, 1H), 4.74 (m, 1H), 4.56-4.41 (m, 2H), 3.98 (s, 3H), 3.98-3.91 (m, 1H), 3.63-3.50 (m, 2H), 3.50-3.38 (m, 1H), 2.33 (s, 3H), 2.14 (s, 3H), 2.02-1.73 (m, 6H). | 486.51 | 487.16 |

TABLE 1-continued
Summary the ¹H NMR and LCMS characteristics of representative compounds prepared using Method A
| Example # | Structure | NMR | MW [M] | Observed LCMS [M + 1] |
|---|---|---|---|---|
| 2(n) | 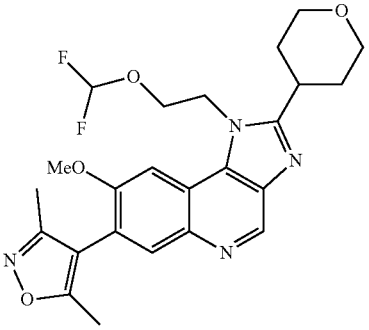 [SMILES: COc1cc2c(cc1-c1c(C)noc1C)ncc1nc(C3CCOCC3)n(CCOC(F)F)c12] | ¹H NMR (d6-DMSO 400 MHz) δ 9.04 (s, 1H), 7.97 (s, 1H), 7.65 (s, 1H), 6.64 (t, J = 76 Hz, 1H), 5.07 (t, J = 4 Hz, 2H), 4.38 (t, J = 4 Hz, 2H), 4.01-3.95 (m, 2H), 3.98 (s, 3H), 3.58-3.49 (m, 2H), 3.48-3.40 (m, 1H), 2.32 (s, 3H), 2.12 (s, 3H), 2.00-1.88 (m, 2H), 1.88-1.80 (m, 2H). | 472.48 | 473.36 |
| 2(o) | 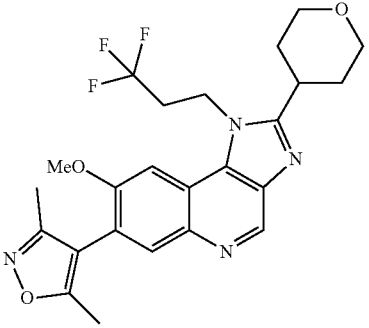 [SMILES: COc1cc2c(cc1-c1c(C)noc1C)ncc1nc(C3CCOCC3)n(CCC(F)(F)F)c12] | ¹H NMR (d6-DMSO 400 MHz) δ 9.05 (s, 1H), 7.99 (s, 1H), 7.63 (s, 1H), 5.02 (t, J = 8 Hz, 2H), 4.02-3.95 (m, 2H), 3.99 (s, 3H), 3.61-3.51 (m, 2H), 3.47-3.36 (m, 1H), 3.13-3.01 (m, 2H), 2.32 (s, 3H), 2.13 (s, 3H), 1.99-1.82 (m, 4H). | 474.48 | 475.37 |
| 2(p) | 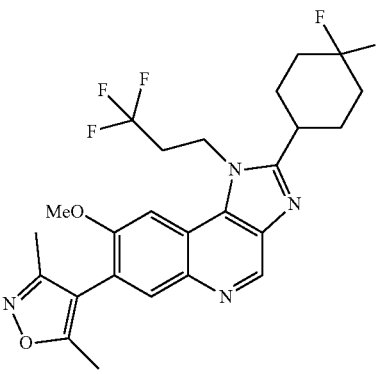 | ¹H NMR (d6-DMSO 400 MHz) δ 9.04 (s, 3H), 7.99 (s, 3H), 7.64 (s, 3H), 5.02 (t, J = 8 Hz, 2H), 3.99 (s, 3H), 3.41-3.42 (m, 1H), 3.13-3.01 (m, 2H), 2.32 (s, 3H)2.24-2.13 (m, 4H), 2.13 (s, 3H), 2.09-1.91 (m, 4H). | 508.48 | 509.41 |

TABLE 2

Summary the ¹H NMR and LCMS characteristics of representative compounds prepared from intermediate I (Scheme II) with various amines

| Example # | Structure | NMR | MW [M] | Observed LCMS [M + 1] |
|---|---|---|---|---|
| 3(a) | 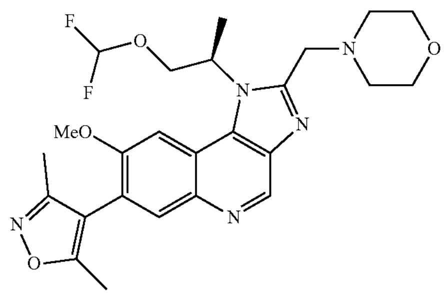 [SMILES: COc1cc2c(cc1-c1c(C)noc1C)ncc1nc(CN3CCOCC3)n([C@H](C)COC(F)F)c12] | ¹H NMR (CD₃OD 400 MHz) δ 9.64 (s, 1H), 8.22 (s, 1H), 8.10 (s, 1H), 6.45 (t, J = 74 Hz, 1H), 6.19-6.05 (m, 1H), 5.44-4.93 (m, 4H), 4.93-4.78 (m, 1H), 4.81-4.51 (m, 3H), 4.16 (s, 3H), 4.19-3.99 (m, 4H), 3.94-3.50 (brs, 3H), 2.42 (s, 3H), 2.24 (s, 3H), 2.06-1.90 (m, 3H). | 501.52 | 502.45 |
| 3(d) | 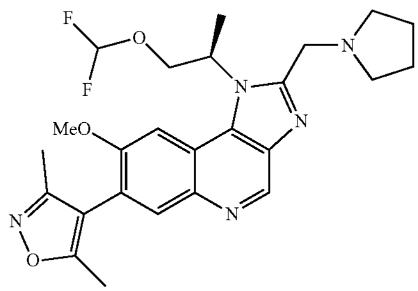 [SMILES: COc1cc2c(cc1-c1c(C)noc1C)ncc1nc(CN3CCCC3)n([C@H](C)COC(F)F)c12] | ¹H NMR (d6-DMSO 300 MHz) δ 9.61 (s, 1H), 8.50 (s, 1H), 7.98 (s, 1H), 6.72 (t, J = 74 Hz, 1H), 6.05-5.87 (m, 1H), 5.26-5.13 (m, 2H), 4.71-4.39 (m, 2H), 4.38-4.00 (brs, 2H), 4.07 (s, 3H), 3.99-3.73 (m, 2H), 3.49-3.17 (m, 2H), 2.37 (s, 3H), 2.17 (s, 3H), 2.17-1.86 (m, 4H), 1.84-1.71 (m, 3H). | 485.53 | 486.40 |
| 3(f) | 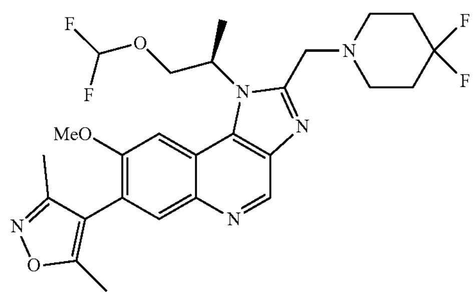 [SMILES: COc1cc2c(cc1-c1c(C)noc1C)ncc1nc(CN3CCC(F)(F)CC3)n([C@H](C)COC(F)F)c12] | ¹H NMR (d6-DMSO 400 MHz) δ 9.06 (s, 1H), 8.02 (s, 1H), 7.54 (s, 1H), 6.69 (t, J = 76 Hz, 1H), 5.65-5.51 (m, 1H), 4.67-4.42 (m, 2H), 4.14-3.78 (m, 2H), 3.99 (s, 3H), 2.66-2.50 (m, 4H), 2.33 (s, 3H), 2.13 (s, 3H), 2.05-1.89 (m, 4H), 1.86 (d, J = 8 Hz, 3H). | 535.53 | 536.37 |
| 3(e) | 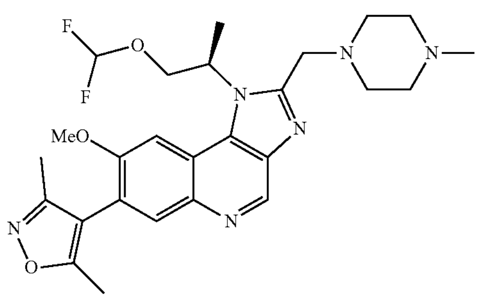 [SMILES: COc1cc2c(cc1-c1c(C)noc1C)ncc1nc(CN3CCN(C)CC3)n([C@H](C)COC(F)F)c12] | ¹H NMR (d6-DMSO 300 MHz) δ 9.05 (s, 1H), 8.02 (s, 1H), 7.53 (s, 1H), 6.68 (t, J = 75 Hz, 1H), 5.68-5.49 (m, 1H), 4.87-4.42 (m, 2H), 4.04-3.72 (m, 2H), 3.98 (s, 3H), 2.57-2.12 (m, 8H), 2.48 (s, 3H), 2.33 (s, 3H), 2.14 (s, 3H), 1.85 (d, J = 6 Hz, 3H). | 514.57 | 515.57 |
| 3(c) | 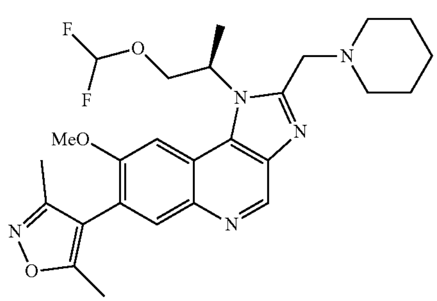 [SMILES: COc1cc2c(cc1-c1c(C)noc1C)ncc1nc(CN3CCCCC3)n([C@H](C)COC(F)F)c12] | ¹H NMR (d6-DMSO 300 MHz) δ 9.49 (s, 1H), 8.35 (s, 1H), 7.94 (s, 1H), 6.71 (t, J = 75 Hz, 1H), 6.04-5.86 (m, 1H), 5.14-4.93 (m, 2H), 4.71-4.38 (m, 2H), 4.38-3.95 (brs, 2H), 4.05 (s, 3H), 3.86-3.54 (m, 2H), 3.39-3.09 (m, 2H), 2.35 (s, 3H), 2.16 (s, 3H), 1.97-1.40 (m, 9H). | 499.55 | 500.39 |

TABLE 2-continued

Summary the ¹H NMR and LCMS characteristics of representative
compounds prepared from intermediate I (Scheme II) with various amines

| Example # | Structure | NMR | MW [M] | Observed LCMS [M + 1] |
|---|---|---|---|---|
| 3(b) | 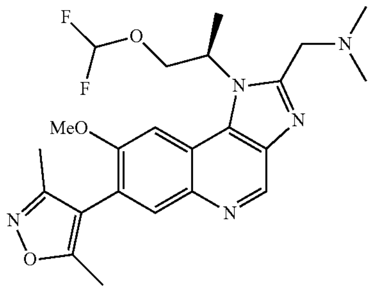 [SMILES: COc1cc2c(cc1-c1c(C)noc1C)ncc1nc(CN(C)C)n([C@H](C)COC(F)F)c12] | ¹H NMR (d6-DMSO 300 MHz) δ 9.06 (s, 1H), 8.02 (s, 1H), 7.52 (s, 1H), 6.67 (t, J = 72 Hz, 1H), 5.80-5.57 (m, 1H), 4.84-4.35 (m, 2H), 3.99 (s, 3H), 3.94 (d, J = 14 Hz, 1H), 3.70 (d, J = 14 Hz, 1H), 2.33 (s, 3H), 2.22 (s, 6H), 2.14 (s, 3H), 1.34 (d, J = 6 Hz, 3H). | 459.49 | 460.39 |
| 3(g) | 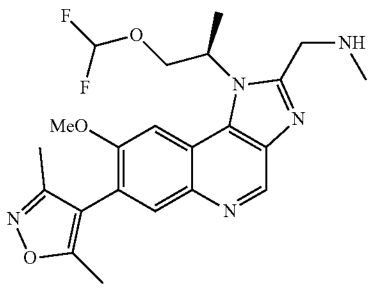 [SMILES: CNCc1nc2cnc3cc(-c4c(C)noc4C)c(OC)cc3c2n1[C@H](C)COC(F)F] | ¹H NMR (d6-DMSO 400 MHz) δ 9.09 (s, 1H), 8.04 (s, 1H), 7.54 (s, 1H), 6.70 (t, J = 76 Hz, 1H), 5.85-5.58 (m, 2H), 4.84-4.61 (m, 2H), 4.61-4.40 (m, 2H), 4.02 (s, 3H), 2.35 (2s, 6H), 2.17 (s, 3H), 1.92-1.73 (m, 3H). | 445.46 | 446.34 |
| 3(h) | 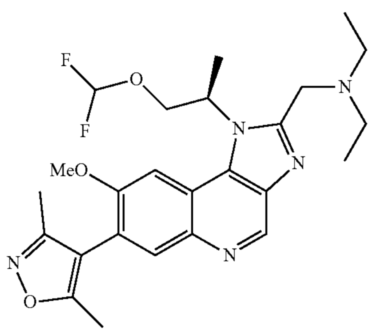 [SMILES: CCN(CC)Cc1nc2cnc3cc(-c4c(C)noc4C)c(OC)cc3c2n1[C@H](C)COC(F)F] | ¹H NMR (d6-DMSO 400 MHz) δ 9.10 (s, 1H), 8.05 (s, 1H), 7.55 (s, 1H), 6.71 (t, J = 76 Hz, 1H), 5.80-5.63 (m, 1H), 4.74-4.41 (m, 2H), 4.15-4.05 (m, 1H), 4.02 (s, 3H), 3.97-3.85 (m, 1H), 2.68-2.45 (m, 4H), 2.36 (s, 3H), 2.17 (s, 3H), 1.88 (d, J = 8 Hz, 3H), 1.08-0.96 (m, 6H). | 487.54 | 488.41 |
| 3(i) | 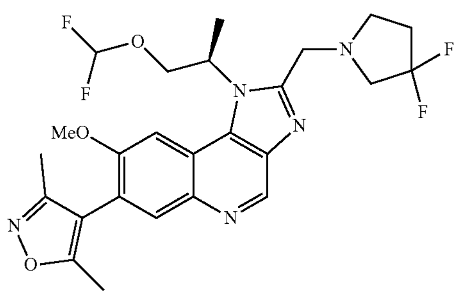 [SMILES: COc1cc2c(cc1-c1c(C)noc1C)ncc1nc(CN3CCC(F)(F)C3)n([C@H](C)COC(F)F)c12] | ¹H NMR (d6-DMSO 400 MHz) δ 9.11 (s, 1H), 8.06 (s, 1H), 7.56 (s, 1H), 6.68 (t, J = 76 Hz, 1H), 5.66-5.48 (m, 1H), 4.79-4.40 (m, 2H), 4.28-4.15 (m, 1H), 4.10-3.97 (m, 1H), 4.02 (s, 3H), 3.15-2.99 (m, 2H), 2.90-2.72 (m, 2H), 2.36 (s, 3H), 2.36-2.21 (m, 2H), 2.17 (s, 3H), 1.93-1.73 (m, 3H). | 521.51 | 522.45 |
| 3(j) | 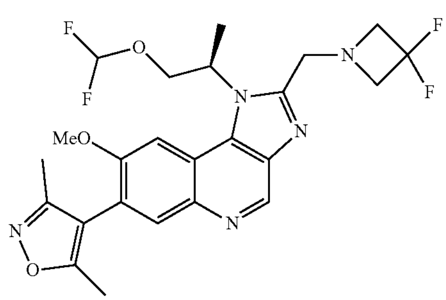 [SMILES: COc1cc2c(cc1-c1c(C)noc1C)ncc1nc(CN3CC(F)(F)C3)n([C@H](C)COC(F)F)c12] | ¹H NMR (d6-DMSO 400 MHz) δ 9.10 (s, 1H), 8.05 (s, 1H), 7.55 (s, 1H), 6.69 (t, J = 76 Hz, 1H), 5.82-5.81 (m, 1H), 4.81-4.60 (m, 1H), 4.60-4.39 (m, 1H), 4.33-4.23 (m, 1H), 4.22-4.11 (m, 1H), 4.02 (s, 3H), 3.85-3.67 (m, 4H), 2.36 (s, 3H), 2.17 (s, 3H), 1.92-1.74 (m, 3H). | 507.48 | 508.41 |

TABLE 3

IC$_{50}$ values of the representative compounds of the application:

| Example # | IC$_{50}$ in nM | | |
|---|---|---|---|
| | BRD2-1 | BRD3-1 | BRD4-FL |
| 2(g) | 24 | 17 | 14 |
| 2(h) | 47 | 31 | 21 |
| 2(l) | 42 | 21 | 33 |
| 2(a) | 63 | 44 | 40 |
| 3(a) | 19 | 10 | 10 |
| 3(b) | 32 | 18 | 32 |
| JQ-1 | 80 | 26 | 19 |

BRD2-1: Domain 1 of BRD2;
BRD3-1: Domain 1 of BRD3;
BRD4-FL: Full length BRD4

TABLE 4

NCI Screening Data

| Panel/Cell Line | 2 g. HCl Log GI50 | 2 l. HCl Log GI50 |
|---|---|---|
| Leukemia | | |
| CCRF-CEM | 48.31 | 52 |
| HL-60(TB) | 27.48 | 31 |
| K-562 | 30.47 | 30.42 |
| MOLT-4 | 46.6 | 42.15 |
| RPMI-8226 | 17.96 | 17.83 |
| SR | 28.32 | 25.53 |
| NSCLC | | |
| A549/ATCC | 36.21 | 36.15 |
| EKVX | 50.39 | 56.92 |
| HOP-62 | 35.22 | 43.39 |
| HOP-92 | 36.91 | 36.96 |
| NCI-H226 | 55.23 | 58.05 |
| NCI-H23 | 600.98 | 65.38 |
| NCI-H322M | 41.17 | 47.84 |
| NCI-H460 | 59.16 | 60.7 |
| NCI-H522 | 31.17 | 27.35 |
| Colon | | |
| COLO 205 | 31.61 | 25.08 |
| HCC-2998 | 47.68 | 57.33 |
| HCT-116 | 40.36 | 37.02 |
| HCT-15 | 22.75 | 23.95 |
| HT29 | 24.52 | 17.28 |
| KM12 | 47.04 | 51.5 |
| SW-620 | 59.04 | 62.66 |
| CNS | | |
| SF-268 | 65.47 | 71.22 |
| SF-295 | 49.75 | 56.8 |
| SF-539 | 33.59 | 39.43 |
| SNB-19 | 47.57 | 60.12 |
| SNB-75 | 29.9 | 34.32 |
| U251 | 51.8 | 52.75 |
| Melanoma | | |
| LOX IMVI | 12.62 | 15.45 |
| MALME-3M | 71.7 | 80.4 |
| M14 | 46.19 | 44.23 |
| MDA-MB-435 | 40.59 | 44.31 |
| MDA-N | | |
| SK-MEL-2 | 67.01 | 74.07 |
| SK-MEL-28 | 55.81 | 63.46 |
| SK-MEL-5 | | |
| UACC-257 | 31.76 | 36.29 |
| UACC-62 | 17.81 | 25.53 |
| Ovarian | | |
| IGROV1 | 58.77 | 58.6 |
| OVCAR-3 | 35.24 | 42.03 |
| OVCAR-4 | 47.87 | 58.71 |
| OVCAR-5 | 68.44 | 84.19 |
| OVCAR-8 | 42.56 | 46.31 |
| NCI/ADR-RES | 38.43 | 40.11 |
| SK-OV-3 | 1.35 | 1.36 |
| Renal | | |
| 786-0 | 47.98 | 51.62 |
| A498 | −13.55 | 0.5 |
| ACHN | 34.63 | 40.55 |
| CAKI-1 | 26.66 | 34.09 |
| RXF 393 | 54.76 | 53.88 |
| SN12C | 56.99 | 71.4 |
| TK-10 | 25.33 | 26.49 |
| UO-31 | 15.7 | 21.65 |
| Prostate | | |
| PC-3 | 34.26 | 39.06 |
| DU-145 | 69.24 | 72.41 |
| Breast | | |
| MCF7 | 19.19 | 21.73 |
| MDA-MB-231/ATCC | 4.63 | 50.99 |
| HS 578T | 16.77 | 8.14 |
| BT-549 | 68.79 | 71.62 |
| T-47D | 46.04 | 32.75 |
| MDA-MB-468 | 39.98 | 45.96 |

TABLE 5

Oncology Cell Growth Assay Results

| Cell Line | Tumor Type | 2 g-HCl IC$_{50}$ (μM) | 2 l-HCl IC$_{50}$ (μM) |
|---|---|---|---|
| AML2 | AML (acute myeloid leukemia) | 0.018 ± 0.002 | 0.015 ± 0.001 |
| HL60 | Promyelocytic leukemia | 0.051 ± 0.003 | 0.179 ± 0.01 |
| TEX | AML (acute lymphoid leukemia) | 0.023 ± 0.002 | 0.052 ± 0.073 |
| MV4-11 | CML (chronic myeloid) leukemia | 0.014 ± 0.007 | 0.156 ± 0.043 |
| MOLT4 | acute lymphoid leukemia | 1.137 | — |
| RPMI-8226 | Multiple myeloma | 0.303 ± 0.006 | 0.109 ± 0.032 |
| MM.1S | Multiple myeloma | 0.017 ± 0.004 | 0.094 ± 0.014 |
| SK-OV-3 | Ovarian cancer | 2.182 ± 1.44 | 0.36 ± 0.01 |

TABLE 6

Bromodomain EC$_{50}$ values for a representative compounds of the application

| Compound ID# | Structure | EC$_{50}$ (M) | | |
|---|---|---|---|---|
| | | BRD2-1 | BRD3-1 | BRD4-FL |
| 2(a) or 5(b) | | 6.34E−08 | 4.38E−08 | 4.04E−08 |
| 2(g) | | 6.89E−09 | 2.76E−09 | 7.17E−09 |
| 2(h) | | 2.73E−08 | 6.96E−09 | 4.62E−08 |

TABLE 6-continued

Bromodomain EC$_{50}$ values for a representative compounds of the application

| Compound ID# | Structure | EC$_{50}$ (M) | | |
| --- | --- | --- | --- | --- |
| | | BRD2-1 | BRD3-1 | BRD4-FL |
| 2(l) | 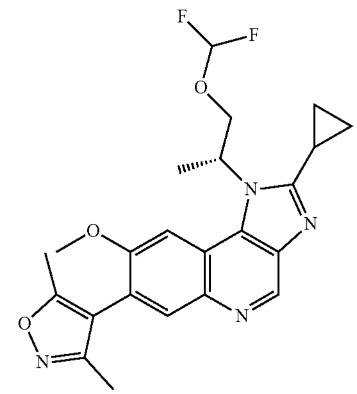 [SMILES: COc1cc2c(cc1-c1c(C)noc1C)ncc1nc(C3CC3)n([C@H](C)COC(F)F)c12] | 4.22E−08 | 2.07E−08 | 3.31E−08 |
| 2(r) | 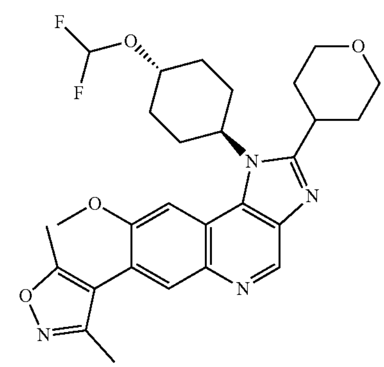 [SMILES: COc1cc2c(cc1-c1c(C)noc1C)ncc1nc(C3CCOCC3)n([C@H]3CC[C@H](OC(F)F)CC3)c12] | 2.81E−07 | 1.04E−07 | 4.06E−07 |
| 3(a)•HCl | 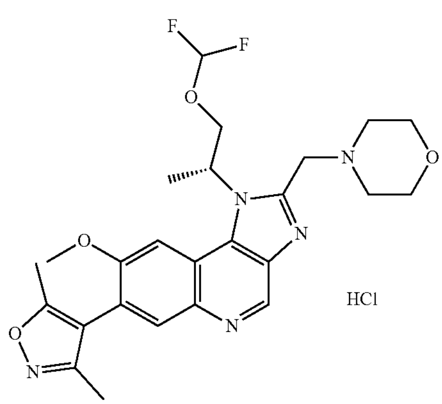 [SMILES: COc1cc2c(cc1-c1c(C)noc1C)ncc1nc(CN3CCOCC3)n([C@H](C)COC(F)F)c12 ; Cl] | 1.93E−08 | 1.00E−08 | 9.52E−09 |

TABLE 6-continued
Bromodomain EC$_{50}$ values for a representative compounds of the application
| Compound ID# | Structure | EC$_{50}$ (M) BRD2-1 | BRD3-1 | BRD4-FL |
|---|---|---|---|---|
| 3(b)•HCl | 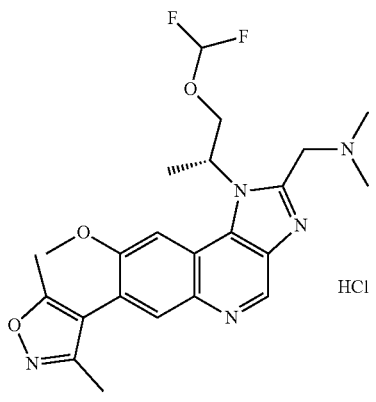 [SMILES: COc1cc2c(cc1-c1c(C)noc1C)ncc1nc(CN(C)C)n([C@H](C)COC(F)F)c12 ; Cl] | 3.23E−08 | 1.76E−08 | 3.17E−08 |
| JQ-1 | 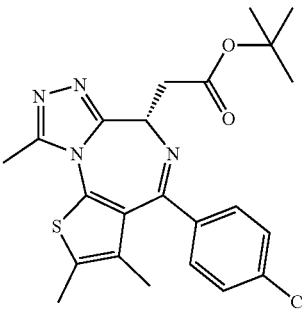 | 7.96E−08 | 2.64E−08 | 1.93E−08 |
TABLE 7
% recovery of compounds of the application from human and mouse liver microsomes
| Compound | Structure | Mouse Liver Microsomes (MLM) (30 min) | Human Liver Microsomes (HLM) (30 min) |
|---|---|---|---|
| 2(g) | 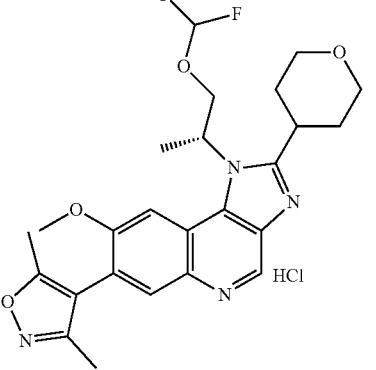 | 55.5 | 43 |

TABLE 7-continued

% recovery of compounds of the application from human and mouse liver microsomes

| Compound | Structure | Mouse Liver Microsomes (MLM) (30 min) | Human Liver Microsomes (HLM) (30 min) |
|---|---|---|---|
| 2(h) | 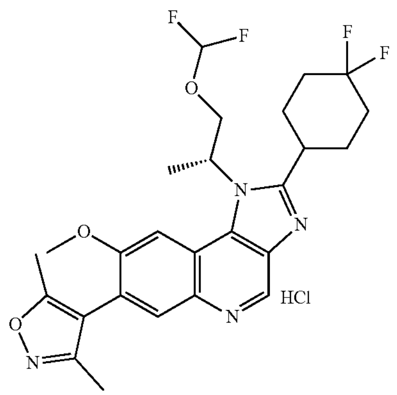 [SMILES: COc1cc2c(cc1-c1c(C)noc1C)ncc1nc(C3CCC(F)(F)CC3)n([C@H](C)COC(F)F)c12 ; Cl] | 35.2 | 62.3 |
| 2(j) | 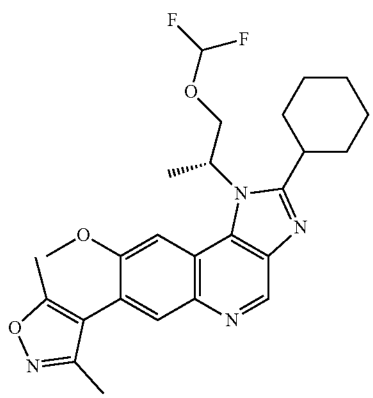 | 7 | 1.5 |
| 2(k) | 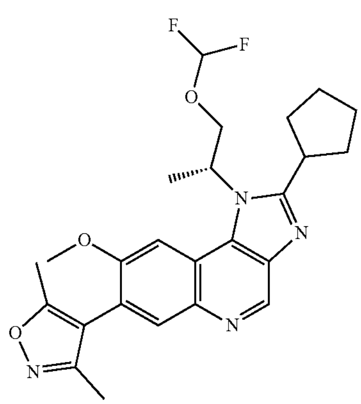 [SMILES: COc1cc2c(cc1-c1c(C)noc1C)ncc1nc(C3CCCC3)n([C@H](C)COC(F)F)c12] | 0.6 | 0.1 |

TABLE 7-continued

% recovery of compounds of the application from human and mouse liver microsomes

| Compound | Structure | Mouse Liver Microsomes (MLM) (30 min) | Human Liver Microsomes (HLM) (30 min) |
|---|---|---|---|
| 2(l)•HCl | 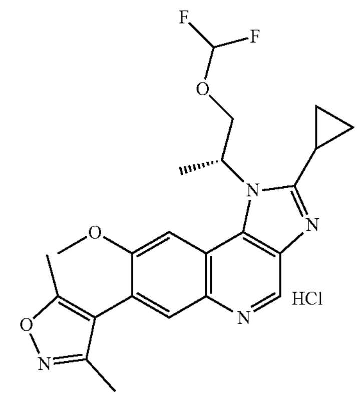 [SMILES: COc1cc2c(cc1-c1c(C)noc1C)ncc1nc(C3CC3)n([C@H](C)COC(F)F)c12 ; Cl] | 3 | 43.6 |
| 3(a) | 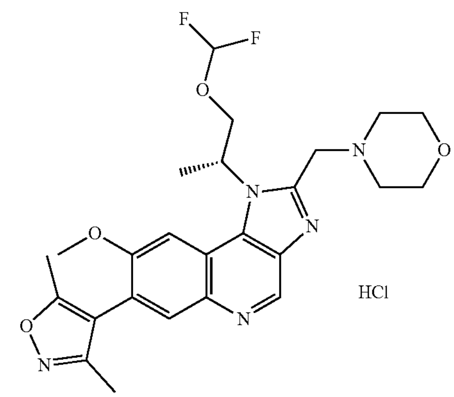 [SMILES: COc1cc2c(cc1-c1c(C)noc1C)ncc1nc(CN3CCOCC3)n([C@H](C)COC(F)F)c12 ; Cl] | 3.7 | 1.9 |
| 3(b) | 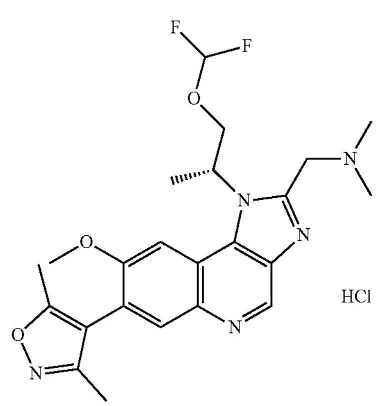 [SMILES: COc1cc2c(cc1-c1c(C)noc1C)ncc1nc(CN(C)C)n([C@H](C)COC(F)F)c12 ; Cl] | 0.5 | 13.7 |

TABLE 7-continued
% recovery of compounds of the application from human and mouse liver microsomes
| Compound | Structure | Mouse Liver Microsomes (MLM) (30 min) | Human Liver Microsomes (HLM) (30 min) |
|---|---|---|---|
| 3(f) | 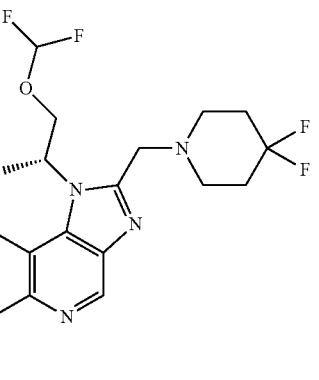 | 2.6 | 0.6 |
| 2(n) | 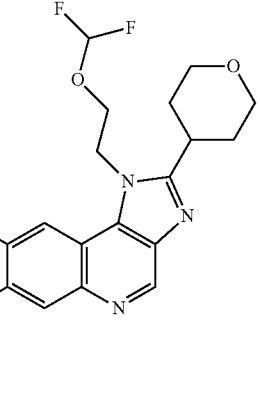 | 74.8 | 58.1 |
| 3(g) | 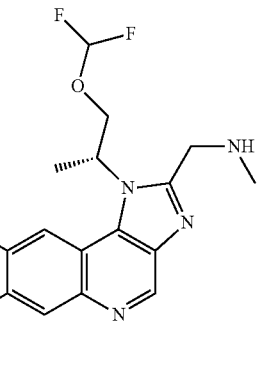 | 0.1 | 58.5 |

TABLE 7-continued

% recovery of compounds of the application from human and mouse liver microsomes

| Compound | Structure | Mouse Liver Microsomes (MLM) (30 min) | Human Liver Microsomes (HLM) (30 min) |
|---|---|---|---|
| 3(i) | 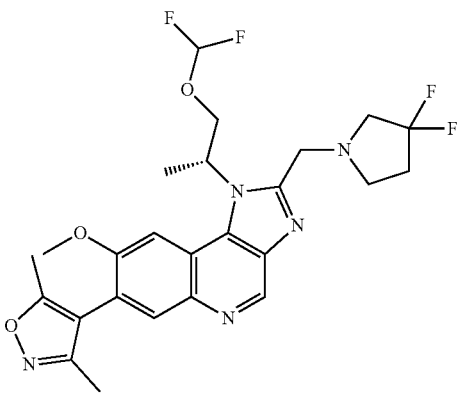 [SMILES: COc1cc2c(cc1-c1c(C)noc1C)ncc1nc(CN3CCC(F)(F)C3)n([C@H](C)COC(F)F)c12] | 10.4 | 7.4 |
| 3(j) | 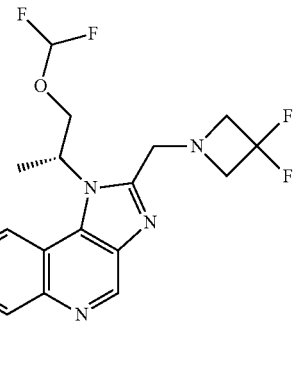 | 8 | 6.9 |

TABLE 8

Group and Treatments

| Group# | Drug | Animals/Group | Dose (mg/kg) | Vol (ml/Kg) | Route | Regimen |
|---|---|---|---|---|---|---|
| 1 | Vehicle | 10 | — | 20 | PO | QD × 14 |
| 2 | 2g-HCl | 10 | 10 | 20 | PO | QD × 14 |
| 3 | 2g-HCl | 10 | 30 | 20 | PO | QD × 14 |
| 4 | 2g-HCl | 10 | 50 | 20 | PO | PG-D1-7* PG-D10-13* |
| 5 | 2l-HCl | 10 | 30 | 20 | PO | QD × 14 |
| 6 | 2l-HCl | 10 | 50 | 20 | PO | QD × 14 |

Note:
The dosing would be suspended when the body weight loss is above 15%.
*Suspended the treatment as the client required.

TABLE 9

Groups and treatments

| Group # | Drug | Animals/group | Dose (mg/kg) | Vol (ml/kg) | Route | Regimen |
|---|---|---|---|---|---|---|
| 1 | Vehicle | 10 | — | — | PO | QD × 21 |
| 2 | 2(g) | 10 | 10 | 20 | PO | QD × 21 |
| 3 | 2(g) | 10 | 30 | 20 | PO | QD × 21 |
| 4 | 2(g) | 10 | 60 | 20 | PO | QD × 21 |
| 5 | Carfilzomib | 10 | 5 | 10 | IV | Days 1, 2/wk × 21 |

Vehicle: 0.5% HPBCD solution

TABLE 10

Preparation of dosing formulation

| Compounds | Preparation | Concentration (mg/ml) | Storage |
|---|---|---|---|
| Vehicle | 0.5% HP-beta-cyclodextrin: 0.5 g HP-beta-cd is dissolved 100 ml ddH$_2$0. | — | |

TABLE 10-continued

| Preparation of dosing formulation | | | |
|---|---|---|---|
| Compounds | Preparation | Concentration (mg/ml) | Storage |
| Compound 2 (g) | 1) 2.5 mg compound 2 (g) in 5 ml 0.5% HP-beta-cyclodextrin was prepared.<br>2) Sonication for 5 s every time until the mixture is dissolved.<br>3) For 0.2 ml/10 g (mice body weight) and 10 mg/Kg<br>4) Final: 0.25 mg/0.5 ml/25 g<br>(2.5 mg/5 ml/250 g for 10 mice) | 0.5 mg/ml | use immediatly |
| | 1) 7.5 mg of compound 2 (g) in 5 ml 0.5% HP-beta-cyclodextrin was prepared.<br>2) Sonication for 5 s every time until the mixture is dissolved.<br>3) For 0.2 ml/10 g (mice body weight) and 30 mg/Kg<br>4) Final: 0.75 mg/0.5 ml/25 g<br>(7.5 mg/5 ml/250 g for 10 mice) | 1.5 mg/ml | use immediatly |
| | 1) 15 mg FV-281.HCL in 5 ml 0.5% HP-beta-cyclodextrin was prepared.<br>2) Sonication for 5 s every time until it is dissolved.<br>3) For 0.2 ml/10 g (mice body weight) and 50 mg/Kg<br>4) Final: 1.5 mg/0.5 ml/25 g (15 mg/5 ml/250 g for 10 mice) | 3 mg/ml | use immediatly |
| CFZ | 1) 2.5 mg FV-207 in 0.5 mL buffer (10 mM citrate acid, pH = 3.5, 10% Captisol (w/v) was prepared.<br>2) Sonication for 20 s, 3 times until the mixture dissolved.<br>3) pH was adjusted to neutral by adding PBS 2 ml (10% Captisol (w/v), pH = 7.4). Total volume should be 2.5 ml.<br>4) Sonication for 20 s, 3 times until mixture is dissolved and clear.<br>5) 0.1 ml/10 g for mice (mice body weight) is needed, therefore 0.25 mg/0.25 ml/25 g (2.5 mg/2.5 ml/250 g for 10 mice) = 1 mg/ml | 1 mg/ml | use immediatly |

TABLE 11

| Dosing route, frequency and duration of treatment | | | | | |
|---|---|---|---|---|---|
| Group | Treatment | Dose (mg/kg) | Route | Frequency | Duration |
| 1 | Vehicle | 0 | PO | daily | 21 days |
| 2 | Compound 2 (g) | 10 | PO | daily | 21 days |
| 3 | Compound 2 (g) | 30 | PO | daily | 21 days |
| 4 | Compound 2 (g) | 60 | PO | daily | 21 days |
| 6 | Carfilzomib (CFZ) | 5 | IV | weekly | 21 days |

The invention claimed is:

1. A compound of Formula I or a pharmaceutically acceptable salt and/or solvate thereof:

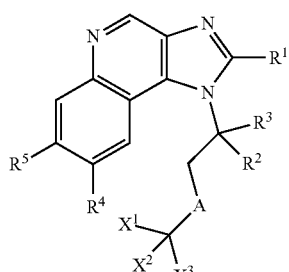

Formula I wherein:
$R^1$ is selected from optionally substituted $C_{3-20}$cycloalkyl and optionally substituted $C_{1-6}$alkylene$C_{3-10}$cycloalkyl;
$R^2$ and $R^3$ are independently selected from H, fluoro, $C_{1-6}$alkyl, $C_{1-6}$alkylOR$^6$, $C_{1-6}$alkylCOOR$^6$, $C_{1-6}$alkylCONR$^6$R$^7$, $C_{1-6}$alkylSR$^6$, $C_{1-6}$alkylSOR$^6$, $C_{1-6}$alkylSO$_2$R$^6$ and $C_{1-6}$alkylNR$^6$R$^7$, or R$^2$ and R$^3$ together form an oxo (═O) group, or R$^2$ and R$^3$, together with the carbon atom to which they are attached, form $C_{3-7}$cycloalkyl or $C_{3-7}$heterocycloalkyl;

R$^4$ is selected from H, optionally substituted $C_{1-20}$alkyl, optionally substituted $C_{2-20}$alkenyl, optionally substituted $C_{3-20}$cycloalkyl, optionally substituted $C_{6-20}$aryl, optionally substituted heterocycloalkyl, optionally substituted heteroaryl, optionally substituted $C_{1-6}$alkylene$C_{3-10}$cycloalkyl, optionally substituted $C_{1-6}$alkylenearyl, optionally substituted $C_{1-6}$alkyleneheterocycloalkyl, optionally substituted $C_{1-6}$alkyleneheteroaryl, OR$^6$, CN, COOH, COOR$^6$, COONH$_2$, COONR$^6$R$^7$, $C_{1-6}$alkyleneOR$^6$, NR$^6$R$^7$, $C_{1-6}$alkyleneNR$^6$R$^7$, $C_{1-6}$alkyleneCONR$^6$R$^7$, SR$^6$, CN, $C_{1-6}$alkyleneOR$^6$, NR$^6$R$^7$ and halogen;

R$^5$ is selected from H, optionally substituted monocyclic rings having 0-3 heteroatoms independently selected from N, O and S and the optional substituents are selected from 1 to 3 $C_{1-6}$alkyl and $C_{1-6}$alkoxy, optionally substituted $C_{1-20}$alkyl, optionally substituted $C_{2-20}$alkenyl, optionally substituted $C_{3-20}$cycloalkyl, optionally substituted $C_{6-20}$aryl, optionally substituted heterocycloalkyl, optionally substituted heteroaryl, optionally substituted $C_{1-6}$alkylene$C_{3-10}$cycloalkyl, optionally substituted $C_{1-6}$alkylenearyl, optionally substituted $C_{1-6}$alkyleneheterocycloalkyl, optionally substituted $C_{1-6}$alkyleneheteroaryl, OR$^6$, —CN, COOR$^6$, CONR$^6$R$^7$, $C_{1-6}$alkyleneOR$^6$, $C_{1-6}$alkyleneCOOR$^6$, NR$^6$R$^7$, $C_{1-6}$alkyleneNR$^6$R$^7$, $C_{1-6}$alkyleneCONR$^6$R$^7$, $C_{1-6}$alkyleneCSNR$^6$R$^7$, SR$^6$, $C_{1-6}$alkyleneSR$^6$, SOR$^6$, $C_{1-6}$alkyleneSOR$^6$, SO$_2$R$^6$ and $C_{1-6}$alkyleneSO$_2$R$^6$;

R$^6$ and R$^7$ are each independently selected from H, $C_{1-6}$alkyl, $C_{3-10}$cycloalkyl, heterocycloalkyl and haloC$_{1-6}$alkyl;

A is selected from $C_{0-6}$alkylene, O, S, SO, SO$_2$ and NR$^6$;

X$^1$, X$^2$ and X$^3$ are the same or different and are selected from H, halogen, and $C_{1-6}$alkyl, provided that at least one of X$^1$, X$^2$ and X$^3$ is F;

R$^1$ is optionally substituted with 1 to 2 of methyl, ethyl and F; and one or more of the atoms in the compounds of Formula I are optionally replaced with a radioactive isotope thereof.

2. The compound of claim 1, wherein R$^1$ is optionally substituted $C_{3-6}$cycloalkyl or optionally substituted CH$_2$C$_{3-6}$cycloalkyl.

3. The compound of claim 1, wherein R$^1$ is unsubstituted.

4. The compound of claim 1, wherein R$^1$ is substituted with 1 to 2 substituent groups selected from methyl and F.

5. The compound of claim 1, wherein R$^1$ is selected from:

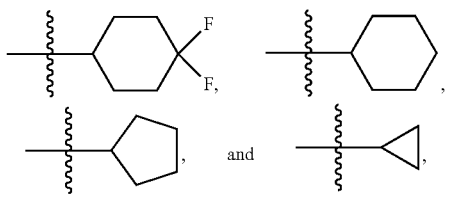

wherein ∿ represents the point of attachment of the group to the remaining portion of the compounds of Formula I.

6. The compound of claim 1, wherein R$^2$ and R$^3$ are independently selected from H, fluoro, and $C_{1-4}$alkyl.

7. The compound of claim 1, wherein the carbon atom to which R$^2$ and R$^3$ is attached is a chiral center and greater than 90% of the molecules in a sample of the compound of Formula I, has a stereochemistry at the carbon atom to which R$^2$ and R$^3$ is attached that is R.

8. The compound of claim 1, wherein R$^2$ and R$^3$ together form an oxo (═O) group.

9. The compound of claim 1, wherein R$^2$ and R$^3$, together with the carbon atom to which they are attached, form $C_{5-6}$cycloalkyl.

10. The compound of claim 1, wherein R$^4$ is selected from OH, OC$_{1-6}$alkyl, $C_{1-6}$alkyleneOH, $C_{1-6}$alkyleneOC$_{1-6}$alkyl, NH$_2$, NHC$_{1-6}$alkyl, N(C$_{1-6}$alkyl)$_2$, $C_{1-6}$alkyleneNH$_2$, $C_{1-6}$alkyleneNHC$_{1-6}$alkyl, $C_{1-6}$alkyleneN(C$_{1-6}$alkyl)$_2$, F and Cl.

11. The compound of claim 1, wherein, R$^5$ is selected from optionally substituted monocyclic rings having 1-3 heteroatoms independently selected from N, O and S and the optional substituents are selected from 1 to 2 $C_{1-4}$alkyl and $C_{1-4}$alkoxy.

12. The compound of claim 1, wherein R$^6$ and R$^7$ are each independently selected from H and CH$_3$.

13. The compound of claim 1, wherein A is selected from $C_{0-1}$alkylene, O, NH and NCH$_3$.

14. The compound of claim 1, wherein X$^1$, X$^2$ and X$^3$ are the same or different and are selected from H, F, and $C_{1-4}$alkyl, provided that at least one of X$^1$, X$^2$ and X$^3$ is F.

15. The compound of claim 1, selected from:

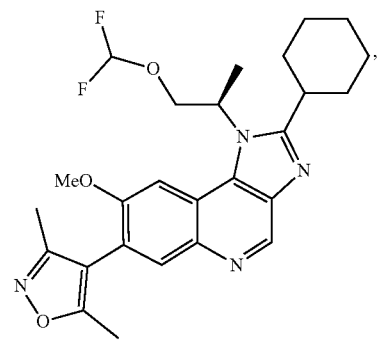

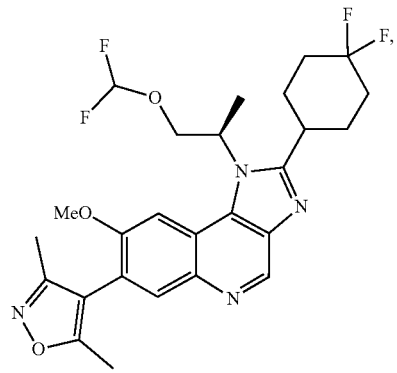

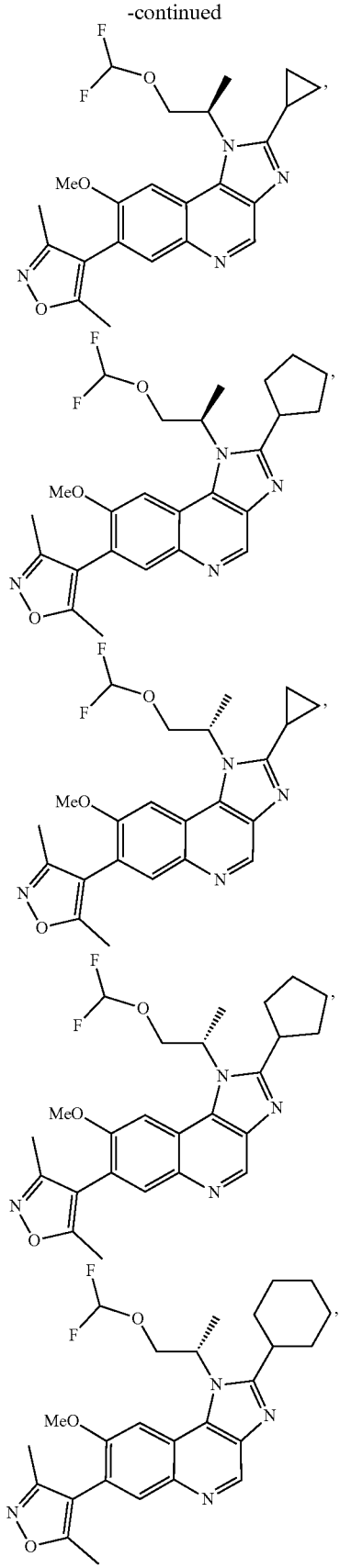

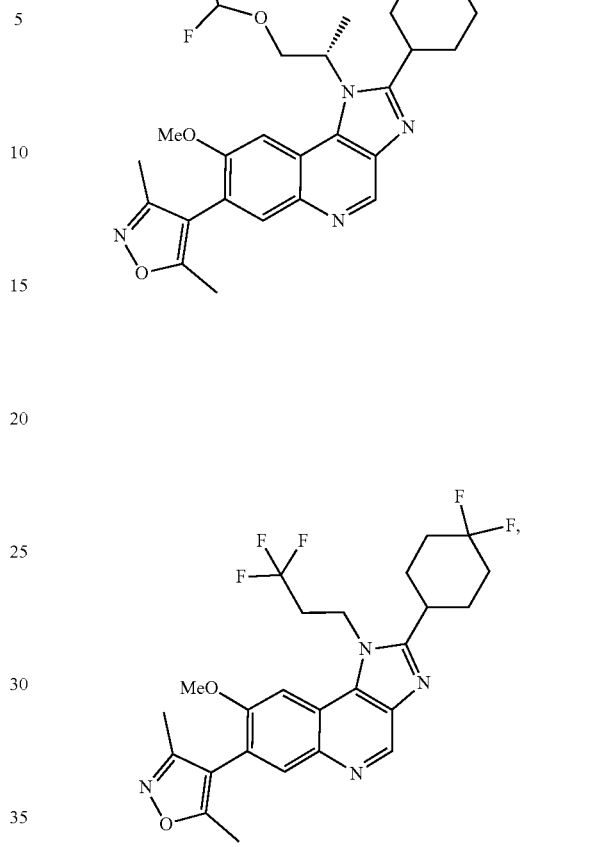

or a pharmaceutically acceptable salt and/or solvate thereof.

16. A pharmaceutical composition comprising one or more compounds of Formula (I) of claim 1, or a pharmaceutically acceptable salt, and/or solvate thereof, and a pharmaceutically acceptable carrier and/or diluent.

17. The compound of claim 1 that is:

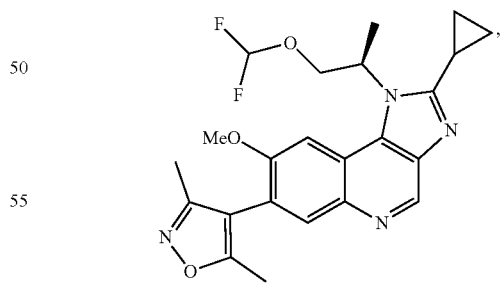

or a pharmaceutically acceptable salt and/or solvate thereof.

18. The compound of claim 17, in the form of a hydrochloride salt.

* * * * *